United States Patent
Osawa et al.

(10) Patent No.: US 10,899,792 B2
(45) Date of Patent: Jan. 26, 2021

(54) PRODUCTION METHOD FOR INSOLUBLE RECOMBINANT PROTEIN AGGREGATE

(71) Applicant: Spiber Inc., Yamagata (JP)

(72) Inventors: Toshiaki Osawa, Yamagata (JP); Yuya Sato, Yamagata (JP); Keisuke Morita, Yamagata (JP)

(73) Assignee: Spiber Inc., Yamagata (JP)

( * ) Notice: Subject to any disclaimer, the term of this patent is extended or adjusted under 35 U.S.C. 154(b) by 0 days.

(21) Appl. No.: 16/324,280

(22) PCT Filed: Aug. 10, 2017

(86) PCT No.: PCT/JP2017/029033
§ 371 (c)(1),
(2) Date: Feb. 8, 2019

(87) PCT Pub. No.: WO2018/030499
PCT Pub. Date: Feb. 15, 2018

(65) Prior Publication Data
US 2019/0177363 A1 Jun. 13, 2019

(30) Foreign Application Priority Data

Aug. 10, 2016 (JP) ................. 2016-157912
Nov. 25, 2016 (JP) ................. 2016-229227
Mar. 14, 2017 (JP) ................. 2017-048702
May 10, 2017 (JP) ................. 2017-094144

(51) Int. Cl.
*C07K 1/34* (2006.01)
*C07K 1/30* (2006.01)
*C12P 21/02* (2006.01)
*C12P 21/00* (2006.01)
*C07K 1/14* (2006.01)

(52) U.S. Cl.
CPC ............ *C07K 1/34* (2013.01); *C07K 1/14* (2013.01); *C07K 1/30* (2013.01); *C12P 21/00* (2013.01); *C12P 21/02* (2013.01)

(58) Field of Classification Search
None
See application file for complete search history.

(56) References Cited

U.S. PATENT DOCUMENTS 5,235,041 A * 8/1993 Cappello ................. C07K 1/36
530/353

FOREIGN PATENT DOCUMENTS

| JP | 2001-238693 A | 9/2001 |
|---|---|---|
| JP | 2004-503204 A | 2/2004 |
| JP | 2004-315682 A | 11/2004 |
| JP | 2008-506409 A | 3/2008 |
| JP | 2013-523665 A | 6/2013 |
| JP | 2016-504918 A | 2/2016 |
| WO | 01/053333 A1 | 7/2001 |
| WO | 2004/065608 A1 | 8/2004 |
| WO | 2006/008163 A2 | 1/2006 |
| WO | 2011/120690 A2 | 10/2011 |
| WO | 2014/118220 A1 | 1/2014 |

OTHER PUBLICATIONS

Liebmann et al.,"Formulation of poorly water-soluble substances using self-assembling spider silk protein", Colloids and Surfaces A: Physicochem. Eng. Aspects 331: 126-132. (Year: 2008).*
Huemmerich et al.,"Prinnary structure elements of spider dragline silks and their contributions to protein solubility", Biochemistry 43: 13604-13612. (Year: 2004).*
Barr et al.,"Production and purification of recombinant DP1B silk-like protein in plants", Molecular Breeding 13: 345-356. (Year: 2004).*
Aoki, "Application of Separation Plate Type Centrifuge to Material with Low Filterability," //www.jstage.jst.go.jp/article/scej/2006f/0/2006f_0_255/_pdf> SCEJ 28th Autumn Meeting (2017) (see partial English translation).
International Search Report issued in corresponding International Patent Application No. PCT/JP2017/029033 dated Nov. 7, 2017.
International Preliminary Report on Patentability and Written Opinion issued in corresponding International Patent Application No. PCT/JP2017/029033 dated Feb. 21, 2019.

* cited by examiner

*Primary Examiner* — Anand U Desai
(74) *Attorney, Agent, or Firm* — Morgan, Lewis & Bockius LLP

(57) ABSTRACT

An object of the present invention is to provide a method for efficiently separating insoluble bodies of a recombinant protein from a recombinant cell expressing a target recombinant protein as insoluble bodies in the cell. The present invention provides a method for producing a recombinant protein aggregate by separating insoluble bodies of a recombinant protein from a recombinant cell expressing the recombinant protein as insoluble bodies in the cell, including disrupting the recombinant cell, aggregating the insoluble bodies of the recombinant protein, and separating the resulting aggregate.

17 Claims, 16 Drawing Sheets
Specification includes a Sequence Listing.

PRODUCTION METHOD FOR INSOLUBLE RECOMBINANT PROTEIN AGGREGATE

SEQUENCE LISTING SUBMISSION VIA EFS-WEB

A computer readable text file, entitled "SequenceListing.txt" created on or about Feb. 8, 2019 with a file size of about 84 kb contains the sequence listing for this application and is hereby incorporated by reference in its entirety.

TECHNICAL FIELD

The present invention relates to a method for producing an insoluble recombinant protein aggregate by a method of separating insoluble bodies of a recombinant protein from a recombinant cell expressing the insoluble recombinant protein, and an insoluble recombinant protein aggregate obtained by the method.

BACKGROUND ART

Industrial-scale production of a target protein has been made possible by using a genetic recombinant host cell. Many methods for isolating and purifying a recombinant protein produced by a recombinant cell have been reported.

In the case where the recombinant protein as insoluble bodies is compactly produced as insoluble granules in the recombinant cell, it is possible to isolate the insoluble granules in relatively high yield and high purity by centrifuging a suspension containing a component such as a protein derived from a host cell. For example, a method of isolating a target protein from insoluble recombinant cells solubilized with a metal hydroxide such as sodium hydroxide (Patent Literature 1), and the like have been reported.

On the other hand, for example, the following purification methods have been reported in the case where it is difficult to separate the recombinant protein by centrifugation even in the case where the recombinant protein is in a solubilized state or insoluble bodies in recombinant cells, unlike compact insoluble granules. That is, for example, a method in which a protein derived from a host cell is hydrolyzed with an organic acid such as formic acid or propionic acid, insoluble bodies derived from a host cell are removed by centrifugation or the like, and then the target recombinant protein is recovered in an undenatured state and purified by a technique such as chromatography (Patent Literature 2) has been reported. In this report, the target protein remains in an undenatured state even in the case where the organic acid is added, and does not aggregate.

Not a target recombinant protein is necessarily produced as insoluble granules in a recombinant cell. It is known that the state of formation of insoluble granules greatly changes depending on the nature of the target recombinant protein itself or various parameters of the culturing process such as medium composition at the time of production, culture temperature, and production rate. Therefore, studies are directed to the modification of a recombinant protein or the development of an efficient production method thereof so as to produce large insoluble granules that can be centrifuged as easily as possible.

On the other hand, in the case where there is a method which is capable of easily separating fine insoluble bodies or insoluble granules that are difficult or very time consuming for centrifugation, by centrifugation, filtration, or the like, it is very industrially useful, but such a method is not known.

CITATION LIST

Patent Literature

[Patent Literature 1] Japanese Unexamined Patent Publication No. 2013-523665
[Patent Literature 2] Japanese Unexamined Patent Publication No. 2004-503204

SUMMARY OF INVENTION

Technical Problem

An object of the present invention is to provide a method for efficiently separating insoluble bodies of a recombinant protein from a recombinant cell expressing a target recombinant protein as insoluble bodies in the cell, and a method for producing a recombinant protein aggregate by the separation method.

Solution to Problem

As a result of extensive studies on a method which is capable of easily separating fine insoluble bodies or insoluble granules of a recombinant protein that are difficult or very time consuming for centrifugation, the present inventors have found that the recombinant protein can be easily separated by efficiently aggregating the insoluble bodies or insoluble granules to be enlarged. The present invention has been completed based on these findings.

That is, the present invention relates to, for example, each of the following inventions.

[1] A method for producing a recombinant protein aggregate by separating insoluble bodies of a recombinant protein as an aggregate from a recombinant cell expressing the recombinant protein as insoluble bodies in the cell, including disrupting the recombinant cell, aggregating the insoluble bodies of the recombinant protein, and separating the resulting aggregate.

[2] The method for producing a recombinant protein aggregate according to [1], further including separating the recombinant protein aggregate by a centrifugal force of 10,000×g or less.

[3] The method for producing a recombinant protein aggregate according to [1] or [2], further including separating the recombinant protein aggregate by using a centrifuge selected from the group consisting of a separation plate type centrifuge, a basket type centrifuge, and a decanter type centrifuge.

[4] The method for producing a recombinant protein aggregate according to [1], further including separating the recombinant protein aggregate by spontaneous sedimentation or filtration.

[5] The method for producing a recombinant protein aggregate according to any one of [1] to [4], in which aggregation of the insoluble bodies of the recombinant protein is carried out by adding one or more selected from the group consisting of a metal salt, an acid, and an anionic flocculant.

[6] A method for producing a recombinant protein aggregate, including the following steps (A) to (C):

a step (A) of disrupting a recombinant cell expressing a target recombinant protein as insoluble bodies in the cell to obtain a disrupted suspension containing the insoluble bodies of the recombinant protein;

a step (B) of adding one or more selected from the group consisting of a metal salt, an acid, and an anionic flocculant to the disrupted suspension obtained in the step (A), and aggregating the insoluble bodies of the recombinant protein to obtain the recombinant protein aggregate; and a step (C) of separating the aggregate obtained in the step (B) from the suspension.

[7] The method for producing a recombinant protein aggregate according to [6], further including heating in the step (B).

[8] The method for producing a recombinant protein aggregate according to claim 7, further including stirring in the step (B).

[9] The method for producing a recombinant protein aggregate according to any one of [5] to [8], in which the metal salt is a metal salt selected from the group consisting of an alkaline earth metal salt and an earth metal salt.

[10] The method for producing a recombinant protein aggregate according to [9], in which the metal salt is a metal salt selected from the group consisting of an alkaline earth metal halide, an alkaline earth metal nitrate, an alkaline earth metal sulfate, an earth metal halide, an earth metal nitrate, and an earth metal sulfate.

[11] The method for producing a recombinant protein aggregate according to any one of [5] to [10], in which the acid is an oxo acid.

[12] The method for producing a recombinant protein aggregate according to [11], in which the oxo acid is an oxo acid selected from the group consisting of acetic acid, sulfuric acid, and citric acid.

[13] The method for producing a recombinant protein aggregate according to any one of [5] to [12], in which the anionic flocculant is an anionic flocculant selected from the group consisting of a polyacrylate, an anionic polyacrylamide, and an acrylamide-acrylate copolymer.

[14] The method for producing a recombinant protein aggregate according to any one of [1] to [13], in which the disruption of the recombinant cell is mechanical disruption.

[15] The method for producing a recombinant protein aggregate according to any one of [1] and [6] to [14], in which the separation of the recombinant protein aggregate is carried out by filtration.

[16] The method for producing a recombinant protein aggregate according to any one of [1] to [15], in which the recombinant cell is a recombinant cell transformed with a host selected from the group consisting of a bacterium, a yeast, a filamentous fungus, an insect cell, a plant cell, and an animal cell.

[17] The method for producing a recombinant protein aggregate according to any one of [1] to [16], in which the recombinant protein is a structural protein.

[18] The method for producing a recombinant protein aggregate according to [17], in which the structural protein is a protein derived from a protein selected from the group consisting of keratin, collagen, elastin, resilin, silkworm silk, and spider silk.

[19] The method for producing a recombinant protein aggregate according to any one of [1] to [18], in which the resulting recombinant protein aggregate has a particle size of 4 μm or more and 50 μm or less as measured by an electrical sensing zone method.

[20] A recombinant protein aggregate obtained by the method for producing a recombinant protein aggregate according to any one of [1] to [18], which has a particle size of 4 μm or more and 50 μm or less as measured by an electrical sensing zone method.

[21] A method for separating insoluble bodies of a recombinant protein from a recombinant cell expressing the recombinant protein as insoluble bodies in the cell, including disrupting the recombinant cell, aggregating the insoluble bodies of the recombinant protein, and separating the resulting aggregate.

[22] The method for separating a recombinant protein according to [21], further including separating the recombinant protein aggregate by a centrifugal force of 10,000×g or less.

[23] The method for separating a recombinant protein according to [21] or [22], further including separating the recombinant protein aggregate by using a centrifuge selected from the group consisting of a separation plate type centrifuge, a basket type centrifuge, and a decanter type centrifuge.

[24] The method for separating a recombinant protein according to [21], further including separating the recombinant protein aggregate by spontaneous sedimentation or filtration.

[25] The method for separating a recombinant protein according to any one of [21] to [24], in which aggregation of the insoluble bodies of the recombinant protein is carried out by adding one or more selected from the group consisting of a metal salt, an acid, and an anionic flocculant.

[26] A method for separating a recombinant protein, including the following steps (A) to (C):

a step (A) of disrupting a recombinant cell expressing a target recombinant protein as insoluble bodies in the cell to obtain a disrupted suspension containing the insoluble bodies of the recombinant protein;

a step (B) of adding one or more selected from the group consisting of a metal salt, an acid, and an anionic flocculant to the disrupted suspension obtained in the step (A), and aggregating the insoluble bodies of the recombinant protein to obtain a recombinant protein aggregate; and a step (C) of separating the aggregate obtained in the step (B) from the suspension.

[27] The method for separating a recombinant protein according to [26], further including heating in the step (B).

[28] The method for separating a recombinant protein according to [27], further including stirring in the step (B).

[29] The method for separating a recombinant protein according to any one of [25] to [28], in which the metal salt is a metal salt selected from the group consisting of an alkaline earth metal salt and an earth metal salt.

[30] The method for separating a recombinant protein according to [29], in which the metal salt is a metal salt selected from the group consisting of an alkaline earth metal halide, an alkaline earth metal nitrate, an alkaline earth metal sulfate, an earth metal halide, an earth metal nitrate, and an earth metal sulfate.

[31] The method for separating a recombinant protein according to any one of [25] to [30], in which the acid is an oxo acid.

[32] The method for separating a recombinant protein according to [31], in which the oxo acid is an oxo acid selected from the group consisting of acetic acid, sulfuric acid, and citric acid.

[33] The method for separating a recombinant protein according to any one of [25] to [32], in which the anionic flocculant is an anionic flocculant selected from the group consisting of a polyacrylate, an anionic polyacrylamide, and an acrylamide-acrylate copolymer.

[34] The method for separating a recombinant protein according to any one of [21] to [33], in which the disruption of the recombinant cell is mechanical disruption.

[35] The method for separating a recombinant protein according to any one of [21] and [26] to [34], in which the separation of the recombinant protein aggregate is carried out by filtration.

[36] The method for separating a recombinant protein according to any one of [21] to [35], in which the recombinant cell is a recombinant cell transformed with a host selected from the group consisting of a bacterium, a yeast, a filamentous fungus, an insect cell, a plant cell, and an animal cell.

[37] The method for separating a recombinant protein according to any one of [21] to [36], in which the recombinant protein is a structural protein.

[38] The method for separating a recombinant protein according to [37], in which the structural protein is a protein derived from a protein selected from the group consisting of keratin, collagen, elastin, resilin, silkworm silk, and spider silk.

[39] A method for producing a recombinant protein aggregate using the separation method according to any one of [1] to [38], in which the recombinant protein aggregate obtained by the separation method has a particle size of 4 μm or more and 50 μm or less as measured by an electrical sensing zone method.

Advantageous Effects of Invention

According to the method for producing a recombinant protein aggregate of the present invention, since insoluble bodies can be aggregated and enlarged, the recombinant protein aggregate can be produced by efficiently separating insoluble bodies of the recombinant protein from a recombinant cell expressing the target recombinant protein as insoluble bodies in the cell by, for example, spontaneous sedimentation, centrifugation, or filtration. Further, not only insoluble bodies or insoluble granules of the recombinant protein, which could not be readily separated by centrifugation, filtration, or the like, can be easily separated, but also the purity of the separated recombinant protein can be improved. According to the present invention, such an unexpected effect is exerted.

DESCRIPTION OF EMBODIMENTS

Figure 1:
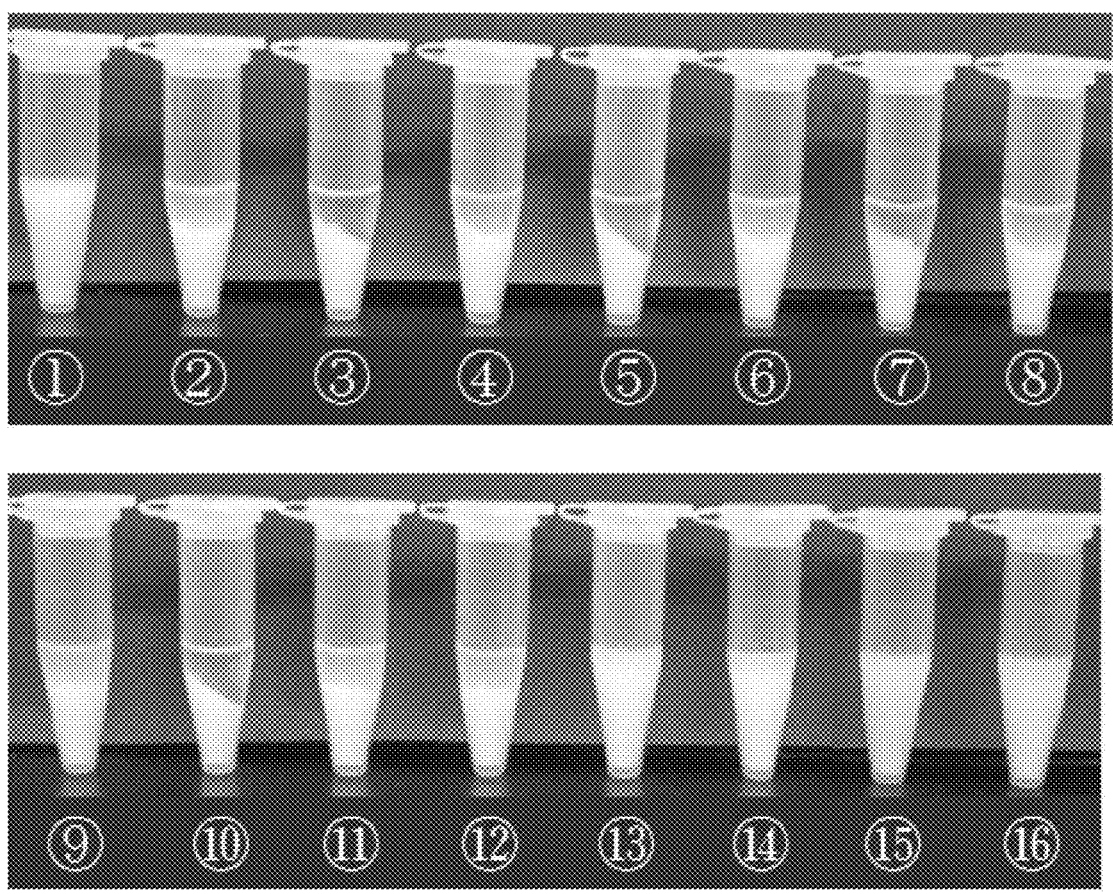
FIG. 1 is a photograph showing the results of studying an aggregation effect of insoluble bodies by adding a metal salt in Example 1.

Hereinafter, embodiments for carrying out the present invention will be described in detail. However, the present invention is not limited to the following embodiments.

The method for producing a recombinant protein aggregate according to an embodiment is a method for producing a recombinant protein aggregate by separating insoluble bodies of a recombinant protein as an aggregate from a recombinant cell expressing the recombinant protein as insoluble bodies in the cell, including disrupting the recombinant cell, aggregating the insoluble bodies of the recombinant protein, and separating the resulting aggregate. In the present production method, aggregation of insoluble bodies of the recombinant protein is preferably carried out by adding one or more selected from the group consisting of a metal salt, an acid, and an anionic flocculant.

The method for producing a recombinant protein aggregate according to another embodiment includes the following steps (A) to (C):

a step (A) of disrupting a recombinant cell expressing a target recombinant protein as insoluble bodies in the cell to obtain a disrupted suspension containing the insoluble bodies of the recombinant protein;

a step (B) of adding one or more selected from the group consisting of a metal salt, an acid, and an anionic flocculant to the disrupted suspension obtained in the step (A), and aggregating the insoluble bodies of the recombinant protein to obtain the recombinant protein aggregate; and a step (C) of separating the aggregate obtained in the step (B) from the suspension.

(Recombinant Protein)

The insoluble recombinant protein (sometimes referred to as "target protein" in the present specification) to be separated by the method for producing a recombinant protein aggregate according to the present embodiment is expressed as insoluble bodies in a recombinant cell which will be described hereinafter. The recombinant protein may be any insoluble protein which is preferably produced on an industrial scale, and examples thereof include a protein that can be used for industrial use, a protein that can be used for medical use, and a structural protein. Specific examples of the protein that can be used for industrial or medical use include an enzyme, a regulatory protein, a receptor, a peptide hormone, a cytokine, a membrane and a transport protein, an antigen used for vaccination, a vaccine, an antigen binding protein, an immunostimulatory protein, an allergen, a full-length antibody and an antibody fragment, and derivatives thereof. Specific examples of the structural protein include keratin, collagen, elastin, resilin, silkworm silk and spider silk, and proteins derived therefrom.

The protein derived from spider silk or silkworm silk which is a fibroin-like protein may be, for example, a protein containing a domain sequence represented by Formula 1: $[(A)_n \text{ motif-REP}]_m$ (in which, in Formula 1, $(A)_n$ motif represents an amino acid sequence consisting of 4 to 20 amino acid residues and the number of alanine residues to the total number of amino acid residues in the $(A)_n$ motif is 80% or more; REP represents an amino acid sequence consisting of 10 to 200 amino acid residues; m represents an integer of 8 to 300; a plurality of $(A)_n$ motifs may be the same amino acid sequence or different amino acid sequences; and a plurality of REP's may be the same amino acid sequence or different amino acid sequences). Specific examples thereof include proteins containing the amino acid sequences represented by SEQ ID NO: 1 (PRT410), SEQ ID NO: 2 (PRT853), SEQ ID NO: 3 (PRT647), SEQ ID NO: 4 (PRT699), and SEQ ID NO: 5 (PRT698). The hydropathy indices of these proteins are −0.81, −0.68, 0.04, 0.17, and 0.43, respectively. The value of the hydropathy index is a value calculated according to the method described in International Publication No. WO2014/103846.

The protein derived from collagen may be, for example, a protein containing a domain sequence represented by Formula 2: $[\text{REP2}]_o$ (in which, in Formula 2, o represents an integer of 5 to 300; REP2 represents an amino acid sequence consisting of Gly-X-Y Gly where X and Y each represent any amino acid residue other than Gly, and a plurality of REP2's may be the same amino acid sequence or different amino acid sequences). A specific example thereof may be a protein containing the amino acid sequence represented by SEQ ID NO: 6 (Collagen-type 4-Kai). The amino acid sequence represented by SEQ ID NO: 6 is an amino acid sequence in which an amino acid sequence (tag sequence and hinge sequence) represented by SEQ ID NO: 10 has been added to the N-terminus of the amino acid sequence from the 301st residue to the 540th residue corresponding to a repeat portion and a motif of a partial sequence of human collagen type 4 (NCBI GenBank Accession No.: CAA 56335.1, GI: 3702452) obtained from the NCBI database. The Collagen-type 4-Kai has a hydropathy index of −0.75.

The protein derived from resilin may be, for example, a protein containing a domain sequence represented by Formula 3: $[\text{REP3}]_p$ (in which, in Formula 3, p represents an integer of 4 to 300; REP3 represents an amino acid sequence consisting of Ser-J-J-Tyr-Gly-U-Pro where J represents any amino acid residue and is particularly preferably an amino acid residue selected from the group consisting of Asp, Ser, and Thr, and U represents any amino acid residue and is particularly preferably an amino acid residue selected from the group consisting of Pro, Ala, Thr, and Ser; and a plurality of REP3's may be the same amino acid sequence or different amino acid sequences). A specific example thereof may be a protein containing the amino acid sequence represented by SEQ ID NO: 7. The amino acid sequence represented by SEQ ID NO: 7 is an amino acid sequence in which an amino acid sequence (tag sequence and hinge sequence) represented by SEQ ID NO: 10 has been added to the N-terminus of the amino acid sequence from the 19th residue to the 321st residue of the sequence in which Thr at the 87th residue is substituted with Ser and Asn at the 95th residue is substituted with Asp, in the amino acid sequence of resilin (NCBI GenBank Accession No. NP_611157.1, GI: 24654243). The Resilin-Kai (SEQ ID NO: 7) has a hydropathy index of −1.22.

Examples of the protein derived from elastin include proteins having amino acid sequences such as NCBI GenBank Accession Nos. AAC98395 (human), I47076 (sheep), and NP786966 (bovine). Specifically, a protein containing the amino acid sequence represented by SEQ ID NO: 8 can be mentioned. The amino acid sequence represented by SEQ ID NO: 8 is an amino acid sequence in which an amino acid sequence (tag sequence and hinge sequence) represented by SEQ ID NO: 10 has been added to the N-terminus of the amino acid sequence from the 121th residue to the 390th residue of the amino acid sequence of NCBI GenBank Accession No. AAC98395. The elastin short (SEQ ID NO: 8) has a hydropathy index of 0.42.

The protein derived from keratin may be, for example, type I keratin of *Capra hircus*. A specific example thereof may be a protein containing the amino acid sequence represented by SEQ ID NO: 9 (amino acid sequence of NCBI GenBank Accession No. ACY30466). The type I keratin 26 (SEQ ID NO: 9) has a hydropathy index of −0.53.

(Recombinant Cell)

The recombinant cell in the present embodiment is a recombinant cell expressing a recombinant protein as insoluble bodies in the cell and can be obtained by a general method using genetic engineering techniques.

The recombinant cell can be obtained, for example, by transforming a host (host cell) with an expression vector having a nucleic acid sequence encoding a target protein and one or a plurality of regulatory sequences operably linked to the nucleic acid sequence.

The regulatory sequence is a sequence that controls the expression of a recombinant protein in a host (for example, a promoter, an enhancer, a ribosome binding sequence, or a transcription termination sequence), and can be appropriately selected depending on the type of the host. The type of the expression vector such as a plasmid vector, a viral vector, a cosmid vector, a fosmid vector, or an artificial chromosome vector can be appropriately selected depending on the type of the host.

Both prokaryotes and eukaryotes such as yeast, filamentous fungi, insect cells, animal cells, and plant cells can be suitably used as hosts. More preferred are bacteria, yeast, filamentous fungi, insect cells, plant cells, and animal cells. Preferred examples of prokaryotes include *Escherichia coli*,

*Bacillus subtilis, Pseudomonas, Corynebacterium*, and *Lactococcus*, among which more preferred are *Escherichia coli* cells.

An expression vector which can autonomously replicate in a host cell or can be incorporated into a chromosome of a host and which contains a promoter at a position capable of transcribing a nucleic acid encoding a target protein is suitably used as the expression vector. A ribosome binding sequence, a transcription termination sequence, or a gene sequence that controls a promoter may be included in the expression vector.

The promoter may be any inducible promoter which functions in a host cell and is capable of inducing the expression of a target protein. The inducible promoter is a promoter capable of controlling transcription due to the presence of an inducer (expression inducer), the absence of a repressor molecule, and physical factors such as an increase or decrease in temperature, osmotic pressure, or pH value.

Examples of prokaryotic hosts include microorganisms belonging to the genus *Escherichia, Brevibacillus, Serratia, Bacillus, Microbacterium, Brevibacterium, Corynebacterium* and *Pseudomonas*.

Examples of microorganisms belonging to the genus *Escherichia* include *Escherichia coli* BL21 (Novagen, Inc.), *Escherichia coli* BL21 (DE3) (Life Technologies Corporation), *Escherichia coli* BLR (DE3) (Merck KGaA), *Escherichia coli* DH1, *Escherichia coli* GI698, *Escherichia coli* HB101, *Escherichia coli* JM109, *Escherichia coli* K5 (ATCC 23506), *Escherichia coli* KY3276, *Escherichia coli* MC1000, *Escherichia coli* MG1655 (ATCC 47076), *Escherichia coli* No. 49, *Escherichia coli* Rosetta (DE3) (Novagen, Inc.), *Escherichia coli* TB1, *Escherichia coli* Tuner (Novagen, Inc.), *Escherichia coli* Tuner (DE3) (Novagen, Inc.), *Escherichia coli* W1485, *Escherichia coli* W3110 (ATCC 27325), *Escherichia coli* XL1-Blue, and *Escherichia coli* XL2-Blue.

Examples of microorganisms belonging to the genus *Brevibacillus* include *Brevibacillus agri, Brevibacillus borstelensis, Brevibacillus centrosporus, Brevibacillus formosus, Brevibacillus invocatus, Brevibacillus laterosporus, Brevibacillus limnophilus, Brevibacillus parabrevis, Brevibacillus reuszeri, Brevibacillus thermoruber, Brevibacillus brevis* 47 (FERM BP-1223), *Brevibacillus brevis* 47K (FERM BP-2308), *Brevibacillus brevis* 47-5 (FERM BP-1664), *Brevibacillus brevis* 47-5Q (JCM 8975), *Brevibacillus choshinensis* HPD31 (FERM BP-1087), *Brevibacillus choshinensis* HPD31-S (FERM BP-6623), *Brevibacillus choshinensis* HPD31-OK (FERM BP-4573), and *Brevibacillus choshinensis* SP3 strain (manufactured by Takara Bio, Inc.).

Examples of microorganisms belonging to the genus *Serratia* include *Serratia liquefacience* ATCC 14460, *Serratia entomophila, Serratia ficaria, Serratia fonticola, Serratia grimesii, Serratia proteamaculans, Serratia odorifera, Serratia plymuthica*, and *Serratia rubidaea*.

Examples of microorganisms belonging to the genus *Bacillus* include *Bacillus subtilis* and *Bacillus amyloliquefaciens*.

Examples of microorganisms belonging to the genus *Microbacterium* include *Microbacterium ammoniaphilum* ATCC 15354.

Examples of microorganisms belonging to the genus *Brevibacterium* include *Brevibacterium divaricatum* (*Corynebacterium glutamicum*) ATCC 14020, *Brevibacterium flavum* (*Corynebacterium glutamicum* ATCC 14067) ATCC 13826, ATCC 14067, *Brevibacterium immariophilum* ATCC 14068, *Brevibacterium lactofermentum* (*Corynebacterium glutamicum* ATCC 13869) ATCC 13665, ATCC 13869, *Brevibacterium roseum* ATCC 13825, *Brevibacterium saccharolyticum* ATCC 14066, *Brevibacterium tiogenitalis* ATCC 19240, *Brevibacterium album* ATCC 15111, and *Brevibacterium cerinum* ATCC 15112.

Examples of microorganisms belonging to the genus *Corynebacterium* include *Corynebacterium ammoniagenes* ATCC 6871, ATCC 6872, *Corynebacterium glutamicum* ATCC 13032, *Corynebacterium glutamicum* ATCC 14067, *Corynebacterium acetoacidophilum* ATCC 13870, *Corynebacterium•acetoglutamicum* ATCC 15806, *Corynebacterium alkanolyticum* ATCC 21511, *Corynebacterium callunae* ATCC 15991, *Corynebacterium glutamicum* ATCC 13020, ATCC 13032, ATCC 13060, *Corynebacterium lilium* ATCC 15990, *Corynebacterium melassecola* ATCC 17965, *Corynebacterium thermoaminogenes* AJ12340 (FERM BP-1539), and *Corynebacterium herculis* ATCC 13868.

Examples of microorganisms belonging to the genus *Pseudomonas* include *Pseudomonas putida, Pseudomonas fluorescens, Pseudomonas brassicacearum, Pseudomonas fulva*, and *Pseudomonas* sp. D-0110.

As a method for introducing an expression vector into the foregoing prokaryotic host cell, any method can be used as long as it introduces DNA into the host cell. Examples thereof include a method using calcium ions [Proc. Natl. Acad. Sci. USA, 69, 2110 (1972)], a protoplast method (Japanese Unexamined Patent Publication No. S63-248394), or a method described in Gene, 17, 107 (1982) or Molecular & General Genetics, 168, 111 (1979).

Transformation of microorganisms belonging to the genus *Brevibacillus* can be carried out, for example, by the method of Takahashi et al. (J. Bacteriol., 1983, 156: 1130-1134), the method of Takagi et al. (Agric. Biol. Chem., 1989, 53: 3099-3100), or the method of Okamoto et al. (Biosci. Biotechnol. Biochem., 1997, 61: 202-203).

Examples of the vector into which a nucleic acid encoding a target protein is introduced (hereinafter, simply referred to as "vector") include pBTrp2, pBTac1, and pBTac2 (all commercially available from Boehringer Mannheim GmbH), pKK233-2 (manufactured by Pharmacia Corporation), pSE280 (manufactured by Invitrogen Corporation), pGEMEX-1 (manufactured by Promega Corporation), pQE-8 (manufactured by QIAGEN Corporation), pKYP10 (Japanese Unexamined Patent Publication No. S58-110600), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene Corporation), pTrs30 [constructed from *Escherichia coli* JM109/pTrS30 (FERM BP-5407)], pTrs32 [constructed from *Escherichia coli* JM109/pTrS32 (FERM BP-5408)], pGHA2 [constructed from *Escherichia coli* IGHA2 (FERM B-400), Japanese Unexamined Patent Publication No. S60-221091], pGKA2 [constructed from *Escherichia coli* IGKA2 (FERM BP-6798), Japanese Unexamined Patent Publication No. 560-221091], pTerm2 (U.S. Pat. Nos. 4,686,191, 4,939,094, 5,160,735), pSupex, pUB110, pTP5, pC194, pEG400 [J. Bacteriol., 172, 2392 (1990)], pGEX (manufactured by Pharmacia Corporation), and pET systems (manufactured by Novagen, Inc.).

In the case where *Escherichia coli* is used as a host, pUC18, pBluescriptII, pSupex, pET22b, pCold, or the like can be mentioned as a suitable vector.

Specific examples of vectors suitable for microorganisms belonging to the genus *Brevibacillus* include pUB110 or pHY500 (Japanese Unexamined Patent Publication No. H2-31682), pNY700 (Japanese Unexamined Patent Publication No. H4-278091), pHY4831 (J. Bacteriol., 1987, 1239-1245), pNU200 (UDAKA Shigezou, Journal of the Agricultural Chemical Society of Japan, 1987, 61: 669-676), pNU100 (Appl. Microbiol. Biotechnol., 1989, 30: 75-80), pNU211 (J. Biochem., 1992, 112: 488-491), pNU211R2L5 (Japanese Unexamined Patent Publication No. 117-170984), pNH301 (Appl. Environ. Microbiol., 1992, 58: 525-531), pNH326, pNH400 (J. Bacteriol., 1995, 177: 745-749), and pHT210 (Japanese Unexamined Patent Publication No. H6-133782), pHT110R2L5 (Appl. Microbiol. Biotechnol., 1994, 42: 358-363), which are known as *Bacillus subtilis* vectors; and pNCO2 (Japanese Unexamined Patent Publication No. 2002-238569) which is a shuttle vector between *Escherichia coli* and a microorganism belonging to the genus *Brevibacillus*.

The promoter in the case where a prokaryote is used as a host is not limited as long as it functions in the host cell. Examples thereof include promoters derived from *Escherichia coli* or phage such as a tip promoter (Ptrp), a lac promoter, a PL promoter, a PR promoter, and a T7 promoter. Also, promoters artificially designed and modified, such as a promoter (Ptrp×2) in which two Ptrp are connected in series, a tac promoter, a lacT7 promoter, and a let I promoter, can also be used. It is preferable to use a plasmid in which the distance between the Shine-Dalgarno sequence, which is a ribosome binding sequence, and the initiation codon is adjusted to an appropriate distance (for example, 6 to 18 bases). In the above expression vector, a transcription termination sequence is not always necessary for the expression of the nucleic acid, but it is preferable to arrange the transcription termination sequence directly under the nucleic acid encoding the target protein.

Examples of eukaryotic hosts include yeast, filamentous fungi (mold and the like), and insect cells.

Examples of the yeast include yeasts belonging to the genus *Saccharomyces*, *Schizosaccharomyces*, *Kluyveromyces*, *Trichosporon*, *Schwanniomyces*, *Pichia*, *Candida*, *Yarrowia*, *Hansenula*, and the like. More specific examples of the yeast include *Saccharomyces cerevisiae*, *Schizosaccharomyces pombe*, *Kluyveromyces lactic*, *Kluyveromyces marxianus*, *Trichosporon pullulans*, *Schwanniomyces alluvius*, *Schwanniomyces occidentalis*, *Candida utilis*, *Pichia pastoris*, *Pichia angusta*, *Pichia methanolica*, *Pichia polymorpha*, *Pichia Yarrowia lipolytica*, and *Hansenula polymorpha*.

It is preferred that the expression vector in the case where yeast is used as a host cell usually include an origin of replication (in the case where amplification in a host is required), a selection marker for propagation of the vector in *Escherichia coli*, a promoter and a terminator for recombinant protein expression in yeast, and a selection marker for yeast.

In the case where the expression vector is a non-integrating vector, it is preferable to further include an autonomously replicating sequence (ARS). This makes it possible to improve the stability of the expression vectors in cells (Myers, A. M., et al. (1986) Gene 45: 299-310).

Examples of the vector in the case where yeast is used as a host include YEP13 (ATCC 37115), YEp24 (ATCC 37051), YCp50 (ATCC 37419), YIp, pHS19, pHS15, pA0804, pHIL3Ol, pHIL-S1, pPIC9K, pPICZα, pGAPZα, and pPICZ B.

A specific example of the promoter in the case where yeast is used as a host is not limited as long as it can be expressed in the yeast. Examples of the promoter include a promoter of glycolytic genes such as hexose kinase, a PHO5 promoter, a PGK promoter, a GAP promoter, an ADH promoter, a gal 1 promoter, a gal 10 promoter, a heat shock polypeptide promoter, an MFα1 promoter, a CUP 1 promoter, a pGAP promoter, a pGCW14 promoter, an AOX1 promoter, and an MOX promoter.

As a method for introducing an expression vector into yeast, any method can be used as long as it introduces DNA into yeast. Examples thereof include an electroporation method (Methods Enzymol., 194, 182 (1990)), a spheroplast method (Proc. Natl. Acad. Sci., USA, 81, 4889 (1984)), a lithium acetate method (J. Bacteriol., 153, 163 (1983)), and a method described in Proc. Natl. Acad. Sci. USA, 75, 1929 (1978).

Examples of filamentous fungi include fungi belonging to the genus *Acremonium*, *Aspergillus*, *Ustilago*, *Trichoderma*, *Neurospora*, *Fusarium*, *Humicola*, *Penicillium*, *Myceliophtora*, *Bobyts*, *Magnaporthe*, *Mucor*, *Metarhizium*, *Monascus*, *Rhizopus*, and *Rhizomucor*.

Specific examples of filamentous fungi include *Acremonium alabamense*, *Acremonium cellulolyticus*, *Aspergillus aculeatus*, *Aspergillus awamori*, *Aspergillus oryzae*, *Aspergillus sake*, *Aspergillus sojae*, *Aspergillus tubigensis*, *Aspergillus niger*, *Aspergillus nidulans*, *Aspergillus parasiticus*, *Aspergillus ficuum*, *Aspergillus phoenicus*, *Aspergillus foetidus*, *Aspergillus flavus*, *Aspergillus fumigatus*, *Aspergillus japonicus*, *Trichoderma viride*, *Trichoderma harzianum*, *Trichoderma reseei*, *Chrysosporium lucknowense*, *Thermoascus*, *Sporotrichum*, *Sporotrichum cellulophilum*, *Talaromyces*, *Thielavia terrestris*, *Thielavia*, *Neurospora crassa*, *Fusarium oxysporus*, *Fusarium graminearum*, *Fusarium venenatum*, *Humicola insolens*, *Penicillium chrysogenum*, *Penicillium camemberti*, *Penicillium canescens*, *Penicillium emersonii*, *Penicillium funiculosum*, *Penicillium griseoroseum*, *Penicillium purpurogenum*, *Penicillium roqueforti*, *Myceliophthora thermophilum*, *Mucor ambiguus*, *Mucor circinelloides*, *Mucor fragilis*, *Mucor hiemalis*, *Mucor inaequisporus*, *Mucor oblongiellipticus*, *Mucor racemosus*, *Mucor recurvus*, *Mucor saturninus*, *Mucor subtilissmus*, *Ogataea polymorpha*, *Phanerochaete chrysosporium*, *Rhizomucor miehei*, *Rhizomucor pusillus*, and *Rhizopus arrhizus*.

A specific example of the promoter in the case where a filamentous fungus is used as a host may be any one of a gene related to a glycolytic system, a gene related to constitutive expression, an enzyme gene related to hydrolysis, and the like. Specific examples thereof include amyB, glaA, agdA, glaB, TEF1, xynF1 tannase gene, No. 8AN, gpdA, pgkA, enoA, melO, sodM, catA, and catB.

Introduction of the expression vector into filamentous fungi can be carried out by a conventionally known method. Examples thereof include the method of Cohen et al. (calcium chloride method) [Proc. Natl. Acad. Sci. USA, 69: 2110 (1972)], a protoplast method [Mol. Gen. Genet., 168: 111 (1979)], a competent method [J. Mol. Biol., 56: 209 (1971)], and an electroporation method.

Insect cells include, for example, lepidopteran insect cells, more specifically insect cells derived from *Spodoptera frugiperda* such as Sf9 and Sf21, and insect cells derived from *Trichoplusia ni* such as High 5.

Examples of the vector in the case where an insect cell is used as a host include baculoviruses such as *Autographa californica* nuclear polyhedrosis virus which is a virus that infects insects belonging to the family Noctuidae (Baculovirus Expression Vectors, A Laboratory Manual, W. H. Freeman and Company, New York (1992)).

In the case where an insect cell is used as a host, a polypeptide can be expressed by the method described in, for example, Current Protocols in Molecular Biology, Baculovirus Expression Vectors, A Laboratory Manual, W. H. Freeman and Company, New York (1992), or Bio/Technology, 6, 47 (1988). That is, a recombinant gene transfer vector and a baculovirus are co-introduced into an insect cell to obtain a recombinant virus (expression vector) in an insect cell culture supernatant, and then the recombinant virus is further infected into an insect cell, whereby the polypeptide can be expressed. Examples of the gene transfer vector used in the above method include pVL1392, pVL1393, and pBlueBacIII (all manufactured by Invitrogen Corporation).

As a method for co-introducing a recombinant gene transfer vector and a baculovirus into an insect cell for constructing the recombinant virus, for example, a calcium phosphate method (Japanese Unexamined Patent Publication No. H2-227075), a lipofection method (Proc. Natl. Acad. Sci. USA, 84, 7413 (1987)), or the like can be mentioned.

The recombinant vector preferably further contains a selection marker gene for selecting a transformant. For example, in *Escherichia coli*, resistance genes for various drugs such as tetracycline, ampicillin, and kanamycin can be used as selection marker genes. A recessive selection marker capable of complementing a genetic mutation involved in auxotrophy can also be used. In yeast, a resistance gene for geneticin can be used as a selection marker gene, and a gene complementing a genetic mutation involved in auxotrophy, or a selection marker such as LEU2, URA3, TRP1, or HIS3 can also be used. Examples of the selection marker gene for filamentous fungi include a marker gene selected from the group consisting of niaD (Biosci. Biotechnol. Biochem., 59, 1795-1797 (1995)), argB (Enzyme Microbiol Technol, 6, 386-389, (1984)), sC (Gene, 84, 329-334, (1989)), ptrA (BiosciBiotechnol Biochem, 64, 1416-1421, (2000)), pyrG (BiochemBiophys Res Commun, 112, 284-289, (1983)), amdS (Gene, 26, 205-221, (1983)), aureobasidin resistance gene (Mol Gen Genet, 261, 290-296, (1999)), benomyl resistance gene (Proc Natl Acad Sci USA, 83, 4869-4873, (1986)) and hygromycin resistance gene (Gene, 57, 21-26, (1987)), and a leucine auxotrophy-complementing gene. Further, in the case where the host is an auxotrophic mutant strain, a wild-type gene complementing the auxotrophy can also be used as a selection marker gene.

The selection of the host transformed with the foregoing expression vector can be carried out by plaque hybridization, colony hybridization, or the like using a probe that selectively binds to the foregoing nucleic acid. As the probe, it is possible to use a probe obtained by modifying a partial DNA fragment amplified by a PCR method based on sequence information of the foregoing nucleic acid with a radioisotope or digoxigenin.

(Expression of Recombinant Protein)

In a recombinant cell transformed with the expression vector for expressing a target protein, the recombinant protein is expressed as insoluble bodies in the cell. The recombinant protein can be expressed by culturing recombinant cells in a culture medium. The method of culturing the recombinant cells in the culture medium can be carried out according to a method commonly used for culturing a host.

In the case where the host is a prokaryote such as *Escherichia coli* or a eukaryote such as yeast, any of a natural medium and a synthetic medium may be used as a culture medium as long as it contains a carbon source, a nitrogen source, inorganic salts, and the like which can be assimilated by the host and it is capable of efficiently culturing the host.

As the carbon source, any carbon source that can be assimilated by the host may be used. Examples of the carbon source that can be used include carbohydrates such as glucose, fructose, sucrose, and molasses, starch and starch hydrolyzates containing them, organic acids such as acetic acid and propionic acid, and alcohols such as ethanol and propanol.

Examples of the nitrogen source that can be used include ammonium salts of inorganic or organic acids such as ammonia, ammonium chloride, ammonium sulfate, ammonium acetate and ammonium phosphate, other nitrogen-containing compounds, peptone, meat extract, yeast extract, corn steep liquor, casein hydrolyzate, soybean cake and soybean cake hydrolyzate, various fermented bacterial cells and digested products thereof.

Examples of the inorganic salt that can be used include potassium dihydrogen phosphate, dipotassium phosphate, magnesium phosphate, magnesium sulfate, sodium chloride, ferrous sulfate, manganese sulfate, copper sulfate, and calcium carbonate.

Culture of a prokaryote such as *Escherichia coli* or a eukaryote such as yeast can be carried out under aerobic conditions such as shaking culture or deep aeration stirring culture. The culture temperature is, for example, 15° C. to 40° C. The culture time is usually 16 hours to 7 days. It is preferable to maintain the pH of the culture medium during the culture at 3.0 to 9.0. The pH of the culture medium can be adjusted using an inorganic acid, an organic acid, an alkali solution, urea, calcium carbonate, ammonia, or the like.

In addition, antibiotics such as ampicillin and tetracycline may be added to the culture medium as necessary during the culture. In the case of culturing a microorganism transformed with an expression vector using an inducible promoter as a promoter, an inducer may be added to the medium as necessary. For example, in the case of culturing a microorganism transformed with an expression vector using a lac promoter, isopropyl-β-D-thiogalactopyranoside or the like is used, and in the case of culturing a microorganism transformed with an expression vector using a trp promoter, indoleacrylic acid or the like may be added to the medium.

As a culture medium for insect cells, commonly used TNM-FH medium (manufactured by Pharmingen Inc.), Sf-900 II SFM medium (manufactured by Life Technologies Corporation), ExCell 400 and ExCell 405 (both manufactured by JRH Biosciences Inc.), Grace's Insect Medium (Nature, 195, 788 (1962)), and the like can be used.

Culture of insect cells can be carried out, for example, for a culture time of 1 to 5 days under conditions such as pH 6 to 7 of culture medium and culture temperature 25° C. to 30° C. In addition, an antibiotic such as gentamicin may be added to the culture medium as necessary during the culture.

In the case where the host is a plant cell, the transformed plant cell may be directly cultured, or it may be differentiated into a plant organ and then cultured. As the culture medium for culturing a plant cell, for example, commonly used Murashige and Skoog (MS) medium, White medium, or a medium in which a plant hormone such as auxin or cytokinin is added to these media can be used.

Culture of animal cells can be carried out, for example, for a culture time of 3 to 60 days under conditions such as pH 5 to 9 of the culture medium and culture temperature 20° C.

to 40° C. In addition, an antibiotic such as kanamycin or hygromycin may be added to the medium as necessary during the culture.

According to the foregoing method, the target protein can be expressed as insoluble bodies in a recombinant cell.

Step (A) of Disrupting Recombinant Cell

The step (A) is a step of disrupting a recombinant cell expressing a target recombinant protein as insoluble bodies in the cell to obtain a disrupted suspension containing the insoluble bodies of the recombinant protein.

Disruption of a recombinant cell can be carried out according to a known method. That is, the disruption of a recombinant cell can be carried out by cell disruption by treatment with an enzyme such as lysozyme, mutanolysin, lyticase, or zymolyase; cell disruption by contact with an organic solvent or the like; cell disruption using osmotic pressure; physical/mechanical cell disruption by a ball mill, a French press, a high pressure homogenizer, ultrasonic treatment, or the like; and a combination thereof.

For the disruption of the recombinant cell, the culture solution obtained by the above-mentioned culture can be used as such, but a suspension of the washed recombinant cells is preferably used in order to improve the purity of the recombinant protein to be obtained later.

The suspension of washed recombinant cells can be prepared by the following method. That is, the recombinant cells are separated from the culture solution by centrifugation, filtration, or the like. Considering the subsequent steps, it is preferable to wash the recombinant cells with water, and it is also preferable to further wash the recombinant cells with water after washing with a buffered aqueous solution or the like. The suspension of washed recombinant cells can be prepared by suspending the obtained recombinant cells in a solution suitable for the above disruption method so as to obtain a suitable concentration.

Alternatively, it is also possible to use a suspension obtained in such a manner that the recombinant cells obtained from the culture solution are treated with an organic solvent or the like, the soluble fraction such as protein derived from the host of the recombinant cells is removed, and then the insoluble fraction is added to a solution suitable for the above disruption method so as to obtain a suitable concentration. At this time, in the case where the bacterial cells are disrupted by treatment with an organic solvent or the like, the treatment with an organic solvent or the like (contact with an organic solvent or the like) can be regarded as the above disruption treatment. That is, after the treatment with an organic solvent or the like, the following aggregation step (B) of recombinant protein insoluble bodies can be carried out.

Examples of the suitable solution include water such as industrial water, deionized water, or reverse osmosis (RO) water, and a buffered aqueous solution. The buffered aqueous solution may be, for example, a Tris/HCl buffer solution.

The resulting disrupted suspension contains insoluble bodies of the recombinant protein. In the present specification, the term "insoluble body" refers to a protein insoluble in a solution (suspension), which may faint insoluble granules in some cases.

In addition, the disrupted suspension contains cell fragments that can be easily centrifuged, and the following aggregation step may be carried out using the suspension after removing these cell fragments.

In addition, insoluble granules in the disrupted suspension may involve impurities and may be separable by centrifugation. In such a case, centrifugation may be carried out, and the precipitate fraction containing the insoluble granules thus obtained may be resuspended in the buffered aqueous solution to proceed to the following aggregation step.

Aggregation Step (B) of Recombinant Protein Insoluble Bodies

In the step (B), one or more selected from the group consisting of a metal salt, an acid, and an anionic flocculant are added to the disrupted suspension obtained in the step (A), and the insoluble bodies of the recombinant protein are aggregated to obtain a recombinant protein aggregate. In the step (B), heating and/or stirring may be carried out as necessary.

Examples of the metal salt include an alkaline earth metal salt and an earth metal salt. Specific examples thereof include an alkaline earth metal halide, an alkaline earth metal nitrate, an alkaline earth metal sulfate, an earth metal halide, an earth metal nitrate, and an earth metal sulfate. The metal salt is preferably a divalent or higher polyvalent metal salt.

Examples of the alkaline earth metal halide include calcium chloride, magnesium chloride, magnesium bromide, calcium bromide, magnesium iodide, and calcium iodide.

Examples of the alkaline earth metal nitrate include calcium nitrate, magnesium nitrate, strontium nitrate, and barium nitrate.

Examples of the alkaline earth metal sulfate include calcium sulfate, magnesium sulfate, strontium sulfate, and barium sulfate.

Examples of the earth metal halide include aluminum trichloride and gallium trichloride.

Examples of the earth metal nitrate include aluminum nitrate and gallium nitrate.

Examples of the earth metal sulfate include aluminum sulfate and gallium sulfate.

These metal salts may be used alone or in combination of two or more thereof.

Suitable examples of the metal salt include an alkali metal halide and an alkaline earth metal halide, and specific suitable examples of the metal salt include lithium chloride and calcium chloride.

In the case where the recombinant protein forms compact insoluble granules in the disrupted suspension, the metal salt is effective even with addition of a small amount. For example, the metal salt may be added in an amount of 0.01 to 20 mM and preferably 1 to 10 mM. In the case of insoluble bodies that do not form insoluble granules or insoluble granules that take time to precipitate by centrifugation, the metal salts may be added in an amount of 2 to 50 mM and preferably 5 to 10 mM.

Any of an inorganic acid and an organic acid can be used as the acid. A suitable acid may be, for example, oxo acid.

Examples of the oxo acid of inorganic acid include sulfuric acid, nitric acid, and phosphoric acid. Examples of the oxo acid of organic acid include formic acid, acetic acid, citric acid, and tartaric acid. The oxo acid is preferably acetic acid, sulfuric acid, or citric acid, and more preferably citric acid.

In the case where the recombinant protein forms compact insoluble granules in the disrupted suspension, the acid is effective even with addition of a small amount. For example, the acid may be added in an amount of 0.01 to 20 mM, preferably 1 to 20 mM, and more preferably 5 to 20 mM. In the case of insoluble bodies that do not form insoluble granules or insoluble granules that take time to precipitate by centrifugation, the acid may be added in an amount of 2 to 50 mM and preferably 10 to 30 mM.

These acids may be used alone or in combination of two or more thereof.

In the present specification, the term "anionic flocculant" refers to a polymer flocculant (polymer) having an organic anion group. Examples of the anionic flocculant include a polyacrylate-based anionic flocculant, an anionic polyacrylamide-based anionic flocculant, and an acrylamide-acrylate copolymer-based anionic flocculant. Specific examples of the anionic flocculant include KURIFARM PA series (PA-923, PA-896, PA-895, PA-893, PA-865, PA-823, PA-813, PA-804, PA-465, PA-404, PA-402, PA-265, and the like) manufactured by Kurita Water Industries Ltd., ACCOFLOC (A-95 to A-100, A-110 to A-150, A-190, A-235 H to A-250, and the like) and SUMIFLOC (FA-40 to FA-70) manufactured by MT Aquapolymer, Inc., DIAFLOC AP series (AP335B, AP741B, AP825C, and the like) manufactured by Mitsubishi Rayon Co., Ltd., TAKIFLOC A series (A-102~A-106, A-108, A-142, and A-162) manufactured by Taki Chemical Co., Ltd., and TOGAMIFLOC (TA-089, TA-104, TA-109, TA-124, TA-144, TAE-2325, TAE-2335, TAE-2644, and the like) manufactured by Togami Electric Mfg. Co. Ltd.

Among these flocculants, there are cases where the flocculants have an action of aggregating the host cells themselves. Therefore, in the case where a flocculant is used, it is preferable to use a disrupted suspension from which the cell fragments are removed in advance. Regarding an amount of the anionic flocculant to be added, the anionic flocculant is added so that the recombinant protein becomes 0.001 to 0.1% and preferably 0.01 to 0.05% in the disrupted suspension.

Adding a metal salt, an acid, or an anionic flocculant in combination with each other rather than adding each thereof alone provides an effect by adding a low concentration.

In the aggregation step (B), one or more selected from the group consisting of a metal salt, an acid, and an anionic flocculant may be added, followed by heating so that aggregation is promoted and the aggregate becomes larger. Means for heating is not particularly limited. The heating temperature (peak temperature) is not particularly limited, but from the viewpoint of efficiently obtaining insoluble bodies or insoluble granules and from the viewpoint of killing bacterial cells, the heating temperature is, for example, 60° C. or higher, preferably 70° C. or higher, and more preferably 80° C. or higher, depending on the type of target recombinant protein. In addition, from the viewpoint of suppressing the decomposition of the target protein and improving the purity of the target protein, the heating temperature is, for example, 130° C. or lower, preferably 110° C. or lower, and more preferably 90° C. or lower, depending on the type of the target protein.

The heating time (the time for maintaining the heating temperature) is not particularly limited, but from the viewpoint of efficiently obtaining insoluble bodies or insoluble granules and from the viewpoint of killing bacterial cells, the heating time is, for example, 0.5 hours or more, preferably 1 hour or more, and more preferably 2 hours or more, depending on the type of target recombinant protein. In addition, from the viewpoint of suppressing the decomposition of the target protein and improving the working efficiency, the heating time is, for example, 15 hours or less, preferably 10 hours or less, and more preferably 5 hours or less, depending on the type of the target protein.

The heating time for obtaining insoluble bodies or insoluble granules can be greatly shortened by continuously heating the disrupted suspension. The temperature in the case of continuously heating the disrupted suspension is not particularly limited, but from the viewpoint of efficiently obtaining insoluble bodies or insoluble granules and from the viewpoint of killing bacterial cells, the heating temperature is, for example, 70° C. or higher, preferably 80° C. or higher, and more preferably 90° C. or higher, depending on the type of target recombinant protein. In addition, from the viewpoint of suppressing the decomposition of the target protein and improving the purity of the target protein, the heating temperature is, for example, 140° C. or lower, preferably 120° C. or lower, and more preferably 100° C. or lower, depending on the type of the target protein.

The heating time for obtaining insoluble bodies or insoluble granules in the case of continuously heating the disrupted suspension liquid is not particularly limited, but from the viewpoint of efficiently obtaining insoluble bodies or insoluble granules and from the viewpoint of killing the bacterial cells, the heating time is, for example, 1 second or more, preferably 10 seconds or more, and more preferably 30 seconds or more, depending on the type of target recombinant protein. In addition, from the viewpoint of suppressing the degradation of the target protein and improving the working efficiency, the heating time is, for example, 120 seconds or less, preferably 90 seconds or less, and more preferably 60 seconds or less, depending on the type of the target protein.

There is no particular limitation on the method of continuously heating the disrupted suspension, and it is sufficient that the insoluble bodies or insoluble granules can be heated to 70° C. or higher and 140° C. or lower and the temperature after heating can be held within 120 seconds. Use of a continuous liquid sterilizer or the like can be mentioned. Particularly, a continuous liquid sterilizer MINI UHT T-20 (manufactured by Powerpoint International Ltd.) can be mentioned.

In the aggregation step (B), in addition to heating, further stirring may be carried out so that the aggregate becomes larger. The stirring means is not particularly limited. The stirring speed is not particularly limited, but from the viewpoint of efficiently obtaining insoluble granules, the speed at which the aggregate of insoluble bodies in the solution does not precipitate is preferable, for example, 70 rpm or more, preferably 150 rpm or more, and more preferably 300 rpm or more. From the viewpoint of suppressing the disruption of the formed insoluble bodies, the stirring speed is 1500 rpm or less, preferably 1000 rpm or less, and more preferably 500 rpm or less. The stirring may be carried out at any time during the aggregation step (B). In the case of heating, the stirring is preferably carried out together with heating.

Step (C) of Separating Recombinant Protein Aggregate

The step (C) is a step of separating the aggregate obtained in the step (B) from the suspension. Aggregation of the recombinant protein insoluble bodies is started at the same time as the addition of one or more selected from the group consisting of a metal salt, an acid, and an anionic flocculant to the disrupted suspension, and then appropriate separation means such as spontaneous sedimentation, centrifugation, or filtration can be used to separate the aggregate. After the addition of one or more selected from the group consisting of a metal salt, an acid, and an anionic flocculant, heating and optionally further stirring promote aggregation and makes the aggregate larger, which makes separation easier.

In one example, the aggregate can be recovered by centrifugation at 2,500×g for 5 to 30 minutes. In the case where the recombinant protein forms insoluble granules which are originally centrifugeable in the disrupted suspension, one or more selected from the group consisting of a metal salt, an acid, and an anionic flocculant are added, followed by heating and optionally stirring so that the insoluble granules can be further enlarged and therefore spontaneously settled. A recombinant protein insoluble bodies which are difficult to separate by centrifugation can also be separated by centrifugation, filtration, or the like, by adding one or more selected from the group consisting of a metal salt, an acid, and an anionic flocculant, followed by heating and optionally stirring so that insoluble granules can be further enlarged.

There has been no report so far that sedimentation can be carried out with a low centrifugal force like 2,500×g in the centrifugation of insoluble granules, and a cylindrical centrifuge with a high centrifugal force of usually 12,000×g or more has been used. However, according to the present invention, an insoluble recombinant protein can be precipitated as an aggregate with a lower centrifugal force, which therefore means that a separation plate type (disk type) centrifuge and a decanter type centrifuge, such as WESTFALIA, CLARIFIER, and ALFA LAVAL, which could only be used for the separation of bacterial cells until now, furthermore for example, a basket type centrifuge can be used for separating insoluble recombinant proteins. These separation plate type and decanter type centrifuges can be a very useful means in industrial production due to having a centrifugal force of 10,000×g or less and capability of continuously separating a large amount of suspension.

In addition, in the case where the above-described aggregation step is not carried out, even large insoluble granules that can be easily sedimented by ordinary centrifugation are highly likely to cause clogging in membrane filtration, but performing this aggregation step makes it possible to easily separate those large insoluble granules by the membrane. Particularly, after one or more selected from the group consisting of a metal salt, an acid, and an anionic flocculant are added, heating and optionally stirring are carried out, so that membrane separation of those large insoluble granules becomes easier.

Further, host cell-derived impurities separable from the recombinant protein insoluble bodies can be removed by separation operation alone, and therefore the purity of the recombinant protein can be improved. In addition, in the case where the separated recombinant protein insoluble bodies are resuspended and then aggregated and separated again, the purity of the recombinant protein can be further improved.

The particle size of the recombinant protein aggregate obtained by the step (C) of separating a recombinant protein aggregate can be measured by, for example, an electrical sensing zone method. The particle size of the recombinant protein aggregate is, for example, 4 μm or more, preferably 5 μm or more, more preferably 10 μm or more, and still more preferably 15 μm or more, from the viewpoint of improving filterability. The upper limit of the particle size of the aggregate is not particularly limited, but it may be 50 μm or less, 40 μm or less, 30 or less, or 20 μm or less.

As an electrical sensing zone method, a particle size distribution measurement method according to JIS Z 8832 can be mentioned. In particular, a measurement method using a particle size analyzer CDA-1000 (Sysmex Corporation) can be mentioned.

The recombinant protein aggregate obtained by the separation can be further purified using the method described in, for example, Japanese Unexamined Patent Publication No. 2013-523665 to improve the purity thereof.

EXAMPLES

Hereinafter, the present invention will be described more specifically with reference to Examples. However, the present invention is not limited to the following Examples.

(1) Construction of Target Protein-Expressing Strain (Recombinant Cell)

GEN495, GEN971, GEN740, GEN797, and GEN796, which are nucleic acids encoding fibroins having spider silk-derived sequences having amino acid sequences represented by SEQ ID NO: 1 (PRT410), SEQ ID NO: 2 (PRT853), SEQ ID NO: 3 (PRT647), SEQ ID NO: 4 (PRT699), and SEQ ID NO: 5 (PRT698), were synthesized, respectively. To each of the nucleic acid, an NdeI site was added at the 5' end and an EcoRI site was added at the downstream of the termination codon. The hydropathy index (HI) and molecular weight of each protein are as shown in Table 1.

TABLE 1

| SEQ ID NO | Protein name | Nucleic acid name | Hydropathy index (HI) | Molecular weight (kDa) |
|---|---|---|---|---|
| 1 | PRT410 | GEN495 | −0.81 | 53.6 |
| 2 | PRT853 | GEN971 | −0.68 | 218.3 |
| 3 | PRT647 | GEN740 | 0.04 | 54.1 |
| 4 | PRT699 | GEN797 | 0.17 | 48.8 |
| 5 | PRT698 | GEN796 | 0.43 | 48.5 |

These five types of nucleic acids were each cloned into a cloning vector (pUC118). Thereafter, the same nucleic acids were each excised with restriction enzymes NdeI and EcoRI and then recombined into a protein expression vector pET-22 b(+) to obtain expression vectors. *Escherichia coli* BLR (DE3) was transformed with each of the five expression vectors to obtain transformed *Escherichia coli* (recombinant cells) expressing the target protein.

(2) Expression of Target Protein

The above transformed *Escherichia coli* was cultured in 2 mL of an LB medium containing ampicillin for 15 hours. This culture solution was added to 100 mL of a seed culture medium (Table 2) containing ampicillin so that the $OD_{600}$ was 0.005. The temperature of the culture solution was maintained at 30° C. and flask culture was carried out (about 15 hours) until the OD 600 was 5, whereby a seed culture solution was obtained.

TABLE 2

| Seed culture medium | |
|---|---|
| Reagent | Concentration (g/L) |
| Glucose | 5.0 |
| $KH_2PO_4$ | 4.0 |
| $K_2HPO_4$ | 9.3 |
| Yeast Extract | 6.0 |
| Ampicillin | 0.1 |

The seed culture solution was added to a jar fermenter to which 500 mL of a production medium (Table 3) had been added so that the $OD_{600}$ was 0.05. The culture was carried out with constant control at pH 6.9 while the temperature of the culture solution was maintained at 37° C. Further, the concentration of dissolved oxygen in the culture solution was maintained at 20% of the dissolved oxygen saturation concentration.

TABLE 3

| Production medium | |
| --- | --- |
| Reagent | Concentration (g/L) |
| Glucose | 12.0 |
| KH$_2$PO$_4$ | 9.0 |
| MgSO$_4$·7H$_2$O | 2.4 |
| Yeast Extract | 15 |
| FeSO$_4$·7H$_2$O | 0.04 |
| MnSO$_4$·5H$_2$O | 0.04 |
| CaCl$_2$·2H$_2$O | 0.04 |
| ADECANOL (Adeka Corporation, LG-295S) | 0.1 (mL/L) |

Immediately after glucose in the production medium was completely consumed, a feed solution (455 g/l L glucose, 120 g/l L yeast extract) was added at a rate of 1 mL/min. The culture was carried out with constant control at pH 6.9 while the temperature of the culture solution was maintained at 37° C. Further, the culture was carried out for 20 hours while the concentration of dissolved oxygen in the culture solution was maintained at 20% of the dissolved oxygen saturation concentration. Thereafter, 1 M isopropyl-β-thiogalactopyranoside (IPTG) was added to the culture solution at a final concentration of 1 mM to induce the expression of the target protein. Twenty hours after IPTG addition, the culture solution was centrifuged to recover the bacterial cells. SDS-PAGE was carried out using the bacterial cells prepared from the culture solution before addition of IPTG and after addition of IPTG, and it was confirmed that the target protein was expressed as insoluble bodies due to the appearance of the band of the target protein size depending on IPTG addition.

Example 1: Effect of Adding Metal Salt—Part 1

1.8 μg/g wet bacterial cells of DNase (Sigma-Aldrich Co. LLC) and 164 μg/g wet bacterial cells of Lysozyme (Thermo Fisher Scientific, Inc.) were added to an RO water suspension of *Escherichia coli* BLR(DE3) expressing PRT853 (HI: −0.68) as insoluble bodies, which was then treated four times with a high pressure homogenizer (GEA, PANDA PLUS) at room temperature at a pressure of 600 bar to disrupt the bacterial cells. After disrupting, insoluble bodies were obtained using a centrifuge (TOMY MX-305) at 11,000×g for 5 minutes. The insoluble bodies were thus relatively small insoluble granules which need to be centrifuged over a considerable amount of time to obtain. After suspending the insoluble granules in water, the metal salts shown in Table 4 were added at a concentration of 0.5 M. FIG. 1 is a photograph of each sample in the case of being centrifuged at 2,680×g for 10 seconds after addition of metal salts.

By adding a polyvalent metal salt, it was confirmed that the insoluble bodies could be precipitated by centrifugation at 2,680×g for 10 seconds.

TABLE 4

| No. | Metal salt |
| --- | --- |
| (1) | Not added |
| (2) | 0.5M sodium chloride |
| (3) | 0.5M magnesium chloride |
| (4) | 0.5M potassium chloride |
| (5) | 0.5M calcium chloride |
| (6) | 0.5M lithium chloride |
| (7) | 0.5M magnesium sulfate |
| (8) | 0.5M potassium sulfate |
| (9) | 0.5M sodium nitrate |
| (10) | 0.5M magnesium nitrate |
| (11) | 0.5M potassium nitrate |
| (12) | 0.5M lithium nitrate |
| (13) | 0.5M sodium acetate |
| (14) | 0.5M lithium acetate |
| (15) | 0.5M sodium carbonate |
| (16) | 0.5M trisodium citrate |

Example 2: Effect of Adding Metal Salt—Part 2

Figure 2:
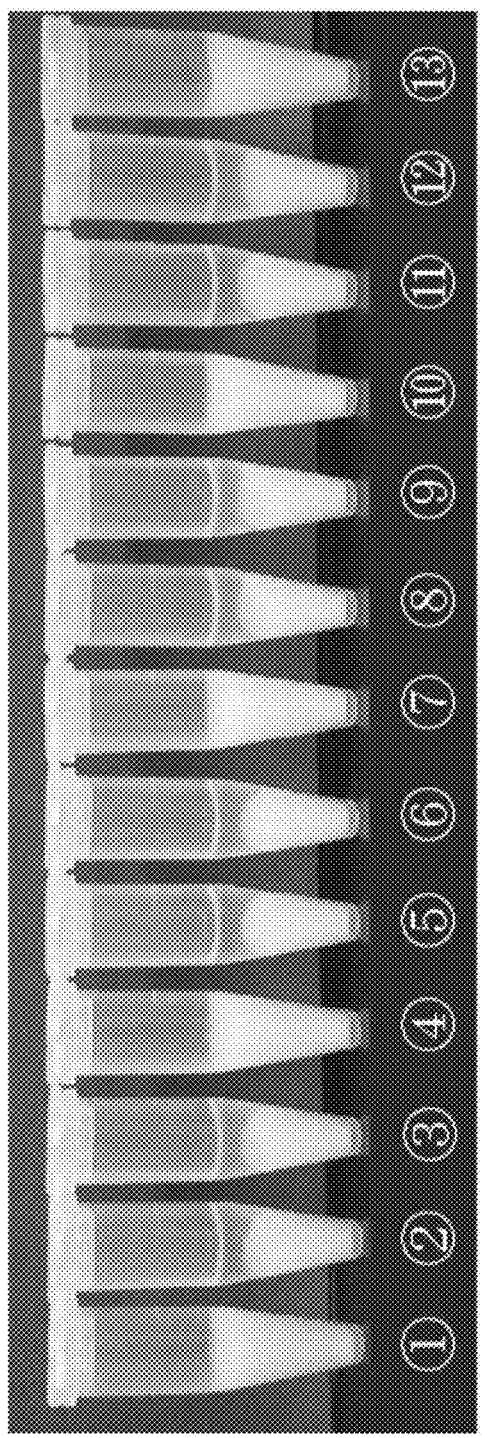
FIG. 2 is a photograph showing the results of examining the aggregation effect of the insoluble bodies by adding the metal salt in Example 2.

For the metal salts (magnesium chloride, calcium chloride, magnesium sulfate, and magnesium nitrate) having excellent aggregation effect in Example 1, the aggregation effect at low concentration was confirmed using insoluble bodies of PRT853 (see Table 5). FIG. 2 is a photograph of each sample in the case of being centrifuged at 2,680×g for 10 seconds after addition of metal salts.

Aggregation effect was observed with any metal salt at a concentration of 1 mM, but remarkable aggregation effect was observed at a concentration of 5 mM or more.

TABLE 5

| No. | Metal salt |
| --- | --- |
| (1) | Not added |
| (2) | 10 mM magnesium chloride |
| (3) | 5 mM magnesium chloride |
| (4) | 1 mM magnesium chloride |
| (5) | 10 mM calcium chloride |
| (6) | 5 mM calcium chloride |
| (7) | 1 mM calcium chloride |
| (8) | 10 mM magnesium sulfate |
| (9) | 5 mM magnesium sulfate |
| (10) | 1 mM magnesium sulfate |
| (11) | 10 mM magnesium nitrate |
| (12) | 5 mM magnesium nitrate |
| (13) | 1 mM magnesium nitrate |

Example 3: Effect in Proteins Having Different HI

The effect of adding metal salts in proteins with different hydrophobicity was confirmed. For four insoluble bodies of PRT410 (HI: −0.81), PRT647 (HI: 0.04), PRT699 (HI: 0.17), and PRT698 (HI: 0.43), the aggregation effect by addition of metal salts (calcium chloride and magnesium chloride) was confirmed in the same manner as in Example 1.

Figure 3:
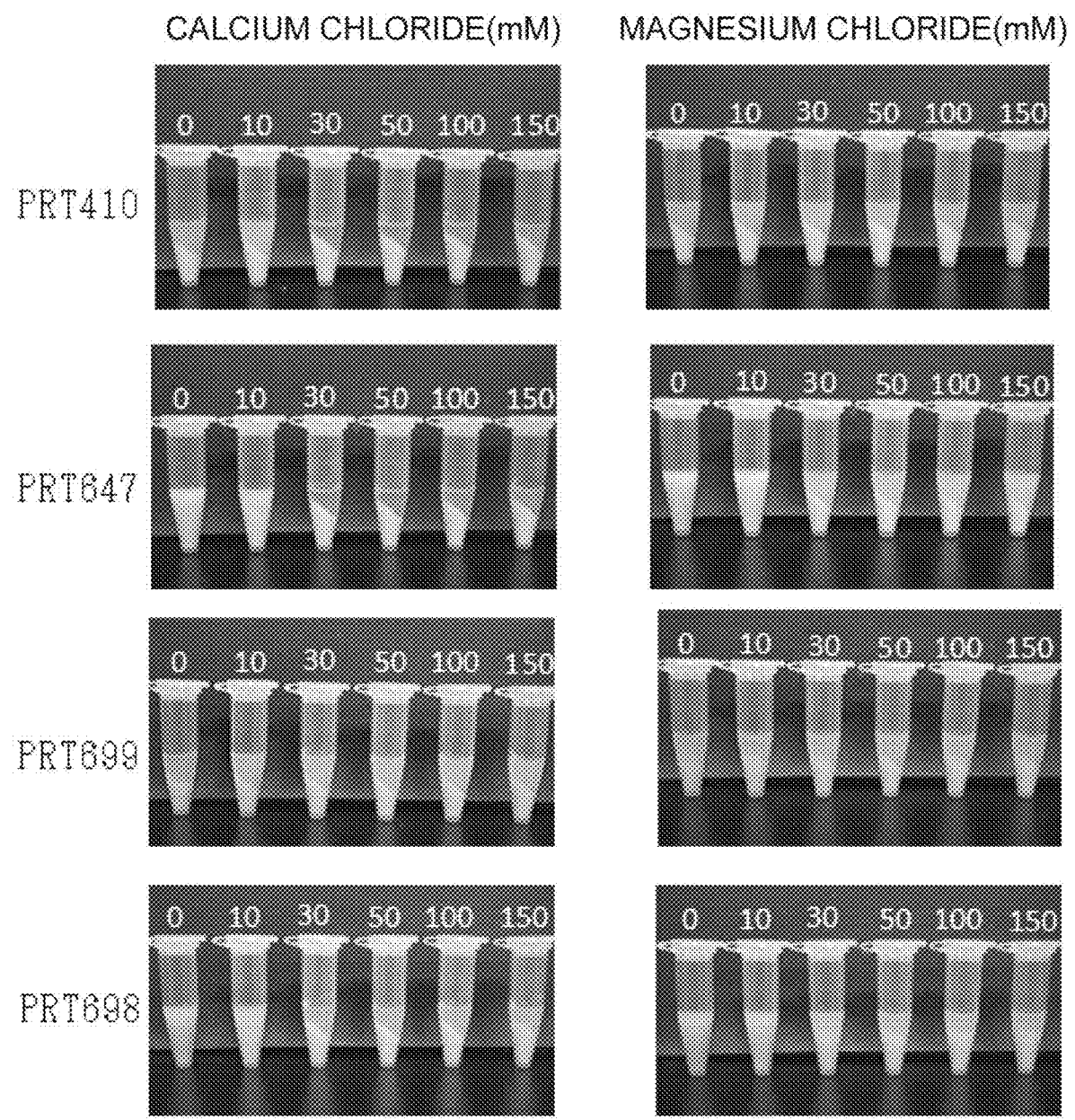
FIG. 3 is a photograph showing the results of examining the aggregation effect of insoluble bodies of proteins having different hydropathy indices by adding the metal salt in Example 3.

1.8 μg/g wet bacterial cells of DNase and 164 μg/g wet bacterial cells of Lysozyme were added to an RO water suspension of *Escherichia coli* BLR(DE3) expressing each insoluble body, which was then treated four times with a high pressure homogenizer at room temperature and at a pressure of 600 bar to disrupt the bacterial cells. After disrupting, calcium chloride or magnesium chloride was added to the disrupted suspension at a concentration of 10 to 150 mM, followed by centrifugation at 2,680×g for 10 seconds to confirm the state of aggregation. FIG. 3 is a photograph of each sample in the case of being centrifuged at 2,680×g for 10 seconds after addition of metal salts.

Through this centrifugation operation, the insoluble bodies of PRT410 and PRT699 could be precipitated without adding metal salts (calcium chloride and magnesium chloride), but it was confirmed that even a small amount could precipitate the insoluble bodies more compactly by addition of metal salts. On the other hand, PRT647 and PRT698 could not be precipitated under the present centrifugation conditions unless metal salts were added, but could be aggregated and precipitated by addition of metal salts. Particularly, the higher concentration of metal salts can result in more compact aggregation and precipitation of the insoluble bodies (see FIG. 3).

Since the addition effect of metal salts was observed in proteins with different hydrophobicity, it is considered that the present metal salt addition method can be applied to aggregation of insoluble bodies of various proteins.

Example 4: Improvement of Purification Purity

Four insoluble bodies of PRT410, PRT647, PRT699, and PRT698 could be precipitated in 5 minutes in the case of being centrifuged at 11,000×g, 20° C. The precipitate fractions obtained by centrifugation were each suspended again in RO water, and the effect of adding metal salts to the present suspensions (centrifugal resuspensions) was confirmed.

Figure 4:
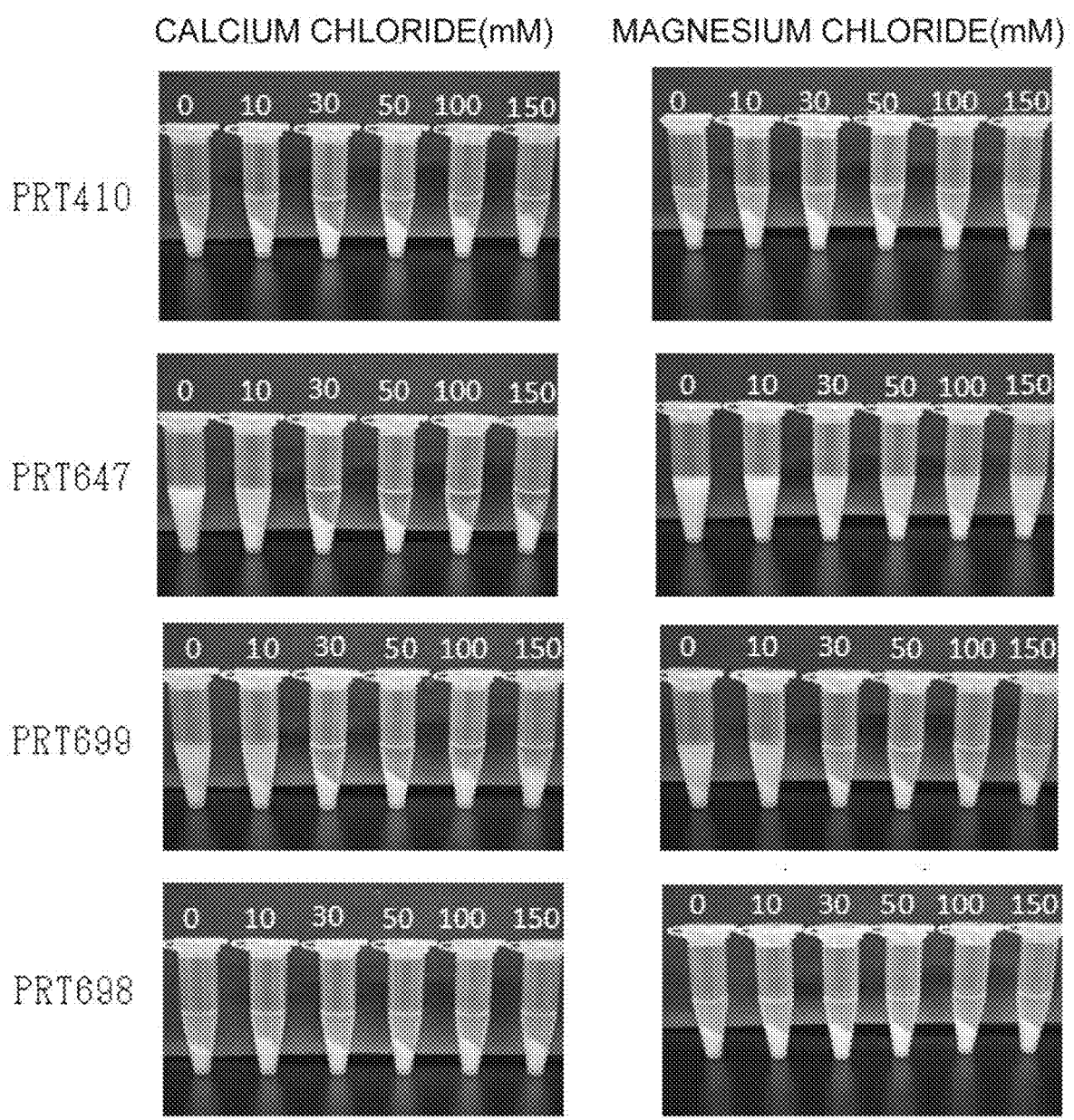
FIG. 4 is a photograph showing the results of examining the aggregation effect of insoluble bodies of proteins having different hydropathy indices by adding the metal salt in Example 4.

For the insoluble bodies resuspended in RO water, the effect of adding the metal salts was confirmed in the same manner as in Example 3. FIG. 4 is a photograph of each sample in the case of being centrifuged at 2,680×g for 10 seconds after addition of metal salts. As shown in FIG. 4, a metal salt addition effect was observed as in Example 3. In addition, as will be described below, the purity of the insoluble bodies can be improved by this resuspension.

Figure 5:
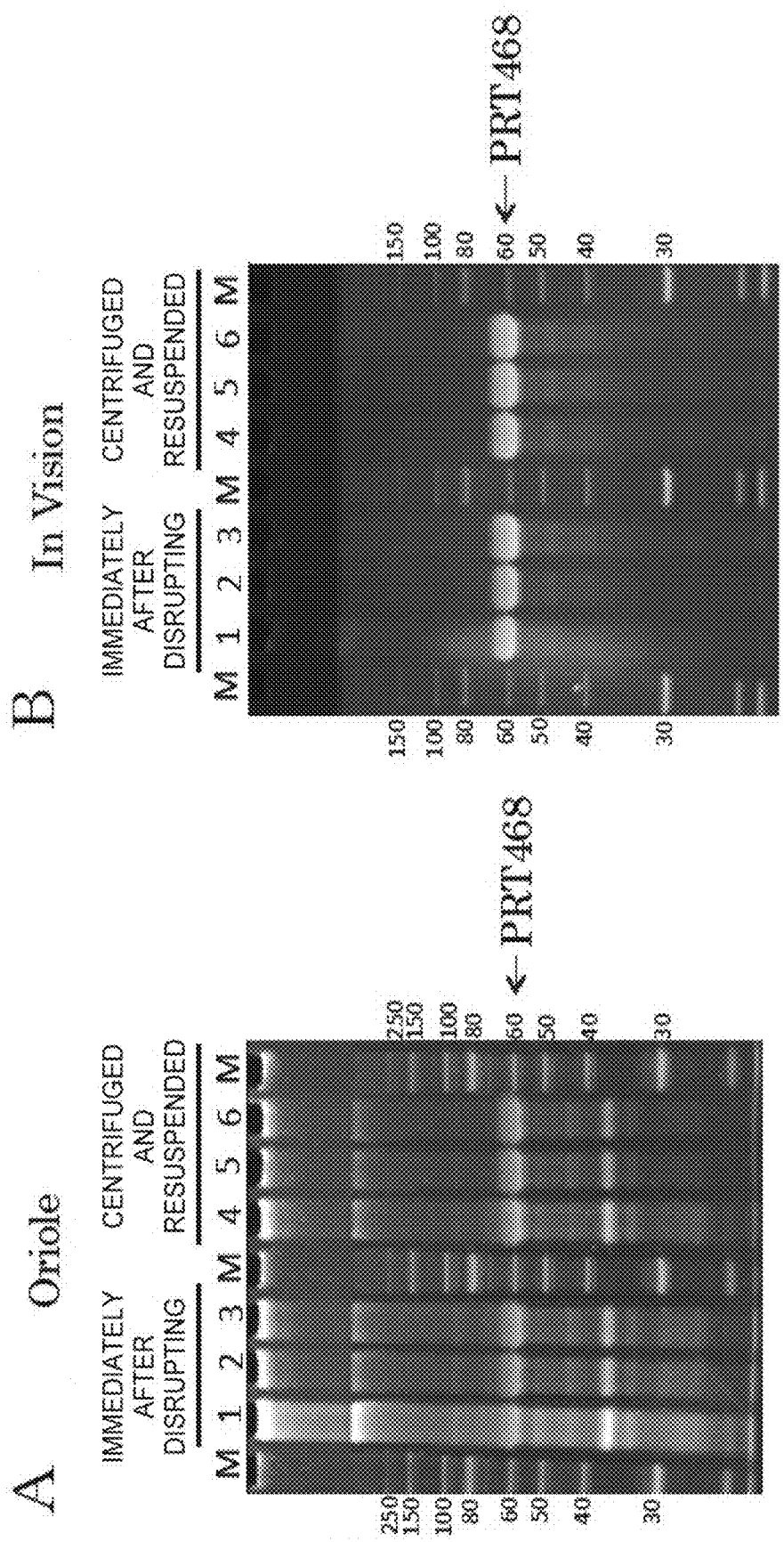
FIG. 5 is a photograph showing the results of polyacrylamide gel electrophoresis (SDS-PAGE) analysis on improvement of the purity of a target recombinant protein based on metal salt addition aggregation in Example 4. A is a photograph showing the results of staining with an Oriole (trademark) fluorescent gel stain (manufactured by Bio-Rad Laboratories, Inc.) capable of staining all proteins after the electrophoresis, and B is a photograph showing the results of staining with an InVision (trademark) His-tag In-gel Stain (manufactured by Thermo Fisher Scientific, Inc.) reacting to a His tag region of PRT410, after the electrophoresis.

FIG. 5 and Table 6 show the results of improved purity of insoluble bodies by the metal salt addition and the centrifugal resuspension operation. FIG. 5 is a photograph showing the results (electrophoresis results) of SDS-PAGE analysis of each treatment liquid of PRT410 obtained in Example 3 and Example 4. In A and B of FIG. 5, a suspension (disrupted suspension) of PRT410 immediately after disrupting the bacterial cells with a high pressure homogenizer was applied to lane 1; the precipitate fraction obtained by adding calcium chloride to the disrupted suspension at a concentration of 10 mM, followed by precipitation and centrifugation at 2,500×g for 5 minutes was applied to lane 2; the precipitate fraction obtained by adding magnesium chloride to the disrupted suspension at a concentration of 10 mM, followed by precipitation and centrifugation at 2,500×g for 5 minutes was applied to lane 3; and a molecular weight marker protein was applied to lane M.

A of FIG. 5 is a photograph showing the results of staining with an Oriole (trademark) fluorescent gel stain (manufactured by Bio-Rad Laboratories, Inc.) capable of staining all proteins after the electrophoresis, and B of FIG. 5 is a photograph showing the results of staining with an InVision (trademark) His-tag In-gel Stain (manufactured by Thermo Fisher Scientific, Inc.) reacting to a His tag region of PRT410, after the electrophoresis. PRT410 with a theoretical molecular weight of 53.6 kDa was detected as a band near the molecular weight marker of 60 kDa.

Using the Gel Doc (trademark) EZ Gel Imager (manufactured by Bio-Rad Laboratories, Inc.), the electrophoretic band of Oriole-stained gel was analyzed to calculate the purified purity of PRT410 in each treatment liquid. The results are shown in Table 6 (immediately after disrupting).

The purity of the precipitate fraction obtained without adding metal salts was 10.5%, but since more compact aggregation and precipitation could be made by addition of metal salts, the purity could be improved up to 30.7% by adding calcium chloride and 34.1% by adding magnesium chloride (see lanes 1 to 3 in FIG. 5, and Table 6 (immediately after disrupting)).

Further, in A and B of FIG. 5, a suspension (centrifugal resuspension) obtained by precipitating the disrupted suspension (lane 1) by centrifugation at 11,000×g at 20° C. for 5 minutes, and suspending the resulting precipitate fraction again in RO water was applied to lane 4; the precipitate fraction obtained by adding calcium chloride to the centrifugal resuspension at a concentration of 10 mM, followed by low speed centrifugation at 2,500×g for 5 minutes was applied to lane 5; and the precipitate fraction obtained by adding magnesium chloride to the centrifugal resuspension at a concentration of 10 mM, followed by low speed centrifugation at 2,500×g for 5 minutes was applied to lane 6. The purity could be improved from 10.5% to 34.8% (see lane 4 in FIG. 5, and Table 6 (centrifuged and resuspended)) by precipitating the suspension immediately after disrupting the bacterial cells with a high pressure homogenizer by centrifugation at 11,000×g at 20° C. for 5 minutes, and resuspending the resulting precipitate fraction again in RO water (centrifugal resuspension), but by adding calcium chloride or magnesium chloride to the centrifugal resuspension at a concentration of 10 mM, and aggregating the insoluble bodies, the separation could be made by low speed centrifugation at 2,500×g for 5 minutes, and the purity of the resulting precipitate fraction was improved to 48.6% and 50.1%, respectively (see lanes 5 and 6 in FIG. 5, and Table 6 (centrifuged and resuspended)). It was thus possible to significantly improve the purity by adding metal salts.

It was confirmed that this metal salt addition method is not only effective for aggregation of insoluble bodies and is but also an effective means for removal of impurities derived from host cells.

TABLE 6

| | Purity (%) | | |
|---|---|---|---|
| | Not added | 10 mM calcium chloride | 10 mM magnesium chloride |
| Immediately after disrupting | 10.5 | 30.7 | 34.1 |
| Centrifuged and resuspended | 34.8 | 48.6 | 50.1 |

In addition, 50 mM metal salt was added to each of the centrifugal resuspensions and disrupted suspensions of four insoluble bodies of PRT410, PRT647, PRT699, and PRT698, followed by aggregation and centrifugation at 2,680×g for 10 seconds. For the precipitate fraction obtained in each case, the recovery rate of the protein was determined. The results are shown in Table 7.

The recovery rate was calculated by measuring the absorbance at 595 nm with a microplate reader (TECAN, Infinite F200), assuming that the numerical value of the absorbance before centrifugation is 0% and the numerical value of the absorbance of the supernatant after treatment of 11,000×g for 10 minutes is 100%.

TABLE 7

| | Recovery rate (%) | | |
|---|---|---|---|
| Protein name | Not added | 50 mM calcium chloride | 50 mM magnesium chloride |
| PRT410 | 18 | 98 | 97 |
| PRT647 | 0 | 100 | 97 |
| PRT699 | 15 | 99 | 98 |
| PRT698 | 2 | 97 | 94 |

As is apparent from Table 7, insoluble bodies could be recovered with very high yield by adding metal salts.

It was confirmed that this metal salt addition method is not limited to the type of protein as long as it is an insoluble protein, is a very effective means for aggregation of insoluble bodies and removal of impurities derived from host cells, irrespective of whether the form of insoluble body is a compact insoluble granule or not, and is also an excellent method capable of recovering insoluble bodies with very high yield.

Example 5: Effect of Adding Acid—Part 1

1.8 µg/g wet bacterial cells of DNase (Sigma-Aldrich Co. LLC) and 164 µg/g wet bacterial cells of Lysozyme (Thermo Fisher Scientific, Inc.) were added to an RO water suspension of *Escherichia coli* BLR(DE3) expressing PRT853 (HI: −0.68) as insoluble bodies, which was then treated four times with a high pressure homogenizer (GEA, PANDA PLUS) at room temperature at a pressure of 600 bar to obtain a disrupted suspension of the bacterial cells.

Figure 6:
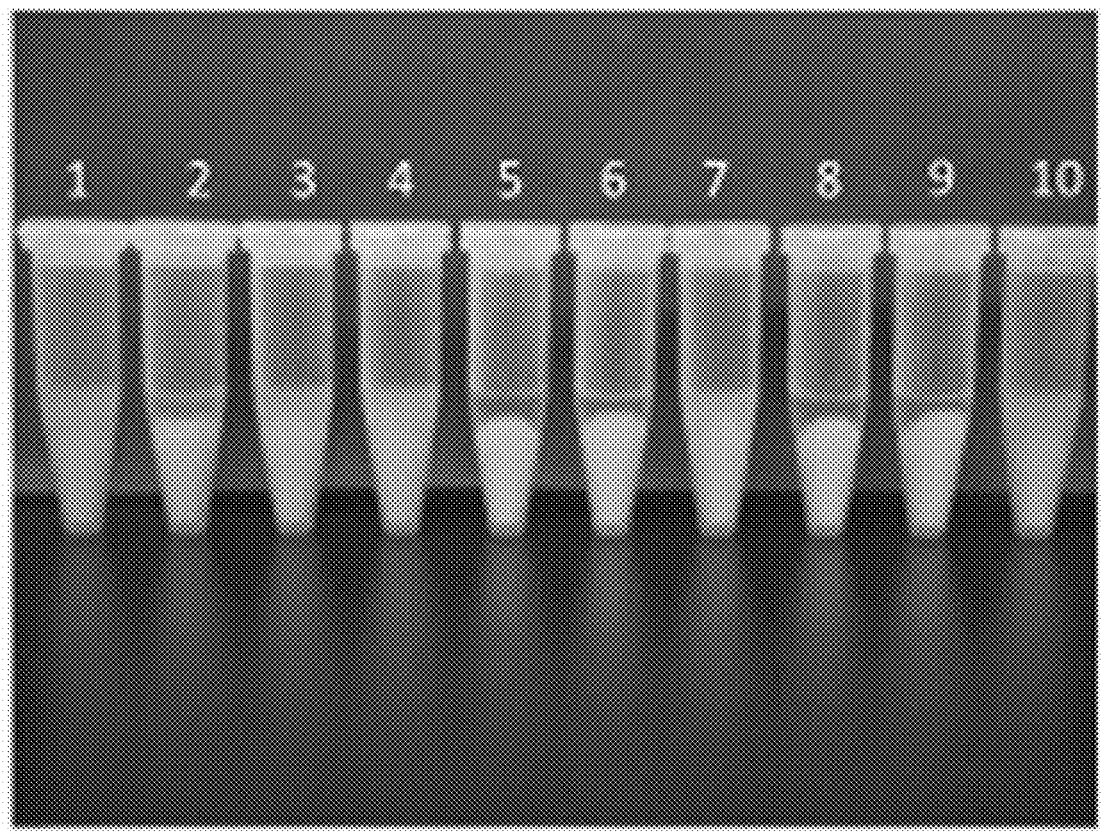
FIG. 6 is a photograph showing the results of examining the aggregation effect of insoluble bodies by adding an acid in Example 5.

Acetic acid, citric acid, or sulfuric acid was added to the disrupted suspension at a concentration of 10 to 100 mM (for the relationship between sample number and acid concentration, see Table 8), followed by centrifugation at 2,500×g for 30 seconds to confirm the state of aggregation of insoluble bodies. FIG. 6 is a photograph of each sample after centrifugation. With no addition of an acid (Sample 1), insoluble bodies could not be precipitated and obtained under these low speed centrifugation conditions. However, with addition of an acid, an aggregate of insoluble bodies could be obtained under these low speed centrifugation conditions, even at any concentration of the acid shown in Table 8 (Samples 2 to 10).

Figure 7:
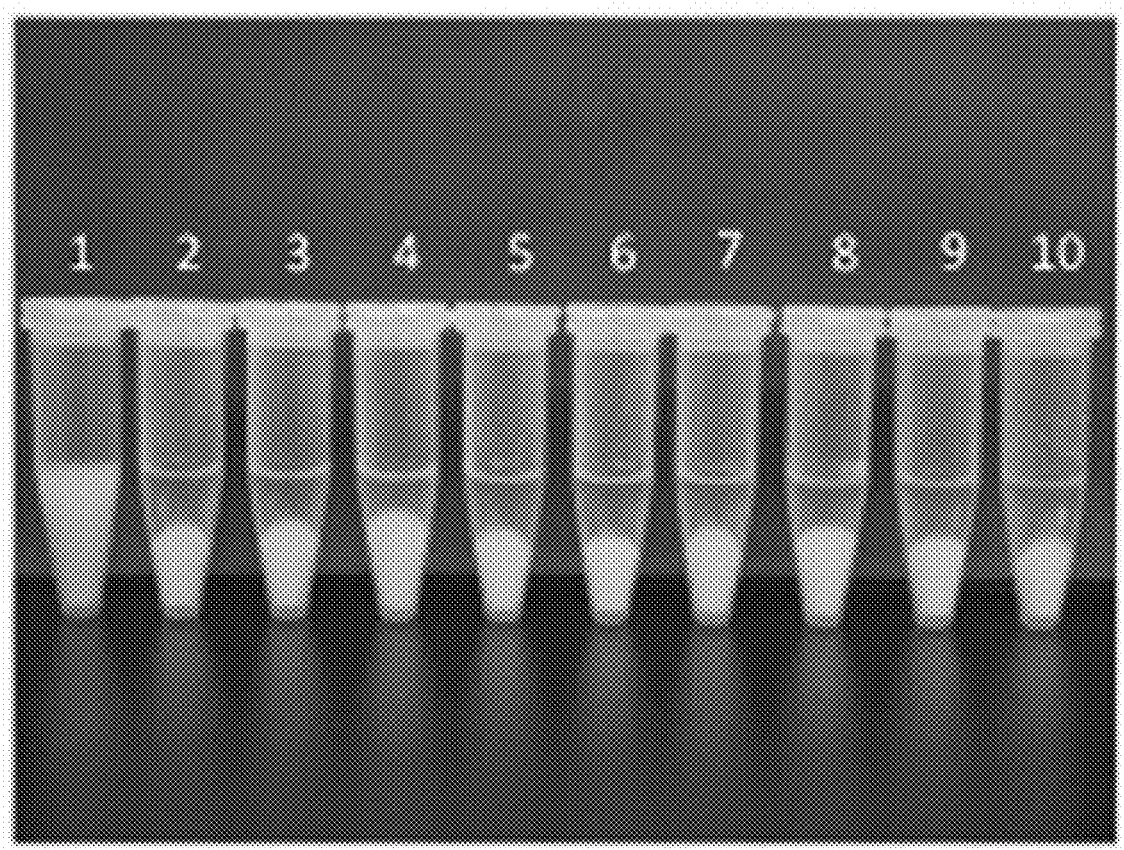
FIG. 7 is a photograph showing the results of examining the aggregation effect of insoluble bodies by adding an acid in the insoluble bodies after washing in Example 5.

The effect of adding an acid in the insoluble bodies after resuspension in RO water (centrifugal resuspension) was also examined. That is, the disrupted suspension of the bacterial cells was treated with a centrifuge (TOMY MX-305) at 11,000×g for 5 minutes to obtain insoluble bodies. Such insoluble bodies are thus relatively small insoluble granules which need to be centrifuged at considerable centrifugal force and time in order to obtain without adding an acid. After suspending the insoluble bodies in RO water (centrifugal resuspension), an acid having the concentration shown in Table 8 was added as above, followed by centrifugation at 2,500×g for 30 seconds to confine the state of aggregation of insoluble bodies. FIG. 7 is a photograph of each sample after centrifugation. It was confirmed that, even in the centrifugal resuspension resuspended in RO water, aggregation of insoluble bodies can be effectively achieved with an acid. In addition, as a result of resuspension in RO water, the granules are washed and therefore the medium and components derived from the bacterial cells are removed, so that it was possible to obtain pure insoluble bodies even in the eyes, as compared with the insoluble bodies which were not resuspended in RO water.

TABLE 8

| No. | Acid |
|---|---|
| 1 | Not added |
| 2 | 0.10M acetic acid |
| 3 | 0.05M acetic acid |
| 4 | 0.01M acetic acid |
| 5 | 0.10M citric acid |
| 6 | 0.05M citric acid |
| 7 | 0.01M citric acid |
| 8 | 0.10M sulfuric acid |
| 9 | 0.05M sulfuric acid |
| 10 | 0.01M sulfuric acid |

Example 6: Effect of Adding Acid in Proteins Having Different HI

For four insoluble bodies of PRT410 (HI: −0.81), PRT647 (HI: 0.04), PRT699 (HI: 0.17), and PRT698 (HI: 0.43) with different hydrophobicity, in the same manner as in Example 5, 5 to 30 mM citric acid was added and the aggregation effect of the insoluble bodies was confirmed as follows.

Figure 8:
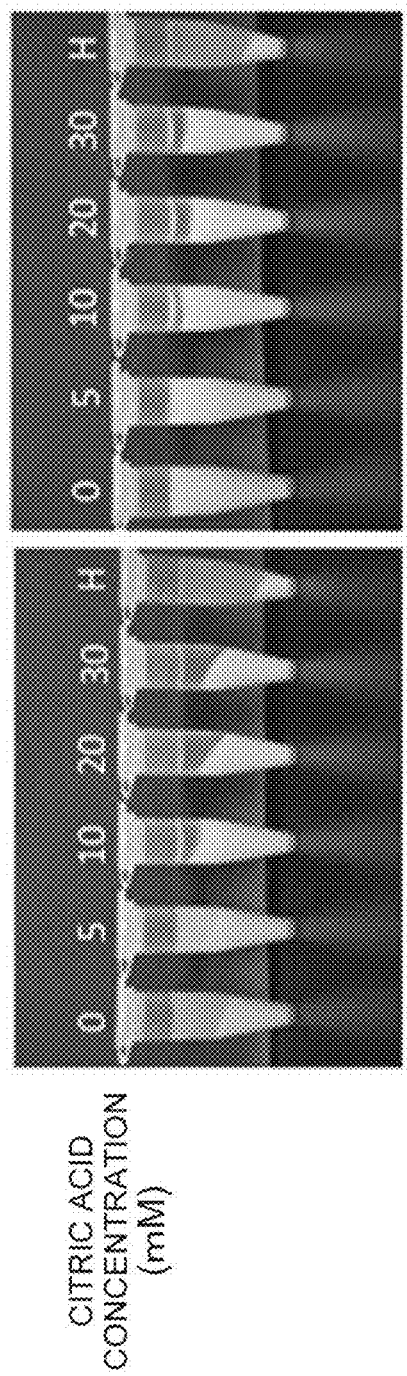
FIG. 8 is a photograph showing the results of examining the aggregation effect of insoluble bodies of proteins having different hydropathy indices by adding an acid in Example 6.
Figure 8:
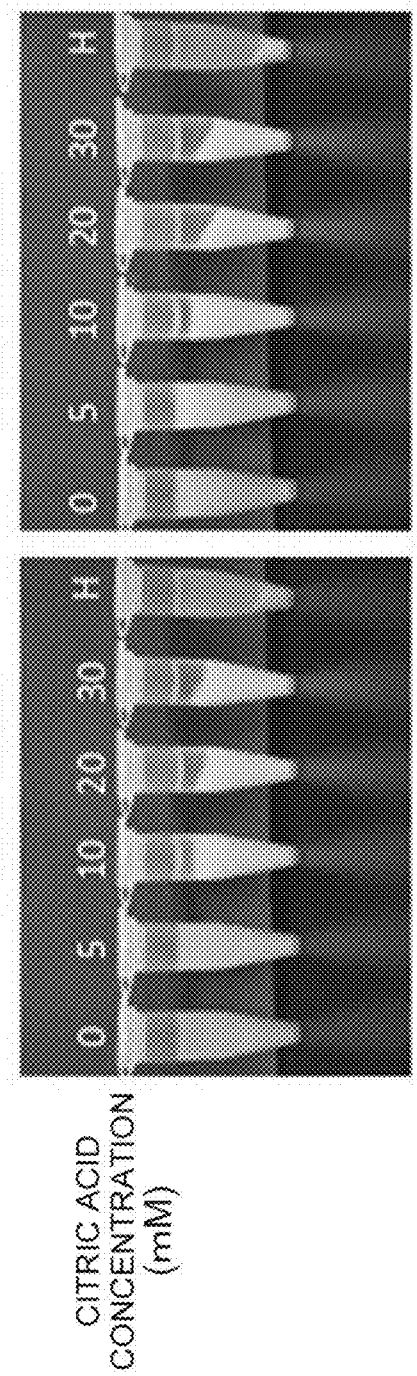

1.8 µg/g wet bacterial cells of DNase and 164 µg/g wet bacterial cells of Lysozyme were added to the RO water suspension of *Escherichia coli* BLR(DE3) expressing each insoluble body, which was then treated four times with a high pressure homogenizer at room temperature and at a pressure of 600 bar to disrupt the bacterial cells. After disrupting, citric acid was added to the disrupted suspension at a concentration of 5 to 30 mM, followed by centrifugation at 2,500×g for 30 seconds to confirm the state of aggregation. FIG. 8 is a photograph of each sample after centrifugation.

In FIG. 8, 0, 5, 10, 20, and 30 indicate the concentration (mM) of citric acid added (0 mM: citric acid not added). H is a sample obtained by centrifuging a suspension with no addition of citric acid at 11,000×g for 5 minutes.

The insoluble bodies of any protein could not be obtained unless the centrifugation conditions were 11,000×g for 5 minutes, in the case where an acid was not added, but insoluble bodies could be obtained by low speed centrifugation in any protein by adding citric acid of 10 mM or more. Aggregation was also observed with the addition of 5 mM citric acid, but sedimentation was incomplete in a short time of 30 seconds (see FIG. 8).

Since the acid addition effect was observed in proteins with different hydrophobicity, it is considered that this acid addition method can be applied to aggregation of insoluble bodies of various proteins.

For each of the four precipitate fractions of PRT410, PRT647, PRT699, and PRT698 recovered by low speed centrifugation, following addition of 10 mM citric acid, the protein recovery rate was determined in the same manner as in Example 4. The results are shown in Table 9.

TABLE 9

| Protein | Recovery rate (%) |
|---|---|
| PRT410 | 101 |
| PRT647 | 103 |
| PRT699 | 104 |
| PRT698 | 103 |

As is apparent from Table 9, insoluble bodies could be recovered without loss by addition of acid in any protein.

Figure 9:
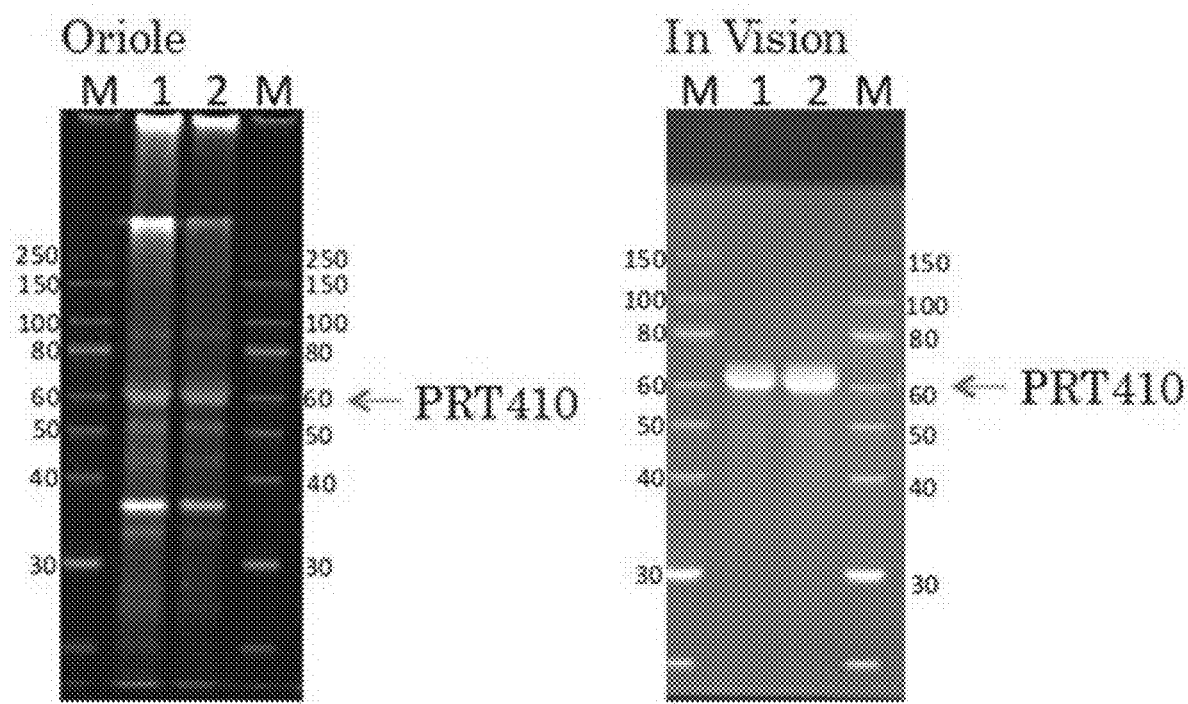
FIG. 9 is a photograph showing the results of SDS-PAGE analysis on improvement of the purity of a target recombinant protein based on acid addition aggregation in Example 6.

Next, the purity of the recovered PRT410 insoluble bodies was analyzed by SDS-PAGE. FIG. 9 is a photograph showing the results (electrophoresis results) of SDS-PAGE analysis of each treatment liquid of PRT410. In FIG. 9, a molecular weight marker protein was applied to lane M; the disrupted suspension without addition of an acid was applied to lane 1; and insoluble bodies recovered following addition of 10 mM citric acid to the disrupted suspension were applied to lane 2 so that the protein concentration would be each 1.5 µg. For the staining after electrophoresis, two staining reagents of Oriole™ fluorescent gel stain (manufactured by Bio-Rad Laboratories, Inc.) capable of staining all proteins and InVision™ His-tag In-gel Stain (manufactured by Thermo Fisher Scientific, Inc.) which reacts with the His tag region of PRT410 were used. PRT410 with a theoretical molecular weight of 53.6 kDa was detected as a band near the molecular weight marker of 60 kDa.

Using the Gel Doc (trademark) EZ Gel Imager (manufactured by Bio-Rad Laboratories, Inc.), the electrophoretic band of Oriole-stained gel was analyzed to calculate the purified purity of PRT410 in each treatment liquid. The results are shown in Table 10.

TABLE 10

| Not added (%) | 10 mM citric acid (%) |
|---|---|
| 11.6 | 23.7 |

The purity of the precipitate fraction obtained without adding an acid was 11.6%, but since compact aggregation and precipitation could be made by addition of an acid, the purity could be improved up to 23.7% (see FIG. 9).

It was confirmed that this acid addition method is not only very effective for aggregation of insoluble bodies, but also an effective means for removal of impurities derived from host cells.

It was confirmed that this acid addition method is not limited to the type of protein as long as it is an insoluble protein, is a very effective means for aggregation of insoluble bodies and removal of impurities derived from host cells, irrespective of whether the form of insoluble body is a compact insoluble granule or not, and is also an excellent method capable of recovering insoluble bodies with very high yield.

Example 7: Effect of Removing Lipopolysaccharide (LPS)

*Escherichia coli* used as a host cell has LPS called a cell wall-derived endotoxin unique to Gram-negative bacteria. In the case where the endotoxin is present in excess, it is known to have effects such as fever, multiple organ failure, and tachycardia. It is thus preferable to reduce the endotoxin. The LPS content in the insoluble bodies aggregated by the metal salt or acid addition of the present invention was measured to confirm the effect of reducing LPS.

Insoluble bodies (1) not subjected to the metal salt or acid addition were obtained by the following method.

That is, 1.8 µg/g wet bacterial cells of DNase (Sigma-Aldrich Co. LLC) and 164 µg/g wet bacterial cells of Lysozyme (Thermo Fisher Scientific, Inc.) were added to the RO water suspension of *Escherichia coli* BLR(DE3) expressing PRT853, which was then treated four times with a high pressure homogenizer (GEA, PANDA PLUS) at room temperature and at a pressure of 600 bar to disrupt the bacterial cells. Disruption was followed by treatment with a centrifuge (TOMY MX-305) at 11,000×g for 20 minutes. The precipitate fraction was suspended again in RO water and treated at 11,000×g for 30 minutes. This washing operation was carried out twice. The resulting precipitate fraction was suspended again in RO water and treated at 11,000×g for 60 minutes to obtain insoluble bodies (1) as a precipitate fraction. The insoluble bodies (1) were obtained at 20° C.

The insoluble bodies (2) aggregated by addition of a metal salt were obtained by the following method.

That is, the treatment was carried out four times with a high pressure homogenizer, and until the bacterial cells were disrupted, the same procedure as above was carried out. After disrupting, 10 mM calcium chloride was added to aggregate the insoluble bodies which were then treated at 2,500×g for 10 minutes. The resulting precipitate fraction was suspended again in RO water and treated at 2,500×g for 10 minutes. This washing operation was carried out twice to obtain insoluble bodies (2) by addition of a metal salt as a precipitate fraction.

The insoluble bodies (3) aggregated by adding an acid were obtained by the following method.

That is, insoluble bodies (3) by addition of an acid were obtained in the same manner as in obtaining the insoluble bodies (2) with addition of a metal salt, except that 10 mM citric acid was added instead of adding a metal salt.

The LPS content in these three types of insoluble bodies was measured by the following method.

(A) Preparation of Measuring Sample

About 75 mg (insoluble bodies (1): 75.5 mg, insoluble bodies (2): 75.1 mg, and insoluble bodies (3): 75.0 mg) of each of the above three types of insoluble body samples was weighed and distilled water for injection (Otsuka Pharmaceutical Factory, Inc.) was added thereto at a concentration of 50 mg/mL to prepare a suspension. After stirring with a vortex mixer, the pH was checked, and a 5 N sodium hydroxide aqueous solution (Wako Pure Chemical Industries, Ltd.) was added to adjust to neutrality. The insoluble body sample was heat-treated at 90° C. for 20 minutes using a block heater. After heat release, centrifugation was carried out at 10,000 rpm for 10 minutes, and the supernatant was recovered and used as a measurement stock solution.

(A) Measurement of LPS Content

Using a Limulus ES-il single test Wako (Wako Pure Chemical Industries, Ltd.) according to the attached explanatory material, a turbidimetric time analysis using a toxinometer (ET-6000/J, Wako Pure Chemical Industries, Ltd.) was carried out. For the measurement, CSE (*E. coli* UKT-B) attached to the kit was used as a standard endotoxin. For each specimen, firstly, the measurement stock solution was diluted 1,000-fold and measured. The measured values were obtained by 1,000-fold dilution for the insoluble bodies (1) and the insoluble bodies (2), but since the insoluble bodies (3) were below the detection limit (<0.01 EU/mL), the measured value could be obtained at 10-fold dilution by changing the dilution ratio. The results are shown in Table 11.

TABLE 11

| Sample | LPS content (µg/g) |
| --- | --- |
| Insoluble bodies (1) | 3.10 |
| Insoluble bodies (2) | 1.19 |
| Insoluble bodies (3) | 0.008 |

It was confirmed that the LPS content was reduced in the insoluble bodies (2) and (3) aggregated by adding a metal salt or an acid, as compared with the insoluble bodies (1) obtained without adding a metal salt or an acid. In particular, the LPS content was very low in the insoluble bodies (3) obtained by aggregation with an acid. The method of aggregating and obtaining insoluble bodies by adding a metal salt or an acid was an excellent method capable of also reducing the LPS content.

Figure 10:
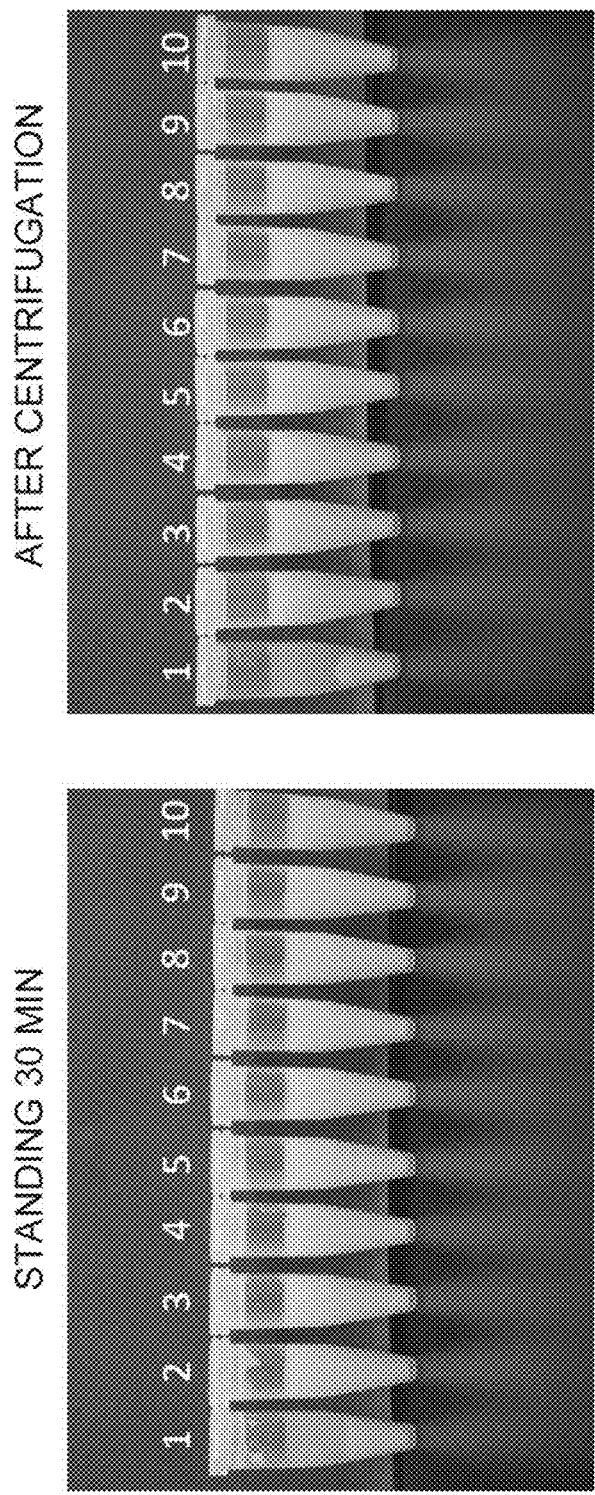
FIG. 10 is a photograph showing the results of examining the aggregation effect of insoluble bodies by adding a flocculant in Example 8.

Example 8: Aggregation Effect by Anionic Flocculant 1.8 µg/g wet bacterial cells of DNase and 164 µg/g wet bacterial cells of Lysozyme were added to an RO water suspension of *Escherichia coli* BLR(DE3) expressing PRT853 (HI: −0.68) as insoluble granules, which was then treated four times with a high pressure homogenizer at room temperature at a pressure of 600 bar to disrupt the bacterial cells to obtain a disrupted suspension. After disrupting, the flocculant shown in Table 12 was added to the disrupted suspension at a concentration of 0.05%, and the sedimentation state of the insoluble granules was confirmed by standing still or centrifugation (2,680×g for 10 seconds). The results are shown in FIG. 10.

Only an anionic polyacrylate-based flocculant (KURIFARM PA-896) was able to effectively precipitate the insoluble granules in both static and centrifugal separations.

TABLE 12

| No. | Flocculant |
| --- | --- |
| 1 | KURIFARM PA-896 (anionic flocculant) |
| 2 | KURIFARM PN-901 (nonionic flocculant) |
| 3 | KURIFARM PC-601 (cationic flocculant) |
| 4 | KURIFARM PC-668 (cationic flocculant) |

TABLE 12-continued

| No. | Flocculant |
| --- | --- |
| 5 | KURIFARM PC-696 (cationic flocculant) |
| 6 | KURIFARM PC-702 (cationic flocculant) |
| 7 | KURIFARM PC-797 (cationic flocculant) |
| 8 | KURIFUTURE PF-512 (amphoteric flocculant) |
| 9 | KURIFUTURE PF-833 (amphoteric flocculant) |
| 10 | PRESS AID111 (cationic flocculant) |

Example 9: Effect of Improving Purity by Anionic Flocculant

The effect of adding the anionic flocculant KURIFARM PA-896, whose aggregation effect was confirmed in Example 8, to the disrupted suspension and the centrifugal resuspension of the bacterial cells was confirmed. This centrifugal resuspension is a suspension in which the disrupted suspension is centrifuged at 11,000×g at 20° C. for 5 minutes and the resulting precipitate fraction is resuspended again in RO water. A disrupted suspension of the bacterial cells was obtained in the same manner as in Example 8, except that *Escherichia coli* BLR(DE3) expressing PRT410 (HI: −0.81) as insoluble granules was used.

Figure 11:
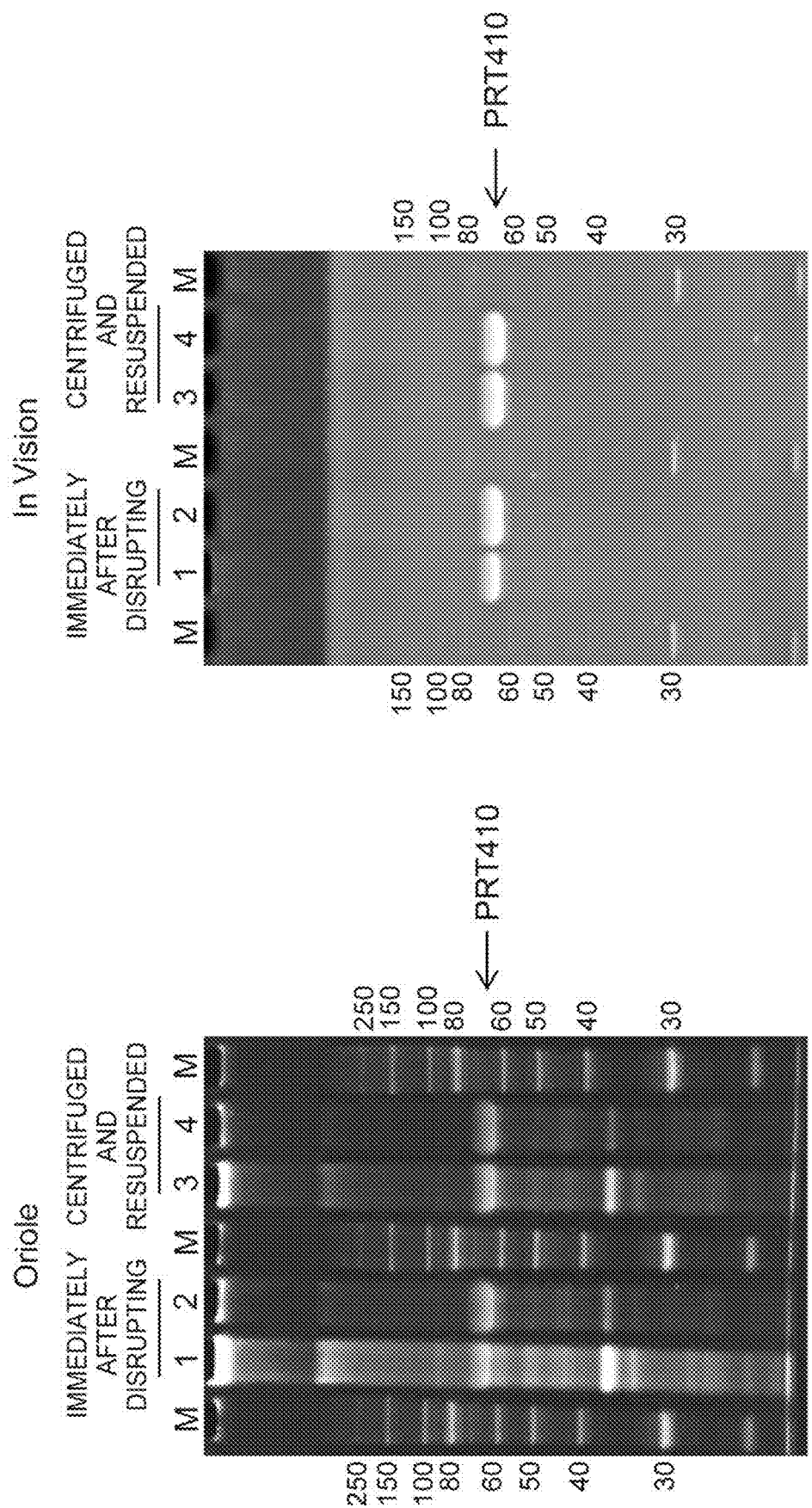
FIG. 11 is a photograph showing the results of SDS-PAGE analysis on improvement of the purity of a target recombinant protein based on anionic flocculant addition aggregation in Example 9.

After addition of the flocculant, centrifugation was carried out at 2,500×g for 5 minutes, and the purity of the insoluble bodies in the resulting precipitate fraction was analyzed by SDS-PAGE. The results are shown in FIG. 11. In FIG. 11, a suspension (disrupted suspension) of PRT410 immediately after disrupting the bacterial cells with a high pressure homogenizer was applied to lane 1; the precipitate fraction obtained by adding KURIFARM PA-896 to the disrupted suspension at a concentration of 0.01%, followed by precipitation and centrifugation at 2,500×g for 5 minutes was applied to lane 2; a suspension (centrifugal resuspension) obtained by precipitating the disrupted suspension (lane 1) by centrifugation at 11,000×g at 20° C. for 5 minutes, and suspending the resulting precipitate fraction again in RO water was applied to lane 3; and the precipitate fraction obtained by adding KURIFARM PA-896 to the centrifugal resuspension at a concentration of 0.01%, followed by low speed centrifugation at 2,500×g for 5 minutes was applied to lane 4. For the staining after electrophoresis, two staining reagents of Oriole™ fluorescent gel stain (manufactured by Bio-Rad Laboratories, Inc.) capable of staining all proteins and InVision™ His-tag In-gel Stain (manufactured by Thermo Fisher Scientific, Inc.) which reacts with the His tag region of PRT410 were used. PRT410 with a theoretical molecular weight of 53.6 kDa was detected as a band near the molecular weight marker of 60 kDa.

In the case of adding KURIFARM PA-896 to the disrupted suspension at a concentration of 0.01% and aggregating the insoluble bodies, the separation could be made by low speed centrifugation at 2,500×g for 5 minutes, and the purity of the resulting precipitate fraction was improved from 12.2% to 53.5% (see lanes 1 and 2 in FIG. 11, and Table 13 (immediately after disrupting)). The purity of the precipitate fraction could be improved from 12.2% to 36.3% (see lanes 1 and 3 in FIG. 11, and Table 13 (centrifuged and resuspended)) by precipitating the suspension immediately after disrupting bacterial cells with a high pressure homogenizer by centrifugation at 11,000×g at 20° C. for 5 minutes, and resuspending the resulting precipitate fraction again in RO water (centrifugal resuspension), but by adding KURIFARM PA-896 to the centrifugal resuspension at a concentration of 0.01% and aggregating the insoluble bodies, the separation could be made by low speed centrifugation at 2,500×g for 5 minutes, and the purity of the resulting precipitate fraction was improved again from 36.3% to 51.8% (see lanes 3 and 4 in FIG. 11, and Table 13 (centrifuged and resuspended)). It was thus possible to significantly improve the purity by adding an anionic flocculant.

TABLE 13

| | Purity (%) | |
| --- | --- | --- |
| | Not added | Flocculant added |
| Immediately after disrupting | 12.2 | 53.5 |
| Centrifuged and resuspended | 36.3 | 51.8 |

Example 10: Effect by Acid Addition, Heating, and Stirring

Figure 12:
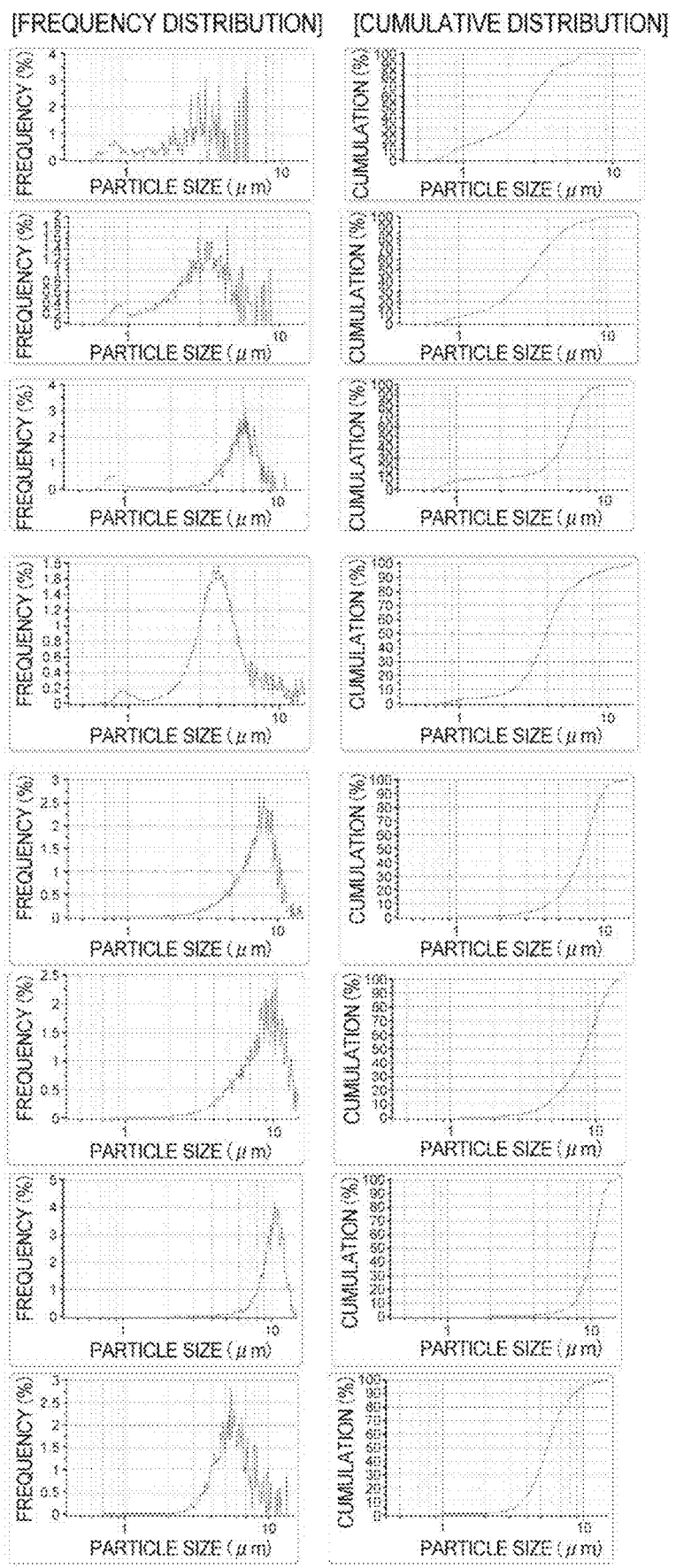
FIG. 12 is a diagram showing frequency distribution and cumulative distribution of particle sizes for confirming the aggregation effect in Example 10.

The aggregation effect by heating was confirmed using the insoluble bodies of PRT410. 1.8 μg/g wet bacterial cells of DNase and 164 μg/g wet bacterial cells of Lysozyme were added to the RO water suspension of *Escherichia coli* BLR(DE3) expressing PRT410, which was then treated four times with a high pressure homogenizer at room temperature at a pressure of 600 bar to disrupt bacterial cells. Disruption was followed by centrifugation at 2,500×g for 10 minutes, and the supernatant was discarded to adjust to 2.5-fold concentration. Then, the concentrate was 2.5-fold diluted with RO water. Citric acid was added to the disrupted suspension at a concentration of 20 mM, and then heating and stirring were carried out as needed to obtain an aggregate. Each sample was treated under the conditions described in Table 14. The heating was carried out using a hot bath and the heating time was the keeping time from the time in the case where the hot bath reached 80° C. The stirring was carried out at 200 rpm. With respect to the resulting aggregate, the particle concentration and the median diameter were measured using a particle size analyzer CDA-1000 (Sysmex Corporation). The results are shown in Table 14. FIG. 12 shows the frequency distribution and cumulative distribution of the median diameters.

Sample X that was made without adding an acid and without stilling, Sample 1 that was made with only heating and without adding an acid, and Sample 2 that was made without adding an acid and with heating and stirring exhibited almost no aggregation effect. On the other hand, Sample 3 that was made with only adding an acid and without heating/stirring exhibited an increase in particle size, as compared with Samples X, 1 and 2. Further, in Sample 7 heated at 80° C. for 2 hours, an increase in particle size was observed as compared with Sample 3. Samples 4 to 6, which had different heating times and were further stirred, were found to have an effect of increasing the particle size more by stirring. The aggregation depends on the treatment time, but the effect was observed from at least 0.5 hour. This trend is proved by FIG. 12. Since the filterability improves as the peak of the particle size distribution becomes sharper, it was confirmed from FIG. 12 that addition of an acid, heating, and stirring improve the filterability.

TABLE 14

| No. | pH | Stirring | Treatment temperature (° C.) | Treatment time (h) | Particle concentration (particles/ml) | Median diameter (μm) d10% | d50% | d90% |
|---|---|---|---|---|---|---|---|---|
| X | Not adjusted (6.0) | Not stirried | 22 | — | $4.68 \times 10^{10}$ | 0.90 | 2.72 | 5.08 |
| 1 | Not adjusted (6.0) | Not stirried | 80 | 2 | $2.57 \times 10^{10}$ | 1.37 | 3.23 | 6.40 |
| 2 | Not adjusted (6.0) | Stirried | 80 | 2 | $8.04 \times 10^{9}$ | 1.381 | 5.679 | 7.505 |
| 3 | 3.75 | Not stirried | 22 | — | $4.62 \times 10^{9}$ | 2.359 | 3.955 | 7.472 |
| 4 | 3.75 | Stirried | 80 | 0.5 | $7.09 \times 10^{10}$ | 4.37 | 7.51 | 9.90 |
| 5 | 3.75 | Stirried | 80 | 1 | $4.44 \times 10^{8}$ | 4.75 | 8.62 | 12.28 |
| 6 | 3.75 | Stirried | 80 | 2 | $2.09 \times 10^{8}$ | 7.67 | 10.39 | 12.37 |
| 7 | 3.75 | Not stirried | 80 | 2 | $9.98 \times 10^{8}$ | 3.84 | 5.62 | 8.57 |

Example 11: Effect of Improving Filterability by Type of Acid

The effect of improving filterability by adding an acid was confirmed using the insoluble bodies of PRT410. Since it was confirmed that filtration can be carried out by adding an acid, the effect of improving filterability depending on the type of acid was compared for three types of acids: citric acid, hydrochloric acid, and sulfuric acid. Experimental method was the same as in Example 10, except that the acid is different. With respect to acid treatment, Tables 15 and 16 show examples of the results concerning the relationship between the maximum filtration amount and the filtration time and the permeation flux after heating and stirring at 80° C. for 2 hours. As a result of the comparison, it was confirmed that citric acid was industrially superior because citric acid exhibited the largest maximum filtration amount and a stable permeation flux.

TABLE 15

| | Filtration area (cm$^2$) | Maximum filtration amount (m$^3$/m$^2$) |
|---|---|---|
| Not added | 45.3 | Non-filterable |
| Citric acid | 45.3 | 0.276 |
| Hydrochloric acid | 45.3 | 0.100 |
| Sulfuric acid | 45.3 | 0.092 |

TABLE 16

| pH | Heating temperature (° C.) | Heating time (h) | Particle concentration (particles/ml) | Median diameter (μm) d10% | d50% | d90% |
|---|---|---|---|---|---|---|
| 3.75 (Citric acid) | 80 | 2 | $1.34 \times 10^{8}$ | 7.928 | 9.980 | 12.365 |
| 3.75 (Hydrochloric acid) | 80 | 2 | $1.88 \times 10^{8}$ | 7.374 | 9.641 | 12.755 |
| 3.75 (Sulfuric acid) | 80 | 2 | $2.49 \times 10^{8}$ | 7.283 | 9.430 | 11.835 |

Example 12: Effect of Improving Protein Purity by Heating

Figure 13:
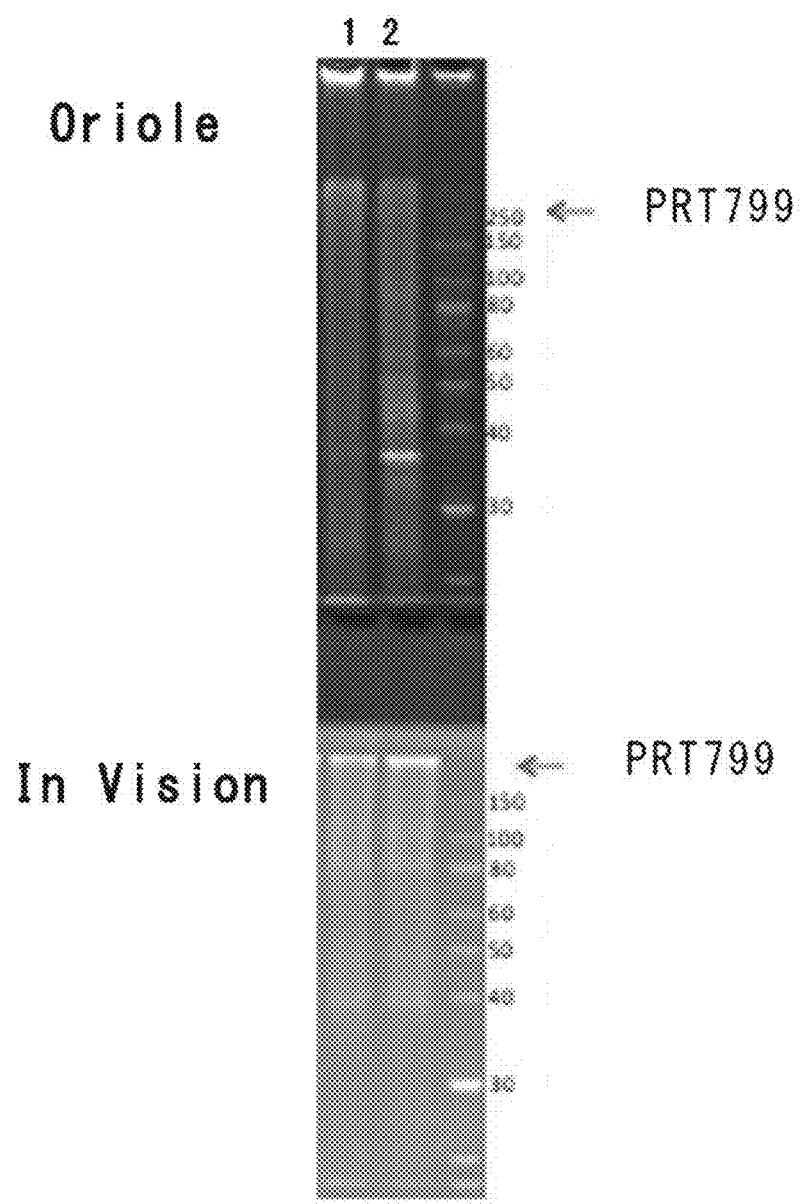
FIG. 13 is a photograph showing the results of SDS-PAGE analysis on degradation of contaminating proteins based on heating in Example 12.
Figure 14:
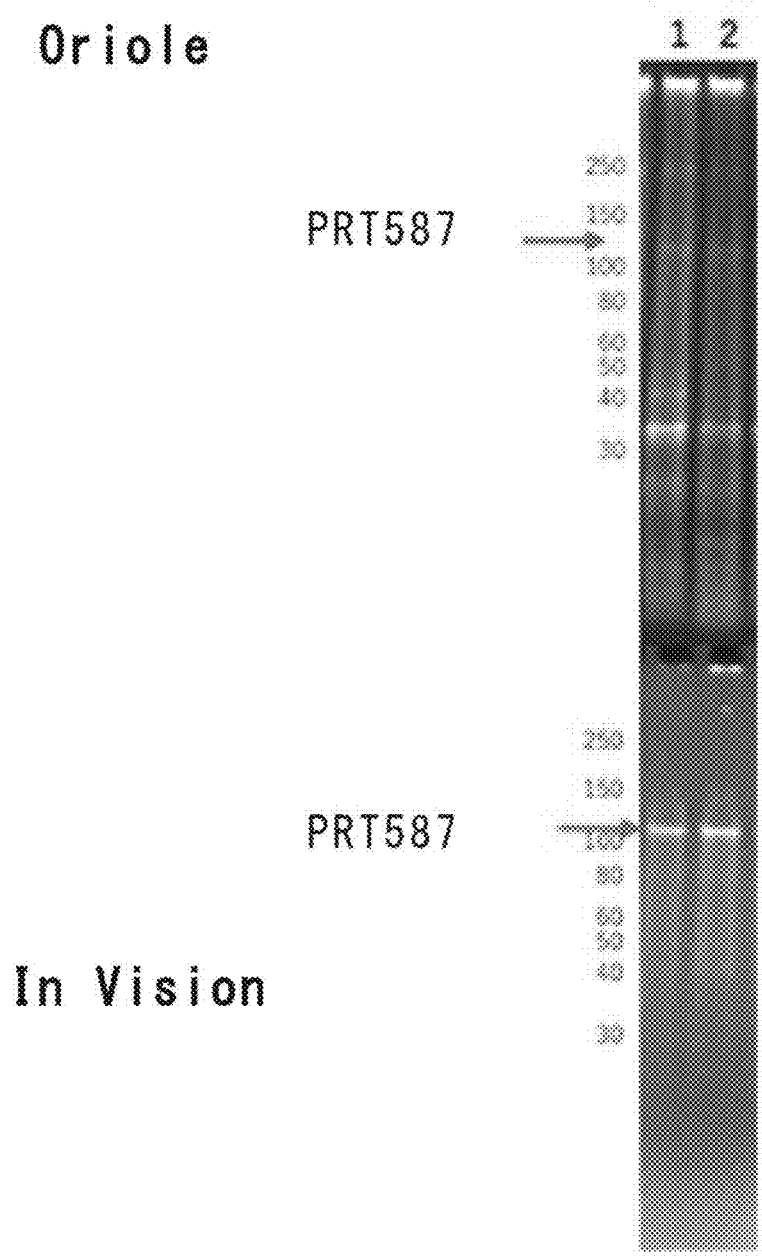
FIG. 14 is a photograph showing the results of SDS-PAGE analysis on improvement of the purity of a target recombinant protein based on heating in Example 12.

Purity of insoluble bodies of heated PRT799 (SEQ ID NO: 11, 200 kDa) and PRT587 (SEQ ID NO: 12, 100 kDa) was analyzed by SDS-PAGE. FIGS. 13 and 14 are photographs showing the results (electrophoresis results) of SDS-PAGE analysis of each treatment liquid of PRT799 and PRT587. Citric acid was added to each treatment liquid, and the pH was adjusted to 3.75. In FIG. 13, a disrupted suspension heated at 80° C. for 3 hours was applied to lane 1; and a disrupted suspension not heated was applied to lane 2. It was confirmed in the disrupted suspension of lane 1 that contaminating proteins were decomposed by heating. In FIG. 14, a disrupted suspension not heated was applied to lane 1; and a disrupted suspension heated at 80° C. for 2 hours was applied to lane 2. It was confirmed that the band near the molecular marker of 40 kDa was decomposed, and improvement in the purity of the target protein by heating was confirmed since the detected intensity of the band (target protein) detected near the 100 kDa molecular marker in lane 2 was 1.2-fold higher as compared with the band of lane 1 not heated.

Example 13: Effect by Continuous Heating

Figure 15:
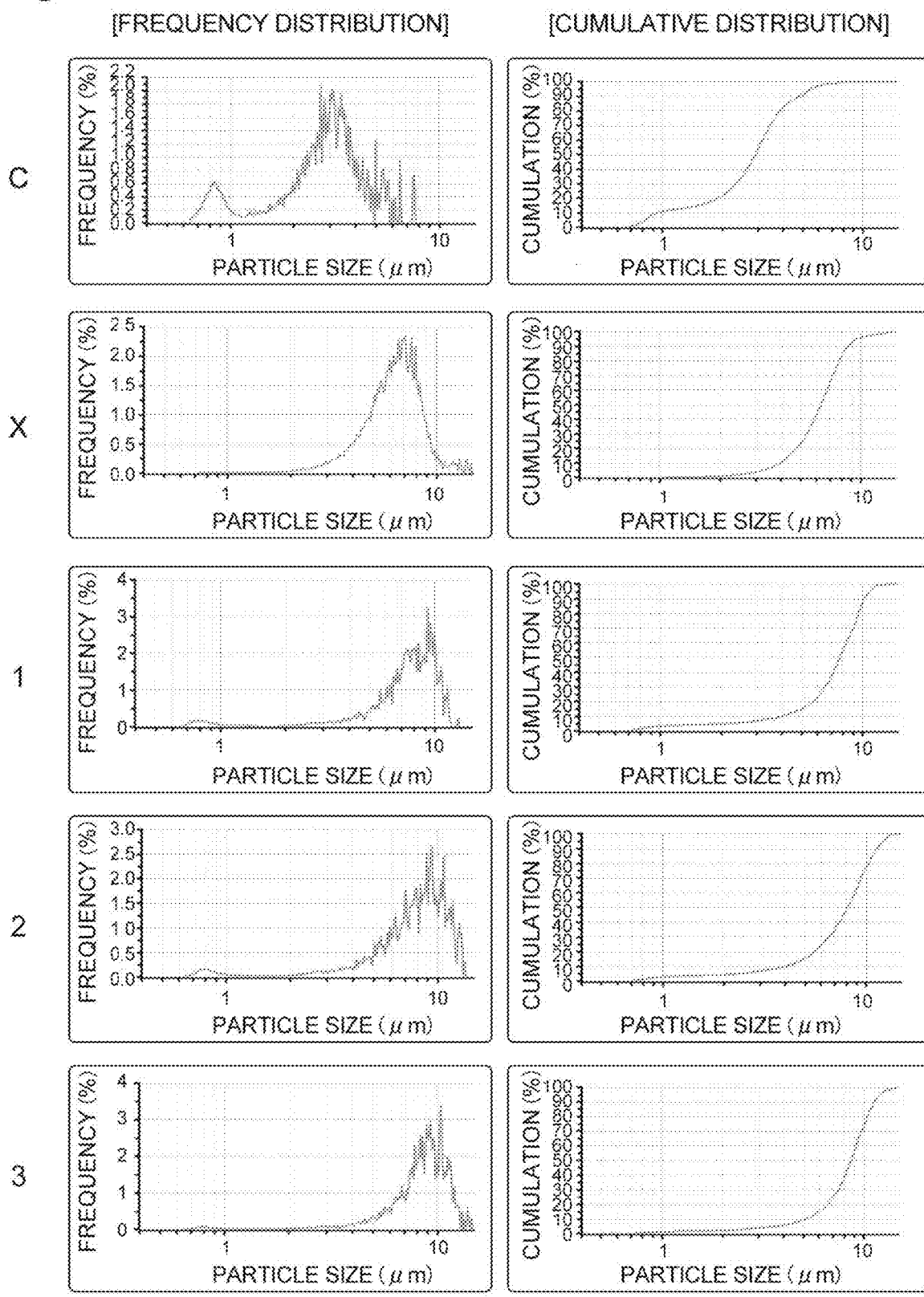
FIG. 15 is a diagram showing the frequency distribution and the cumulative distribution of particle sizes of Samples C, X, 1, 2, and 3 for confirming the aggregation effect by continuous heating in Example 13.

The aggregation effect by continuous heating was confirmed using the insoluble bodies of PRT799. 1.8 μg/g wet bacterial cells of DNase and 164 μg/g wet bacterial cells of Lysozyme were added to the RO water suspension of *Escherichia coli* BLR(DE3) expressing PRT799, which was then treated four times with a high pressure homogenizer at room temperature at a pressure of 600 bar to disrupt bacterial cells. Disruption was followed by centrifugation with a centrifuge (TOMY MX-305) at 2,500×g for 10 minutes, and the supernatant was discarded to adjust to 2.5-fold concentration. Then, the concentrate was 2.5-fold diluted with RO water. Citric acid was added to the disrupted suspension at a concentration of 20 mM, and then heating was carried out to obtain an aggregate. Each sample was treated under the conditions described in Table 17. The heating was carried out using a continuous liquid sterilizer MINI UHT T-20 (manufactured by Powerpoint International Ltd.). The heating temperature was 80° C., 85° C., 90° C., or 95° C., and the heating time of the disrupted suspension was 30 seconds or 60 seconds. With respect to the resulting aggregate, the particle concentration and the median diameter were measured using a particle size analyzer CDA-1000 (Sysmex Corporation). The results are shown in Table 17. FIGS. 14 and 15 show the frequency distribution and cumulative distribution of the median diameters.

TABLE 17

| No. | pH | Treatment temperature (° C.) | Treatment time | Particle concentration (particles/ml) | Median diameter (μm) | | |
|-----|-----|-----|-----|-----|-----|-----|-----|
| | | | | | d10% | d50% | d90% |
| C | Before heating (3.75) | 25 | Not heated | $1.52 \times 10^{10}$ | 0.959 | 2.940 | 4.861 |
| X | 3.75 | 80 | 2 hours | $5.08 \times 10^{8}$ | 4.001 | 6.412 | 8.685 |
| 1 | 3.75 | 80 | 30 seconds | $1.32 \times 10^{9}$ | 3.987 | 7.824 | 10.275 |
| 2 | 3.75 | 80 | 60 seconds | $1.09 \times 10^{9}$ | 3.951 | 8.163 | 11.415 |
| 3 | 3.75 | 85 | 30 seconds | $6.48 \times 10^{8}$ | 5.166 | 8.778 | 11.415 |
| 4 | 3.75 | 85 | 60 seconds | $4.19 \times 10^{8}$ | 4.865 | 9.070 | 12.525 |
| 5 | 3.75 | 90 | 30 seconds | $1.44 \times 10^{8}$ | 6.773 | 11.045 | 13.825 |
| 6 | 3.75 | 90 | 60 seconds | $2.51 \times 10^{8}$ | 5.434 | 10.845 | 13.810 |
| 7 | 3.75 | 95 | 30 seconds | $8.27 \times 10^{7}$ | 5.664 | 11.825 | 14.510 |
| 8 | 3.75 | 95 | 60 seconds | $1.02 \times 10^{8}$ | 3.035 | 11.535 | 14.475 |

From the results in Table 17, in the case where the aggregate of Sample X obtained by heating using a hot bath at a heating temperature of 80° C. for a heating time of 2 hours was compared with the aggregate of Sample 1, 2, 3, 4, 5, 6, 7, or 8 obtained using a continuous liquid sterilizer MINI UHT T-20 (manufactured by Powerpoint International Ltd.) at a heating temperature of 80° C., 85° C., 90° C., or 95° C. for a heating time of 30 seconds or 60 seconds, the aggregate obtained using a continuous liquid sterilizer MINI UHT T-20 (manufactured by Powerpoint International Ltd.) had a particle size equal to or larger than that of the aggregate obtained by heating in a hot bath.

Figure 16:
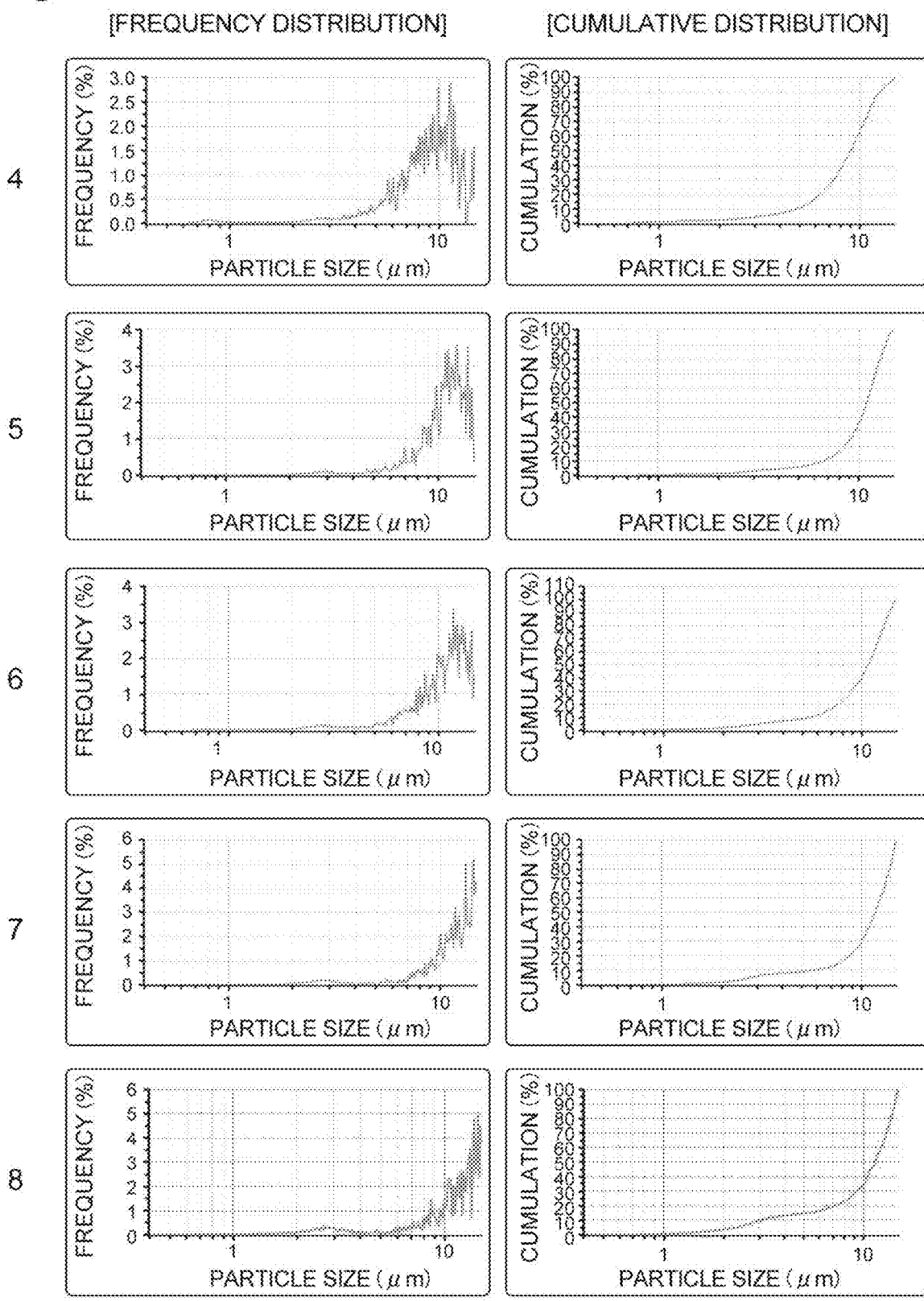
FIG. 16 is a diagram showing the frequency distribution and the cumulative distribution of particle sizes of Samples 4, 5, 6, 7, and 8 for confirming the aggregation effect by continuous heating in Example 13.

It was confirmed from FIGS. 15 and 16 that the aggregate could be efficiently enlarged by heating the disrupted suspension at a high temperature for a short period of time.

Example 14: Effect of Improving Filterability by Continuous Heating

The results of filtration area and maximum filtration amount of Samples X, 5, 6, 7, and 8 are shown in Table 18.

According to Table 18, the filterability in the case of heating at a high temperature for a short period of time by using a continuous liquid sterilizer was about the same or about the same as or higher than that obtained by heating using a hot bath for 2 hours, and it was confirmed that filterability was improved in the case where the disrupted suspension was heated at a high temperature for a short period of time.

TABLE 18

| No. | pH | Treatment temperature (° C.) | Treatment time | Filtration area (cm²) | Maximum filtration amount (m³/m²) |
|-----|-----|-----|-----|-----|-----|
| X | 3.75 | 80 | 2 hours | 45.3 | 0.078 |
| 5 | 3.75 | 90 | 30 seconds | 45.3 | 0.099 |
| 6 | 3.75 | 90 | 60 seconds | 45.3 | 0.101 |
| 7 | 3.75 | 95 | 30 seconds | 45.3 | 0.103 |
| 8 | 3.75 | 95 | 60 seconds | 45.3 | 0.099 |

The invention claimed is:

1. A method for producing a recombinant protein aggregate, comprising the following steps (A) to (C):
   a step (A) of disrupting a recombinant cell expressing a target recombinant protein as insoluble bodies in the cell to obtain a disrupted suspension containing the insoluble bodies of the recombinant protein;
   a step (B) of adding one or more selected from the group consisting of a metal salt, an acid, and an anionic flocculant to the disrupted suspension obtained in the step (A), and aggregating the insoluble bodies of the recombinant protein to obtain the recombinant protein aggregate; and
   a step (C) of separating the aggregate obtained in the step (B) from the suspension, wherein the recombinant protein is not substantially dissolved in the disrupted suspension.

2. The method for producing a recombinant protein aggregate according to claim 1, further comprising:
   separating the recombinant protein aggregate by a centrifugal force of 10,000×g or less.

3. The method for producing a recombinant protein aggregate according to claim 1, further comprising:
   separating the recombinant protein aggregate by using a centrifuge selected from the group consisting of a separation plate type centrifuge, a basket type centrifuge, and a decanter type centrifuge.

4. The method for producing a recombinant protein aggregate according to claim 1, further comprising:
   separating the recombinant protein aggregate by spontaneous sedimentation or filtration.

5. The method for producing a recombinant protein aggregate according to claim 1, further comprising:
   heating in the step (B).

6. The method for producing a recombinant protein aggregate according to claim 5, further comprising:
   stirring in the step (B).

7. The method for producing a recombinant protein aggregate according to claim 1, wherein the metal salt is a metal salt selected from the group consisting of an alkaline earth metal salt and an earth metal salt.

8. The method for producing a recombinant protein aggregate according to claim 7, wherein the metal salt is a metal salt selected from the group consisting of an alkaline earth metal halide, an alkaline earth metal nitrate, an alkaline earth metal sulfate, an earth metal halide, an earth metal nitrate, and an earth metal sulfate.

9. The method for producing a recombinant protein aggregate according to claim 1, wherein the acid is an oxo acid.

10. The method for producing a recombinant protein aggregate according to claim 9, wherein the oxo acid is an oxo acid selected from the group consisting of acetic acid, sulfuric acid, and citric acid.

11. The method for producing a recombinant protein aggregate according to claim 1, wherein the anionic flocculant is an anionic flocculant selected from the group consisting of a polyacrylate, an anionic polyacrylamide, and an acrylamide-acrylate copolymer.

12. The method for producing a recombinant protein aggregate according to claim 1, wherein the disruption of the recombinant cell is mechanical disruption.

13. The method for producing a recombinant protein aggregate according to claim 1, wherein the separation of the recombinant protein aggregate is carried out by filtration.

14. The method for producing a recombinant protein aggregate according to claim 1, wherein the recombinant cell is a recombinant cell transformed with a host selected from the group consisting of a bacterium, a yeast, a filamentous fungus, an insect cell, a plant cell, and an animal cell.

15. The method for producing a recombinant protein aggregate according to claim 1, wherein the recombinant protein is a structural protein.

16. The method for producing a recombinant protein aggregate according to claim 15, wherein the structural protein is a protein derived from a protein selected from the group consisting of keratin, collagen, elastin, resilin, silkworm silk, and spider silk.

17. The method for producing a recombinant protein aggregate according to claim 1, wherein the resulting recombinant protein aggregate has a particle size of 4 µm to 50 µm as measured by an electrical sensing zone method.

* * * * *

SEQUENCE LISTING

```
<160> NUMBER OF SEQ ID NOS: 12

<210> SEQ ID NO 1
<211> LENGTH: 601
<212> TYPE: PRT
<213> ORGANISM: Artificial Sequence
<220> FEATURE:
<223> OTHER INFORMATION: PRT410

<400> SEQUENCE: 1

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
                20                  25                  30

Asn Gly Pro Gly Ser Gly Gln Gln Gly Pro Gly Gln Ser Gly Gln Tyr
                35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95
```

-continued

```
Pro Gly Ala Ser Gly Gln Tyr Gly Pro Gly Gln Gly Pro Gly Gln
                100                 105                 110
Gln Gly Pro Gly Ser Ser Ala Ala Ala Ala Gly Gln Tyr Gly Ser
        115                 120                 125
Gly Pro Gly Gln Gln Gly Pro Tyr Gly Ser Ala Ala Ala Ala Gly
        130                 135                 140
Pro Gly Ser Gly Gln Tyr Gly Gln Pro Tyr Gly Pro Gly Ala Ser
145                 150                 155                 160
Gly Pro Gly Gln Tyr Gly Pro Gly Gln Gly Pro Ser Ala Ser Ala
                165                 170                 175
Ala Ala Ala Ala Gly Ser Gly Gln Gln Gly Pro Gly Gln Tyr Gly Pro
            180                 185                 190
Tyr Ala Ser Ala Ala Ala Ala Gly Gln Tyr Gly Ser Gly Pro Gly
            195                 200                 205
Gln Gln Gly Pro Tyr Gly Pro Gly Ser Gly Ser Gly Gln Gln Gly
        210                 215                 220
Pro Gly Gln Gln Gly Pro Tyr Ala Ser Ala Ala Ala Ala Gly Pro
225                 230                 235                 240
Gly Gln Gln Gly Pro Tyr Gly Pro Gly Ser Ser Ala Ala Ala Ala
                245                 250                 255
Gly Gln Tyr Gly Tyr Gly Pro Gly Gln Gly Pro Tyr Gly Pro Gly
            260                 265                 270
Ala Ser Gly Gln Asn Gly Pro Gly Ser Gly Gln Tyr Gly Pro Gly Gln
            275                 280                 285
Gln Gly Pro Gly Gln Ser Ala Ala Ala Ala Gly Pro Gly Gln Gln
        290                 295                 300
Gly Pro Tyr Gly Pro Gly Ala Ser Ala Ala Ala Ala Gly Gln Tyr
305                 310                 315                 320
Gly Pro Gly Gln Gln Gly Pro Gly Tyr Gly Pro Gly Ser Ser Gly
                325                 330                 335
Pro Gly Gln Gln Gly Pro Tyr Gly Pro Gly Ser Ser Ala Ala Ala
            340                 345                 350
Ala Gly Gln Tyr Gly Pro Gly Gln Gln Gly Pro Tyr Gly Pro Gly Gln
            355                 360                 365
Ser Ala Ala Ala Ala Gly Gln Tyr Gln Gln Gly Pro Gly Gln Gln
        370                 375                 380
Gly Pro Tyr Gly Pro Gly Ala Ser Gly Pro Gly Gln Gln Gly Pro Tyr
385                 390                 395                 400
Gly Pro Gly Ala Ser Ala Ala Ala Ala Gly Pro Gly Gln Tyr Gly
                405                 410                 415
Pro Gly Gln Gln Gly Pro Ser Ala Ser Ala Ala Ala Ala Gly Gln
            420                 425                 430
Tyr Gly Ser Gly Pro Gly Gln Tyr Gly Pro Tyr Gly Pro Gly Gln Ser
        435                 440                 445
Gly Pro Gly Ser Gly Gln Gln Gly Gln Gly Pro Tyr Gly Pro Gly Ala
        450                 455                 460
Ser Ala Ala Ala Ala Gly Gln Tyr Gly Pro Gly Gln Gln Gly Pro
465                 470                 475                 480
Tyr Gly Pro Gly Gln Ser Ala Ala Ala Ala Gly Pro Gly Ser Gly
                485                 490                 495
Gln Tyr Gly Pro Gly Ala Ser Gly Gln Asn Gly Pro Gly Ser Gly Gln
            500                 505                 510
Tyr Gly Pro Gly Gln Gln Gly Pro Gly Gln Ser Ala Ala Ala Ala Ala
```

```
                515                 520                 525
Gly Gln Tyr Gln Gln Gly Pro Gly Gln Gly Pro Tyr Gly Pro Gly
            530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
        595                 600

<210> SEQ ID NO 2
<211> LENGTH: 2476
<212> TYPE: PRT
<213> ORGANISM: Artificial Sequence
<220> FEATURE:
<223> OTHER INFORMATION: PRT853

<400> SEQUENCE: 2

Met His His His His His Ser Ser Gly Ser Gly Pro Gly Gln
1               5                   10                  15

Gln Gly Pro Tyr Gly Pro Gly Ala Ser Ala Ala Ala Ala Ala Gly
                20                  25                  30

Gln Asn Gly Pro Gly Ser Gly Gln Gln Gly Pro Gly Gln Ser Gly Gln
            35                  40                  45

Tyr Gly Pro Gly Gln Gln Gly Pro Gly Gln Gly Pro Gly Ser Ser
    50                  55                  60

Ala Ala Ala Ala Ala Gly Pro Gly Gln Tyr Gly Pro Gly Gln Gln
65                  70                  75                  80

Gly Pro Ser Ala Ser Ala Ala Ala Ala Ala Gly Pro Gly Ser Gly
                85                  90                  95

Gln Gln Gly Pro Gly Ala Ser Gly Gln Tyr Gly Pro Gly Gln Gln Gly
            100                 105                 110

Pro Gly Gln Gln Gly Pro Gly Ser Ser Ala Ala Ala Ala Ala Gly
        115                 120                 125

Gln Tyr Gly Ser Gly Pro Gly Gln Gln Gly Pro Tyr Gly Ser Ala Ala
    130                 135                 140

Ala Ala Ala Ala Gly Pro Gly Ser Gly Gln Tyr Gly Gly Pro Tyr
145                 150                 155                 160

Gly Pro Gly Ala Ser Gly Pro Gly Gln Tyr Gly Pro Gly Gln Gln Gly
                165                 170                 175

Pro Ser Ala Ser Ala Ala Ala Ala Ala Gly Ser Gly Gln Gln Gly
            180                 185                 190

Pro Gly Gln Tyr Gly Pro Tyr Ala Ser Ala Ala Ala Ala Ala Gly
        195                 200                 205

Gln Tyr Gly Ser Gly Pro Gly Gln Gln Gly Pro Tyr Gly Pro Gly Gln
    210                 215                 220

Ser Gly Ser Gly Gln Gln Gly Pro Gly Gln Gly Pro Tyr Ala Ser
225                 230                 235                 240

Ala Ala Ala Ala Ala Gly Pro Gly Gln Gln Gly Pro Tyr Gly Pro
                245                 250                 255

Gly Ser Ser Ala Ala Ala Ala Ala Gly Gln Tyr Gly Tyr Gly Pro
            260                 265                 270

Gly Gln Gln Gly Pro Tyr Gly Pro Gly Ala Ser Gly Gln Asn Gly Pro
```

-continued

```
                275                 280                 285
Gly Ser Gly Gln Tyr Gly Pro Gly Gln Gln Gly Pro Gly Gln Ser Ala
290                 295                 300

Ala Ala Ala Ala Ala Gly Pro Gly Gln Gln Gly Pro Tyr Gly Pro Gly
305                 310                 315                 320

Ala Ser Ala Ala Ala Ala Ala Gly Gln Tyr Gly Pro Gly Gln Gln
            325                 330                 335

Gly Pro Gly Gln Tyr Gly Pro Gly Ser Ser Gly Pro Gly Gln Gln Gly
            340                 345                 350

Pro Tyr Gly Pro Gly Ser Ser Ala Ala Ala Ala Ala Gly Gln Tyr
            355                 360                 365

Gly Pro Gly Gln Gln Gly Pro Tyr Gly Pro Gly Gln Ser Ala Ala Ala
370                 375                 380

Ala Ala Ala Gly Gln Tyr Gln Gln Gly Pro Gly Gln Gln Gly Pro Tyr
385                 390                 395                 400

Gly Pro Gly Ala Ser Gly Pro Gly Gln Gln Gly Pro Tyr Gly Pro Gly
            405                 410                 415

Ala Ser Ala Ala Ala Ala Ala Gly Pro Gly Gln Tyr Gly Pro Gly
            420                 425                 430

Gln Gln Gly Pro Ser Ala Ser Ala Ala Ala Ala Ala Gly Gln Tyr
            435                 440                 445

Gly Ser Gly Pro Gly Gln Tyr Gly Pro Tyr Gly Pro Gly Gln Ser Gly
450                 455                 460

Pro Gly Ser Gly Gln Gln Gly Gln Gly Pro Tyr Gly Pro Gly Ala Ser
465                 470                 475                 480

Ala Ala Ala Ala Ala Ala Gly Gln Tyr Gly Pro Gly Gln Gln Gly Pro
            485                 490                 495

Tyr Gly Pro Gly Gln Ser Ala Ala Ala Ala Ala Gly Pro Gly Ser
            500                 505                 510

Gly Gln Tyr Gly Pro Gly Ala Ser Gly Gln Asn Gly Pro Gly Ser Gly
            515                 520                 525

Gln Tyr Gly Pro Gly Gln Gln Gly Pro Gly Gln Ser Ala Ala Ala Ala
            530                 535                 540

Ala Ala Gly Gln Tyr Gln Gln Gly Pro Gly Gln Gln Gly Pro Tyr Gly
545                 550                 555                 560

Pro Gly Ala Ser Ala Ala Ala Ala Ala Gly Gln Tyr Gly Ser Gly
            565                 570                 575

Pro Gly Gln Gln Gly Pro Tyr Gly Pro Gly Gln Ser Gly Ser Gly Gln
            580                 585                 590

Gln Gly Pro Gly Gln Gln Gly Pro Tyr Ala Ser Ala Ala Ala Ala Ala
            595                 600                 605

Ala Gly Pro Gly Ser Gly Gln Gln Gly Pro Gly Ala Ser Ala Ala Ala
            610                 615                 620

Ala Ala Ala Ala Glu Phe Gly Gln Gln Gly Pro Tyr Gly Pro Gly Ala
625                 630                 635                 640

Ser Ala Ala Ala Ala Ala Gly Gln Asn Gly Pro Gly Ser Gly Gln
            645                 650                 655

Gln Gly Pro Gly Gln Ser Gly Tyr Gly Pro Gly Gln Gln Gly Pro
            660                 665                 670

Gly Gln Gln Gly Pro Gly Ser Ser Ala Ala Ala Ala Ala Gly Pro
            675                 680                 685

Gly Gln Tyr Gly Pro Gly Gln Gln Gly Pro Ser Ala Ser Ala Ala Ala
690                 695                 700
```

```
Ala Ala Ala Gly Pro Gly Ser Gly Gln Gln Gly Pro Gly Ala Ser Gly
705                 710                 715                 720

Gln Tyr Gly Pro Gly Gln Gly Pro Gly Gln Gly Pro Gly Pro Gly Ser
                725                 730                 735

Ser Ala Ala Ala Ala Ala Gly Gln Tyr Gly Ser Gly Pro Gly Gln
            740                 745                 750

Gln Gly Pro Tyr Gly Ser Ala Ala Ala Ala Gly Pro Gly Ser
        755                 760                 765

Gly Gln Tyr Gly Gln Gly Pro Tyr Gly Pro Gly Ala Ser Gly Pro Gly
    770                 775                 780

Gln Tyr Gly Pro Gly Gln Gln Gly Pro Ser Ala Ser Ala Ala Ala Ala
785                 790                 795                 800

Ala Ala Gly Ser Gly Gln Gln Gly Pro Gly Gln Tyr Gly Pro Tyr Ala
            805                 810                 815

Ser Ala Ala Ala Ala Ala Gly Gln Tyr Gly Ser Gly Pro Gly Gln
            820                 825                 830

Gln Gly Pro Tyr Gly Pro Gly Gln Ser Gly Ser Gly Gln Gln Gly Pro
        835                 840                 845

Gly Gln Gln Gly Pro Tyr Ala Ser Ala Ala Ala Ala Ala Gly Pro
850                 855                 860

Gly Gln Gln Gly Pro Tyr Gly Pro Gly Ser Ser Ala Ala Ala Ala
865                 870                 875                 880

Ala Gly Gln Tyr Gly Tyr Gly Pro Gln Gln Gly Pro Tyr Gly Pro
            885                 890                 895

Gly Ala Ser Gly Gln Asn Gly Pro Gly Ser Gly Gln Tyr Gly Pro Gly
            900                 905                 910

Gln Gln Gly Pro Gly Gln Ser Ala Ala Ala Ala Ala Gly Pro Gly
        915                 920                 925

Gln Gln Gly Pro Tyr Gly Pro Gly Ala Ser Ala Ala Ala Ala Ala
        930                 935                 940

Gly Gln Tyr Gly Pro Gly Gln Gln Gly Pro Gly Gln Tyr Gly Pro Gly
945                 950                 955                 960

Ser Ser Gly Pro Gly Gln Gln Gly Pro Tyr Gly Pro Gly Ser Ser Ala
                965                 970                 975

Ala Ala Ala Ala Gly Gln Tyr Gly Pro Gly Gln Gln Gly Pro Tyr
            980                 985                 990

Gly Pro Gly Gln Ser Ala Ala Ala Ala Ala Gly Gln Tyr Gln Gln
        995                 1000                1005

Gly Pro Gly Gln Gln Gly Pro Tyr Gly Pro Gly Ala Ser Gly Pro
    1010                1015                1020

Gly Gln Gln Gly Pro Tyr Gly Pro Gly Ala Ser Ala Ala Ala Ala
    1025                1030                1035

Ala Ala Gly Pro Gly Gln Tyr Gly Pro Gly Gln Gln Gly Pro Ser
    1040                1045                1050

Ala Ser Ala Ala Ala Ala Ala Gly Gln Tyr Gly Ser Gly Pro
    1055                1060                1065

Gly Gln Tyr Gly Pro Tyr Gly Pro Gly Gln Ser Gly Pro Gly Ser
    1070                1075                1080

Gly Gln Gln Gly Gln Gly Pro Tyr Gly Pro Gly Ala Ser Ala Ala
    1085                1090                1095

Ala Ala Ala Ala Gly Gln Tyr Gly Pro Gly Gln Gln Gly Pro Tyr
    1100                1105                1110
```

-continued

Gly Pro Gly Gln Ser Ala Ala Ala Ala Ala Gly Pro Gly Ser
1115                1120                1125

Gly Gln Tyr Gly Pro Gly Ala Ser Gly Gln Asn Gly Pro Gly Ser
1130                1135                1140

Gly Gln Tyr Gly Pro Gly Gln Gln Gly Pro Gly Gln Ser Ala Ala
1145                1150                1155

Ala Ala Ala Ala Gly Gln Tyr Gln Gln Gly Pro Gly Gln Gln Gly
1160                1165                1170

Pro Tyr Gly Pro Gly Ala Ser Ala Ala Ala Ala Ala Gly Gln
1175                1180                1185

Tyr Gly Ser Gly Pro Gly Gln Gln Gly Pro Tyr Gly Pro Gly Gln
1190                1195                1200

Ser Gly Ser Gly Gln Gln Gly Pro Gly Gln Gln Gly Pro Tyr Ala
1205                1210                1215

Ser Ala Ala Ala Ala Ala Gly Pro Gly Ser Gly Gln Gln Gly
1220                1225                1230

Pro Gly Ala Ser Ala Ala Ala Ala Ala Ala Glu Leu Gly Gln
1235                1240                1245

Gln Gly Pro Tyr Gly Pro Gly Ala Ser Ala Ala Ala Ala Ala Ala
1250                1255                1260

Gly Gln Asn Gly Pro Gly Ser Gly Gln Gln Gly Pro Gly Gln Ser
1265                1270                1275

Gly Gln Tyr Gly Pro Gly Gln Gln Gly Pro Gly Gln Gln Gly Pro
1280                1285                1290

Gly Ser Ser Ala Ala Ala Ala Ala Gly Pro Gly Gln Tyr Gly
1295                1300                1305

Pro Gly Gln Gln Gly Pro Ser Ala Ser Ala Ala Ala Ala Ala Ala
1310                1315                1320

Gly Pro Gly Ser Gly Gln Gln Gly Pro Gly Ala Ser Gly Gln Tyr
1325                1330                1335

Gly Pro Gly Gln Gln Gly Pro Gly Gln Gly Pro Gly Ser Ser
1340                1345                1350

Ala Ala Ala Ala Ala Ala Gly Gln Tyr Gly Ser Gly Pro Gly Gln
1355                1360                1365

Gln Gly Pro Tyr Gly Ser Ala Ala Ala Ala Ala Gly Pro Gly
1370                1375                1380

Ser Gly Gln Tyr Gly Gln Gly Pro Tyr Gly Pro Gly Ala Ser Gly
1385                1390                1395

Pro Gly Gln Tyr Gly Pro Gly Gln Gln Gly Pro Ser Ala Ser Ala
1400                1405                1410

Ala Ala Ala Ala Gly Ser Gly Gln Gln Gly Pro Gly Gln Tyr
1415                1420                1425

Gly Pro Tyr Ala Ser Ala Ala Ala Ala Ala Gly Gln Tyr Gly
1430                1435                1440

Ser Gly Pro Gly Gln Gln Gly Pro Tyr Gly Pro Gly Gln Ser Gly
1445                1450                1455

Ser Gly Gln Gln Gly Pro Gly Gln Gln Gly Pro Tyr Ala Ser Ala
1460                1465                1470

Ala Ala Ala Ala Ala Gly Pro Gly Gln Gly Pro Tyr Gly Pro
1475                1480                1485

Gly Ser Ser Ala Ala Ala Ala Ala Ala Gly Gln Tyr Gly Tyr Gly
1490                1495                1500

Pro Gly Gln Gln Gly Pro Tyr Gly Pro Gly Ala Ser Gly Gln Asn

```
            1505                1510                1515

Gly Pro Gly Ser Gly Gln Tyr Gly Pro Gly Gln Gly Pro Gly
        1520                1525                1530

Gln Ser Ala Ala Ala Ala Ala Gly Pro Gly Gln Gln Gly Pro
    1535                1540                1545

Tyr Gly Pro Gly Ala Ser Ala Ala Ala Ala Ala Gly Gln Tyr
    1550                1555                1560

Gly Pro Gly Gln Gln Gly Pro Gly Gln Tyr Gly Pro Gly Ser Ser
    1565                1570                1575

Gly Pro Gly Gln Gln Gly Pro Tyr Gly Pro Gly Ser Ser Ala Ala
    1580                1585                1590

Ala Ala Ala Ala Gly Gln Tyr Gly Pro Gly Gln Gln Gly Pro Tyr
    1595                1600                1605

Gly Pro Gly Gln Ser Ala Ala Ala Ala Ala Gly Gln Tyr Gln
    1610                1615                1620

Gln Gly Pro Gly Gln Gln Gly Pro Tyr Gly Pro Gly Ala Ser Gly
    1625                1630                1635

Pro Gly Gln Gln Gly Pro Tyr Gly Pro Gly Ala Ser Ala Ala Ala
    1640                1645                1650

Ala Ala Ala Gly Pro Gly Gln Tyr Gly Pro Gly Gln Gln Gly Pro
    1655                1660                1665

Ser Ala Ser Ala Ala Ala Ala Ala Gly Gln Tyr Gly Ser Gly
    1670                1675                1680

Pro Gly Gln Tyr Gly Pro Tyr Gly Pro Gly Gln Ser Gly Pro Gly
    1685                1690                1695

Ser Gly Gln Gln Gly Gln Gly Pro Tyr Gly Pro Gly Ala Ser Ala
    1700                1705                1710

Ala Ala Ala Ala Gly Gln Tyr Gly Pro Gly Gln Gln Gly Pro
    1715                1720                1725

Tyr Gly Pro Gly Gln Ser Ala Ala Ala Ala Ala Gly Pro Gly
    1730                1735                1740

Ser Gly Gln Tyr Gly Pro Gly Ala Ser Gly Gln Asn Gly Pro Gly
    1745                1750                1755

Ser Gly Gln Tyr Gly Pro Gly Gln Gln Gly Pro Gly Gln Ser Ala
    1760                1765                1770

Ala Ala Ala Ala Gly Gln Tyr Gln Gln Gly Pro Gly Gln Gln
    1775                1780                1785

Gly Pro Tyr Gly Pro Gly Ala Ser Ala Ala Ala Ala Ala Gly
    1790                1795                1800

Gln Tyr Gly Ser Gly Pro Gly Gln Gln Gly Pro Tyr Gly Pro Gly
    1805                1810                1815

Gln Ser Gly Ser Gly Gln Gln Gly Pro Gly Gln Gln Gly Pro Tyr
    1820                1825                1830

Ala Ser Ala Ala Ala Ala Ala Gly Pro Gly Ser Gly Gln Gln
    1835                1840                1845

Gly Pro Gly Ala Ser Ala Ala Ala Ala Ala Ala Lys Leu Gly
    1850                1855                1860

Gln Gln Gly Pro Tyr Gly Pro Gly Ala Ser Ala Ala Ala Ala Ala
    1865                1870                1875

Ala Gly Gln Asn Gly Pro Gly Ser Gly Gln Gln Gly Pro Gly Gln
    1880                1885                1890

Ser Gly Gln Tyr Gly Pro Gly Gln Gln Gly Pro Gly Gln Gln Gly
    1895                1900                1905
```

Pro Gly Ser Ser Ala Ala Ala Ala Ala Gly Pro Gly Gln Tyr
    1910                1915                1920

Gly Pro Gly Gln Gln Gly Pro Ser Ala Ser Ala Ala Ala Ala
    1925                1930                1935

Ala Gly Pro Gly Ser Gly Gln Gln Gly Pro Gly Ala Ser Gly Gln
    1940                1945                1950

Tyr Gly Pro Gly Gln Gln Gly Pro Gly Gln Gln Gly Pro Gly Ser
    1955                1960                1965

Ser Ala Ala Ala Ala Ala Ala Gly Gln Tyr Gly Ser Gly Pro Gly
    1970                1975                1980

Gln Gln Gly Pro Tyr Gly Ser Ala Ala Ala Ala Ala Gly Pro
    1985                1990                1995

Gly Ser Gly Gln Tyr Gly Gln Gly Pro Tyr Gly Pro Gly Ala Ser
    2000                2005                2010

Gly Pro Gly Gln Tyr Gly Pro Gly Gln Gln Gly Pro Ser Ala Ser
    2015                2020                2025

Ala Ala Ala Ala Ala Ala Gly Ser Gly Gln Gln Gly Pro Gly Gln
    2030                2035                2040

Tyr Gly Pro Tyr Ala Ser Ala Ala Ala Ala Ala Gly Gln Tyr
    2045                2050                2055

Gly Ser Gly Pro Gly Gln Gln Gly Pro Tyr Gly Pro Gly Gln Ser
    2060                2065                2070

Gly Ser Gly Gln Gln Gly Pro Gly Gln Gln Gly Pro Tyr Ala Ser
    2075                2080                2085

Ala Ala Ala Ala Ala Ala Gly Pro Gly Gln Gln Gly Pro Tyr Gly
    2090                2095                2100

Pro Gly Ser Ser Ala Ala Ala Ala Ala Gly Gln Tyr Gly Tyr
    2105                2110                2115

Gly Pro Gly Gln Gln Gly Pro Tyr Gly Pro Gly Ala Ser Gly Gln
    2120                2125                2130

Asn Gly Pro Gly Ser Gly Gln Tyr Gly Pro Gly Gln Gln Gly Pro
    2135                2140                2145

Gly Gln Ser Ala Ala Ala Ala Ala Ala Gly Pro Gly Gln Gln Gly
    2150                2155                2160

Pro Tyr Gly Pro Gly Ala Ser Ala Ala Ala Ala Ala Gly Gln
    2165                2170                2175

Tyr Gly Pro Gly Gln Gln Gly Pro Gly Gln Tyr Gly Pro Gly Ser
    2180                2185                2190

Ser Gly Pro Gly Gln Gln Gly Pro Tyr Gly Pro Gly Ser Ser Ala
    2195                2200                2205

Ala Ala Ala Ala Ala Gly Gln Tyr Gly Pro Gly Gln Gln Gly Pro
    2210                2215                2220

Tyr Gly Pro Gly Gln Ser Ala Ala Ala Ala Ala Gly Gln Tyr
    2225                2230                2235

Gln Gln Gly Pro Gly Gln Gln Gly Pro Tyr Gly Pro Gly Ala Ser
    2240                2245                2250

Gly Pro Gly Gln Gln Gly Pro Tyr Gly Pro Gly Ala Ser Ala Ala
    2255                2260                2265

Ala Ala Ala Ala Gly Pro Gly Gln Tyr Gly Pro Gly Gln Gln Gly
    2270                2275                2280

Pro Ser Ala Ser Ala Ala Ala Ala Ala Gly Gln Tyr Gly Ser
    2285                2290                2295

```
Gly Pro Gly Gln Tyr Gly Pro Tyr Gly Pro Gly Gln Ser Gly Pro
    2300                2305                2310

Gly Ser Gly Gln Gln Gly Gln Gly Pro Tyr Gly Pro Gly Ala Ser
    2315                2320                2325

Ala Ala Ala Ala Ala Ala Gly Gln Tyr Gly Pro Gly Gln Gln Gly
    2330                2335                2340

Pro Tyr Gly Pro Gly Gln Ser Ala Ala Ala Ala Ala Ala Gly Pro
    2345                2350                2355

Gly Ser Gly Gln Tyr Gly Pro Gly Ala Ser Gly Gln Asn Gly Pro
    2360                2365                2370

Gly Ser Gly Gln Tyr Gly Pro Gly Gln Gln Gly Pro Gly Gln Ser
    2375                2380                2385

Ala Ala Ala Ala Ala Ala Gly Gln Tyr Gln Gln Gly Pro Gly Gln
    2390                2395                2400

Gln Gly Pro Tyr Gly Pro Gly Ala Ser Ala Ala Ala Ala Ala Ala
    2405                2410                2415

Gly Gln Tyr Gly Ser Gly Pro Gly Gln Gln Gly Pro Tyr Gly Pro
    2420                2425                2430

Gly Gln Ser Gly Ser Gly Gln Gln Gly Pro Gly Gln Gln Gly Pro
    2435                2440                2445

Tyr Ala Ser Ala Ala Ala Ala Ala Gly Pro Gly Ser Gly Gln
    2450                2455                2460

Gln Gly Pro Gly Ala Ser Ala Ala Ala Ala Ala Ala
    2465                2470                2475

<210> SEQ ID NO 3
<211> LENGTH: 595
<212> TYPE: PRT
<213> ORGANISM: Artificial Sequence
<220> FEATURE:
<223> OTHER INFORMATION: PRT647

<400> SEQUENCE: 3

Met His His His His His His Ser Ser Gly Ser Ser Thr Thr Met Asn
1               5                   10                  15

Trp Ser Thr Arg Leu Val Leu Ser Ile Leu Val Val Leu Cys Thr Gln
            20                  25                  30

Ser Leu Cys Ala Leu Gly Gln Ala Asn Thr Pro Trp Ser Ser Lys Glu
        35                  40                  45

Asn Ala Asp Ala Phe Ile Gly Ala Phe Met Asn Ala Ala Ser Gln Ser
    50                  55                  60

Gly Ala Phe Ser Ser Asp Gln Ile Asp Asp Met Ser Val Ile Ser Asn
65                  70                  75                  80

Thr Leu Met Ala Ala Met Asp Asn Met Gly Gly Arg Ile Thr Gln Ser
                85                  90                  95

Lys Leu Gln Ala Leu Asp Met Ala Phe Ala Ser Ser Val Ala Glu Ile
            100                 105                 110

Ala Val Ala Asp Gly Gln Asn Val Gly Ala Ala Thr Asn Ala Ile Ser
        115                 120                 125

Asp Ala Leu Arg Ser Ala Phe Tyr Gln Thr Thr Gly Val Val Asn Asn
    130                 135                 140

Gln Phe Ile Thr Gly Ile Ser Ser Leu Ile Gly Met Phe Ala Gln Val
145                 150                 155                 160

Ser Gly Asn Glu Val Ser Tyr Ser Ser Ala Gly Ser Ser Ala Ala
                165                 170                 175
```

```
Ala Ser Glu Ala Val Ser Ala Gly Gln Gly Pro Ala Ala Gln Pro Val
            180                 185                 190

Tyr Ala Pro Ser Ala Ser Ala Ala Ala Ala Ala Ser Gly Ala Ala
        195                 200                 205

Pro Ala Ile Gln Gln Ala Tyr Glu Arg Gly Gly Ser Gly Ser Ala Ala
        210                 215                 220

Ala Ala Ala Gly Ser Gly Pro Ser Gly Tyr Gly Gln Gly Ala Gly Gly
225                 230                 235                 240

Pro Gly Gly Ala Gly Ala Ala Ala Ala Ala Ala Gly Gly Ser
            245                 250                 255

Gly Pro Gly Gly Tyr Gly Gln Gly Pro Ala Ala Tyr Gly Pro Ser Gly
            260                 265                 270

Pro Ser Gly Gln Gln Gly Tyr Gly Pro Gly Gly Ser Gly Ala Ala Ala
        275                 280                 285

Ala Ala Ala Ala Ala Gly Ser Gly Pro Ser Gly Tyr Gly Pro Gly
290                 295                 300

Ala Gly Gly Pro Gly Gly Ala Gly Ala Ala Ala Ala Ala Ala Ala
305                 310                 315                 320

Gly Gly Ser Gly Pro Gly Gly Tyr Gly Gln Gly Gln Ala Ser Tyr Gly
            325                 330                 335

Pro Ser Gly Pro Ser Gly Gln Gln Gly Tyr Gly Pro Gly Gly Ser Gly
            340                 345                 350

Ala Ala Ala Ala Ala Ala Ala Ala Gly Gly Pro Gly Phe Gly Gly
            355                 360                 365

Gln Gln Gly Tyr Gly Pro Gly Gly Ser Gly Ala Ala Ala Ala Ala
370                 375                 380

Ala Gly Gly Ala Gly Pro Gly Arg Gln Gln Ala Tyr Gly Pro Gly Gly
385                 390                 395                 400

Ser Gly Ala Ala Ala Ala Ala Ala Ala Gly Ser Gly Pro Ser
            405                 410                 415

Gly Tyr Gly Pro Ser Ala Ala Gly Pro Ser Pro Gly Gly Ser Gly
            420                 425                 430

Ala Ala Gly Gly Ser Gly Pro Gly Gly Phe Gly Gln Gly Pro Ala Gly
            435                 440                 445

Tyr Gly Pro Ser Gly Pro Gly Gln Gln Gly Tyr Gly Pro Gly Ala
        450                 455                 460

Ser Gly Ala Ala Ala Ala Ala Ala Ser Gly Ser Gly Gly Tyr Gly
465                 470                 475                 480

Pro Ser Gln Tyr Val Pro Ser Ser Val Ala Ser Ser Ala Ala Ser Ala
            485                 490                 495

Ala Ser Ala Leu Ser Ser Pro Thr Thr His Ala Arg Ile Ser Ser His
            500                 505                 510

Ala Ser Thr Leu Leu Ser Ser Gly Pro Thr Asn Ala Ala Ala Leu Ser
            515                 520                 525

Asn Val Ile Ser Asn Ala Val Ser Gln Val Ser Ala Ser Asn Pro Gly
        530                 535                 540

Ser Ser Ser Cys Asp Val Leu Val Gln Ala Leu Leu Glu Ile Ile Thr
545                 550                 555                 560

Ala Leu Ile Ser Ile Leu Asp Ser Ser Val Gly Gln Val Asn Tyr
            565                 570                 575

Gly Ser Ser Gly Gln Tyr Ala Gln Ile Val Gly Gln Ser Met Gln Gln
            580                 585                 590

Ala Met Gly
```

595

<210> SEQ ID NO 4
<211> LENGTH: 576
<212> TYPE: PRT
<213> ORGANISM: Artificial Sequence
<220> FEATURE:
<223> OTHER INFORMATION: PRT699

<400> SEQUENCE: 4

Met His His His His His Ser Ser Gly Ser Gly Pro Gly Val
1               5                   10                  15

Leu Gly Pro Tyr Gly Pro Gly Ala Ser Ala Ala Ala Ala Ala
                20                  25                  30

Gly Ser Asn Gly Pro Gly Ser Gly Val Leu Gly Pro Gln Ser Gly
            35                  40                  45

Gln Tyr Gly Pro Gly Val Leu Gly Pro Gly Val Leu Gly Pro Gly Ser
    50                  55                  60

Ser Ala Ala Ala Ala Ala Ala Gly Pro Gly Gln Tyr Gly Pro Gly
65                  70                  75                  80

Val Leu Gly Pro Ser Ala Ser Ala Ala Ala Ala Ala Ala Gly Pro
                85                  90                  95

Gly Ser Gly Val Leu Gly Pro Gly Ala Ser Gly Gln Tyr Gly Pro Gly
            100                 105                 110

Val Leu Gly Pro Gly Val Leu Gly Pro Gly Ser Ser Ala Ala Ala
                115                 120                 125

Ala Ala Ala Gly Ser Tyr Gly Ser Gly Pro Gly Val Leu Gly Pro Tyr
130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Val Leu Gly Pro Ser Ala Ser Ala Ala Ala Ala Ala Ala
                180                 185                 190

Gly Ser Gly Val Leu Gly Pro Gly Gln Tyr Gly Pro Tyr Ala Ser Ala
            195                 200                 205

Ala Ala Ala Ala Ala Gly Ser Tyr Gly Ser Gly Pro Gly Val Leu
210                 215                 220

Gly Pro Tyr Gly Pro Gly Gln Ser Gly Ser Gly Val Leu Gly Pro Gly
225                 230                 235                 240

Val Leu Gly Pro Tyr Ala Ser Ala Ala Ala Ala Ala Ala Gly Pro
                245                 250                 255

Gly Val Leu Gly Pro Tyr Gly Pro Gly Ser Ser Ala Ala Ala Ala
            260                 265                 270

Ala Ala Gly Ser Tyr Gly Tyr Gly Pro Gly Val Leu Gly Pro Tyr Gly
275                 280                 285

Pro Gly Ala Ser Gly Gln Asn Gly Pro Gly Ser Gly Gln Tyr Gly Pro
    290                 295                 300

Gly Val Leu Gly Pro Gly Pro Ser Ala Ala Ala Ala Ala Ala Gly
305                 310                 315                 320

Pro Gly Val Leu Gly Pro Tyr Gly Pro Gly Ala Ser Ala Ala Ala Ala
                325                 330                 335

Ala Ala Ala Gly Ser Tyr Gly Pro Gly Val Leu Gly Pro Gly Gln Tyr
            340                 345                 350

Gly Pro Gly Ser Ser Gly Pro Gly Val Leu Gly Pro Tyr Gly Pro Gly

```
                355                 360                 365
Ser Ser Ala Ala Ala Ala Ala Ala Gly Ser Tyr Gly Pro Gly Val
    370                 375                 380

Leu Gly Pro Tyr Gly Pro Gly Pro Ser Ala Ala Ala Ala Ala Ala
385                 390                 395                 400

Gly Ser Tyr Val Leu Gly Pro Gly Val Leu Gly Pro Tyr Gly Pro Gly
                405                 410                 415

Ala Ser Gly Pro Gly Val Leu Gly Pro Tyr Gly Pro Gly Ala Ser Ala
            420                 425                 430

Ala Ala Ala Ala Ala Ala Gly Pro Gly Gln Tyr Gly Pro Gly Val Leu
        435                 440                 445

Gly Pro Ser Ala Ser Ala Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Val Leu Gly Gln Gly Pro Tyr Gly Pro Gly Ala Ser Ala
                485                 490                 495

Ala Ala Ala Ala Ala Gly Ser Tyr Gly Pro Gly Val Leu Gly Pro
            500                 505                 510

Tyr Gly Pro Gly Pro Ser Ala Ala Ala Ala Ala Ala Gly Pro Gly
        515                 520                 525

Ser Gly Gln Tyr Gly Pro Gly Ala Ser Gly Gln Asn Gly Pro Gly Ser
    530                 535                 540

Gly Gln Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
                565                 570                 575

<210> SEQ ID NO 5
<211> LENGTH: 576
<212> TYPE: PRT
<213> ORGANISM: Artificial Sequence
<220> FEATURE:
<223> OTHER INFORMATION: PRT698

<400> SEQUENCE: 5

Met His His His His His Ser Ser Gly Ser Ser Gly Pro Gly Val
1               5                   10                  15

Leu Gly Pro Tyr Gly Pro Gly Ala Ser Ala Ala Ala Ala Ala Ala
                20                  25                  30

Gly Ser Asn Gly Pro Gly Ser Gly Val Leu Gly Pro Gly Ile Ser Gly
            35                  40                  45

Ile Tyr Gly Pro Gly Val Leu Gly Pro Gly Val Leu Gly Pro Gly Ser
    50                  55                  60

Ser Ala Ala Ala Ala Ala Ala Gly Pro Gly Ile Tyr Gly Pro Gly
65                  70                  75                  80

Val Leu Gly Pro Ser Ala Ser Ala Ala Ala Ala Ala Ala Gly Pro
                85                  90                  95

Gly Ser Gly Val Leu Gly Pro Gly Ala Ser Gly Ile Tyr Gly Pro Gly
            100                 105                 110

Val Leu Gly Pro Gly Val Leu Gly Pro Gly Ser Ser Ala Ala Ala
        115                 120                 125

Ala Ala Ala Gly Ser Tyr Gly Ser Gly Pro Gly Val Leu Gly Pro Tyr
    130                 135                 140

Gly Ser Ala Ala Ala Ala Ala Ala Ala Gly Pro Gly Ser Gly Ile Tyr
```

```
            145                 150                 155                 160
Gly Ile Gly Pro Tyr Gly Pro Gly Ala Ser Gly Pro Gly Ile Tyr Gly
                    165                 170                 175
Pro Gly Val Leu Gly Pro Ser Ala Ser Ala Ala Ala Ala Ala Ala Ala
                180                 185                 190
Gly Ser Gly Val Leu Gly Pro Gly Ile Tyr Gly Pro Tyr Ala Ser Ala
            195                 200                 205
Ala Ala Ala Ala Ala Ala Gly Ser Tyr Gly Ser Gly Pro Gly Val Leu
        210                 215                 220
Gly Pro Tyr Gly Pro Gly Ile Ser Gly Ser Gly Val Leu Gly Pro Gly
225                 230                 235                 240
Val Leu Gly Pro Tyr Ala Ser Ala Ala Ala Ala Ala Ala Ala Gly Pro
                245                 250                 255
Gly Val Leu Gly Pro Tyr Gly Pro Gly Ser Ser Ala Ala Ala Ala Ala
            260                 265                 270
Ala Ala Gly Ser Tyr Gly Tyr Gly Pro Gly Val Leu Gly Pro Tyr Gly
        275                 280                 285
Pro Gly Ala Ser Gly Ile Asn Gly Pro Gly Ser Gly Ile Tyr Gly Pro
    290                 295                 300
Gly Val Leu Gly Pro Gly Pro Ser Ala Ala Ala Ala Ala Ala Ala Gly
305                 310                 315                 320
Pro Gly Val Leu Gly Pro Tyr Gly Pro Gly Ala Ser Ala Ala Ala Ala
                325                 330                 335
Ala Ala Ala Gly Ser Tyr Gly Pro Gly Val Leu Gly Pro Gly Ile Tyr
            340                 345                 350
Gly Pro Gly Ser Ser Gly Pro Gly Val Leu Gly Pro Tyr Gly Pro Gly
        355                 360                 365
Ser Ser Ala Ala Ala Ala Ala Ala Gly Ser Tyr Gly Pro Gly Val
    370                 375                 380
Leu Gly Pro Tyr Gly Pro Gly Pro Ser Ala Ala Ala Ala Ala Ala Ala
385                 390                 395                 400
Gly Ser Tyr Val Leu Gly Pro Gly Val Leu Gly Pro Tyr Gly Pro Gly
                405                 410                 415
Ala Ser Gly Pro Gly Val Leu Gly Pro Tyr Gly Pro Gly Ala Ser Ala
                420                 425                 430
Ala Ala Ala Ala Ala Gly Pro Gly Ile Tyr Gly Pro Gly Val Leu
        435                 440                 445
Gly Pro Ser Ala Ser Ala Ala Ala Ala Ala Gly Ser Tyr Gly
    450                 455                 460
Ser Gly Pro Gly Ile Tyr Gly Pro Tyr Gly Pro Gly Ile Ser Gly Pro
465                 470                 475                 480
Gly Ser Gly Val Leu Gly Ile Gly Pro Tyr Gly Pro Gly Ala Ser Ala
                485                 490                 495
Ala Ala Ala Ala Ala Gly Ser Tyr Gly Pro Gly Val Leu Gly Pro
            500                 505                 510
Tyr Gly Pro Gly Pro Ser Ala Ala Ala Ala Ala Ala Gly Pro Gly
        515                 520                 525
Ser Gly Ile Tyr Gly Pro Gly Ala Ser Gly Ile Asn Gly Pro Gly Ser
    530                 535                 540
Gly Ile Tyr Gly Pro Gly Val Leu Gly Pro Gly Pro Ser Ala Ala Ala
545                 550                 555                 560
Ala Ala Ala Ala Gly Pro Gly Ser Gly Val Leu Gly Pro Gly Ala Ser
                565                 570                 575
```

<210> SEQ ID NO 6
<211> LENGTH: 252
<212> TYPE: PRT
<213> ORGANISM: Artificial Sequence
<220> FEATURE:
<223> OTHER INFORMATION: Collagen-type4-Kai

<400> SEQUENCE: 6

```
Met His His His His His Ser Ser Gly Ser Ser Lys Asp Gly Val
1               5                   10                  15

Pro Gly Phe Pro Gly Ser Glu Gly Val Lys Gly Asn Arg Gly Phe Pro
            20                  25                  30

Gly Leu Met Gly Glu Asp Gly Ile Lys Gly Gln Lys Gly Asp Ile Gly
        35                  40                  45

Pro Pro Gly Phe Arg Gly Pro Thr Glu Tyr Tyr Asp Thr Tyr Gln Glu
    50                  55                  60

Lys Gly Asp Glu Gly Thr Pro Gly Pro Pro Gly Arg Gly Ala Arg
65                  70                  75                  80

Gly Pro Gln Gly Pro Ser Gly Pro Gly Val Pro Gly Ser Pro Gly
                85                  90                  95

Ser Ser Arg Pro Gly Leu Arg Gly Ala Pro Gly Trp Pro Gly Leu Lys
            100                 105                 110

Gly Ser Lys Gly Glu Arg Gly Arg Pro Gly Lys Asp Ala Met Gly Thr
        115                 120                 125

Pro Gly Ser Pro Gly Cys Ala Gly Ser Pro Gly Leu Pro Gly Ser Pro
    130                 135                 140

Gly Pro Pro Gly Pro Pro Gly Asp Ile Val Phe Arg Lys Gly Pro Pro
145                 150                 155                 160

Gly Asp His Gly Leu Pro Gly Tyr Leu Gly Ser Pro Gly Ile Pro Gly
                165                 170                 175

Val Asp Gly Pro Lys Gly Glu Pro Gly Leu Leu Cys Thr Gln Cys Pro
            180                 185                 190

Tyr Ile Pro Gly Pro Pro Gly Leu Pro Gly Leu Pro Gly Leu His Gly
        195                 200                 205

Val Lys Gly Ile Pro Gly Arg Gln Gly Ala Ala Gly Leu Lys Gly Ser
    210                 215                 220

Pro Gly Ser Pro Gly Asn Thr Gly Leu Pro Gly Phe Pro Gly Phe Pro
225                 230                 235                 240

Gly Ala Gln Gly Asp Pro Gly Leu Lys Gly Glu Lys
                245                 250
```

<210> SEQ ID NO 7
<211> LENGTH: 315
<212> TYPE: PRT
<213> ORGANISM: Artificial Sequence
<220> FEATURE:
<223> OTHER INFORMATION: Resilin-Kai

<400> SEQUENCE: 7

```
Met His His His His His Ser Ser Gly Ser Ser Pro Glu Pro Pro
1               5                   10                  15

Val Asn Ser Tyr Leu Pro Pro Ser Asp Ser Tyr Gly Ala Pro Gly Gln
            20                  25                  30

Ser Gly Pro Gly Gly Arg Pro Ser Asp Ser Tyr Gly Ala Pro Gly Gly
        35                  40                  45

Gly Asn Gly Gly Arg Pro Ser Asp Ser Tyr Gly Ala Pro Gly Gln Gly
```

```
              50                  55                  60
Gln Gly Gln Gly Gln Gly Gly Gly Tyr Ala Gly Lys Pro Ser Asp
 65                  70                  75                  80

Ser Tyr Gly Ala Pro Gly Gly Asp Gly Asn Gly Arg Pro Ser
                 85                  90                  95

Ser Ser Tyr Gly Ala Pro Gly Gly Asn Gly Gly Arg Pro Ser Asp
                    100                 105                 110

Thr Tyr Gly Ala Pro Gly Gly Asn Gly Gly Arg Pro Ser Asp Thr
                    115                 120                 125

Tyr Gly Ala Pro Gly Gly Gly Asn Gly Asn Gly Arg Pro Ser
    130                 135                 140

Ser Ser Tyr Gly Ala Pro Gly Gln Gly Gln Gly Asn Gly Asn Gly
145                 150                 155                 160

Arg Pro Ser Ser Ser Tyr Gly Ala Pro Gly Gly Asn Gly Gly Arg
                    165                 170                 175

Pro Ser Asp Thr Tyr Gly Ala Pro Gly Gly Asn Gly Gly Arg Pro
                180                 185                 190

Ser Asp Thr Tyr Gly Ala Pro Gly Gly Asn Asn Gly Gly Arg Pro
            195                 200                 205

Ser Ser Ser Tyr Gly Ala Pro Gly Gly Asn Gly Gly Arg Pro Ser
210                 215                 220

Asp Thr Tyr Gly Ala Pro Gly Gly Asn Gly Asn Gly Ser Gly Gly
225                 230                 235                 240

Arg Pro Ser Ser Ser Tyr Gly Ala Pro Gly Gln Gly Gln Gly Phe
                    245                 250                 255

Gly Gly Arg Pro Ser Asp Ser Tyr Gly Ala Pro Gly Gln Asn Gln Lys
            260                 265                 270

Pro Ser Asp Ser Tyr Gly Ala Pro Gly Ser Gly Asn Gly Asn Gly Gly
                275                 280                 285

Arg Pro Ser Ser Tyr Gly Ala Pro Gly Ser Gly Pro Gly Gly Arg
    290                 295                 300

Pro Ser Asp Ser Tyr Gly Pro Pro Ala Ser Gly
305                 310                 315

<210> SEQ ID NO 8
<211> LENGTH: 282
<212> TYPE: PRT
<213> ORGANISM: Artificial Sequence
<220> FEATURE:
<223> OTHER INFORMATION: elastin short

<400> SEQUENCE: 8

Met His His His His His Ser Ser Gly Ser Ser Leu Gly Val Ser
 1               5                  10                  15

Ala Gly Ala Val Val Pro Gln Pro Gly Ala Gly Val Lys Pro Gly Lys
                20                  25                  30

Val Pro Gly Val Gly Leu Pro Gly Val Tyr Pro Gly Gly Val Leu Pro
                35                  40                  45

Gly Ala Arg Phe Pro Gly Val Gly Val Leu Pro Gly Val Pro Thr Gly
    50                  55                  60

Ala Gly Val Lys Pro Lys Ala Pro Gly Val Gly Ala Phe Ala Gly
 65                  70                  75                  80

Ile Pro Gly Val Gly Pro Phe Gly Gly Pro Gln Pro Gly Val Pro Leu
                85                  90                  95

Gly Tyr Pro Ile Lys Ala Pro Lys Leu Pro Gly Gly Tyr Gly Leu Pro
```

```
            100                 105                 110
Tyr Thr Thr Gly Lys Leu Pro Tyr Gly Tyr Gly Pro Gly Gly Val Ala
        115                 120                 125
Gly Ala Ala Gly Lys Ala Gly Tyr Pro Thr Gly Thr Gly Val Gly Pro
        130                 135                 140
Gln Ala Ala Ala Ala Ala Ala Lys Ala Ala Ala Lys Phe Gly Ala
145                 150                 155                 160
Gly Ala Ala Gly Val Leu Pro Gly Val Gly Ala Gly Val Pro Gly
                165                 170                 175
Val Pro Gly Ala Ile Pro Gly Ile Gly Ile Ala Gly Val Gly Thr
            180                 185                 190
Pro Ala Ala Ala Ala Ala Ala Ala Ala Lys Ala Ala Lys Tyr
        195                 200                 205
Gly Ala Ala Ala Gly Leu Val Pro Gly Pro Gly Phe Gly Pro Gly
        210                 215                 220
Val Val Gly Val Pro Gly Ala Gly Val Pro Gly Val Gly Val Pro Gly
225                 230                 235                 240
Ala Gly Ile Pro Val Val Pro Gly Ala Gly Ile Pro Gly Ala Ala Val
                245                 250                 255
Pro Gly Val Val Ser Pro Glu Ala Ala Lys Ala Ala Lys Ala
                260                 265                 270
Ala Lys Tyr Gly Ala Arg Pro Gly Val Gly
        275                 280

<210> SEQ ID NO 9
<211> LENGTH: 468
<212> TYPE: PRT
<213> ORGANISM: Artificial Sequence
<220> FEATURE:
<223> OTHER INFORMATION: type I keratin 26

<400> SEQUENCE: 9

Met Ser Phe Arg Leu Ser Gly Val Ser Arg Arg Leu Cys Ser Gln Ala
1               5                   10                  15
Gly Thr Gly Arg Leu Thr Gly Gly Arg Thr Gly Phe Arg Ala Gly Asn
            20                  25                  30
Val Cys Ser Gly Leu Gly Ala Gly Ser Ser Phe Ser Gly Pro Leu Gly
        35                  40                  45
Ser Val Ser Ser Lys Gly Ser Phe Ser His Gly Gly Gly Leu Gly
    50                  55                  60
Ser Gly Val Cys Thr Gly Phe Leu Glu Asn Glu His Gly Leu Leu Pro
65                  70                  75                  80
Gly Asn Glu Lys Val Thr Leu Gln Asn Leu Asn Asp Arg Leu Ala Ser
                85                  90                  95
Tyr Leu Asp His Val Cys Thr Leu Glu Glu Ala Asn Ala Asp Leu Glu
            100                 105                 110
Gln Lys Ile Lys Gly Trp Tyr Glu Lys Tyr Gly Pro Gly Ser Gly Arg
        115                 120                 125
Gln Leu Ala His Asp Tyr Ser Lys Tyr Phe Ser Val Thr Glu Asp Leu
        130                 135                 140
Lys Arg Gln Ile Ile Ser Val Thr Thr Cys Asn Ala Ser Ile Val Leu
145                 150                 155                 160
Gln Asn Glu Asn Ala Arg Leu Thr Ala Asp Asp Phe Arg Leu Lys Cys
                165                 170                 175
Glu Asn Glu Leu Ala Leu His Gln Ser Val Glu Ala Asp Ile Asn Gly
```

```
                    180                 185                 190
Leu His Arg Val Met Asp Glu Leu Thr Leu Cys Thr Ser Asp Leu Glu
            195                 200                 205
Met Gln Cys Glu Ala Leu Ser Glu Glu Leu Thr Tyr Leu Lys Lys Asn
        210                 215                 220
His Gln Glu Glu Met Lys Val Met Gln Gly Ala Ala Arg Gly Asn Val
225                 230                 235                 240
Asn Val Glu Ile Asn Ala Ala Pro Gly Val Asp Leu Thr Val Leu Leu
                245                 250                 255
Asn Asn Met Arg Ala Glu Tyr Glu Asp Leu Ala Glu Gln Asn His Glu
            260                 265                 270
Asp Ala Glu Ala Trp Phe Ser Glu Lys Ser Thr Ser Leu His Gln Gln
        275                 280                 285
Ile Ser Asp Asp Ala Gly Ala Ala Met Ala Ala Arg Asn Glu Leu Met
        290                 295                 300
Glu Leu Lys Arg Asn Leu Gln Thr Leu Glu Ile Glu Leu Gln Ser Leu
305                 310                 315                 320
Leu Ala Met Lys His Ser Tyr Glu Cys Ser Leu Ala Glu Thr Glu Ser
                325                 330                 335
Asn Tyr Cys His Gln Leu Gln Gln Ile Gln Glu Gln Ile Gly Ala Met
            340                 345                 350
Glu Asp Gln Leu Gln Gln Ile Arg Met Glu Thr Glu Gly Gln Lys Leu
        355                 360                 365
Glu His Glu Arg Leu Leu Asp Val Lys Ile Phe Leu Glu Lys Glu Ile
        370                 375                 380
Glu Met Tyr Cys Lys Leu Ile Asp Gly Glu Gly Arg Lys Ser Lys Ser
385                 390                 395                 400
Thr Cys Tyr Lys Ser Glu Gly Arg Gly Pro Lys Asn Ser Glu Asn Gln
                405                 410                 415
Val Lys Asp Ser Lys Glu Glu Ala Val Val Lys Thr Val Gly Glu
            420                 425                 430
Leu Asp Gln Leu Gly Ser Val Leu Ser Leu Arg Val His Ser Val Glu
        435                 440                 445
Glu Lys Ser Ser Lys Ile Ser Asn Ile Thr Met Glu Gln Arg Leu Pro
        450                 455                 460
Ser Lys Val Pro
465

<210> SEQ ID NO 10
<211> LENGTH: 36
<212> TYPE: PRT
<213> ORGANISM: Artificial Sequence
<220> FEATURE:
<223> OTHER INFORMATION: HisTag

<400> SEQUENCE: 10

Met Glu Thr His Ile Ser His Ile Ser His Ile Ser His Ile Ser His
1               5                   10                  15

Ile Ser His Ile Ser Ser Glu Arg Ser Glu Arg Gly Leu Tyr Ser Glu
            20                  25                  30

Arg Ser Glu Arg
        35

<210> SEQ ID NO 11
<211> LENGTH: 2375
<212> TYPE: PRT
```

-continued

<213> ORGANISM: Artificial Sequence
<220> FEATURE:
<223> OTHER INFORMATION: PRT799

<400> SEQUENCE: 11

Met His His His His His Ser Ser Gly Ser Ser Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gly Pro Gly Gln Ser Gly Gln Tyr
            35                  40                  45

Gly Pro Gly Gln Gln Gly Pro Gly Gln Gln Gly Pro Gly Ser Ser Ala
50                      55                  60

Ala Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
            85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
            115                 120                 125

Gly Pro Gly Gln Gln Gly Pro Tyr Gly Ser Ala Ala Ala Ala Gly
            130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
            165                 170                 175

Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
            195                 200                 205

Gln Gln Gly Pro Tyr Gly Pro Gly Gln Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
            245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
            275                 280                 285

Gln Gly Pro Gly Gln Ser Ala Ala Ala Ala Gly Pro Gly Gln Gln
            290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
            325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
            355                 360                 365

Ser Ala Ala Ala Ala Gly Gln Tyr Gln Gly Pro Gly Gln Gln
            370                 375                 380

Gly Pro Tyr Gly Pro Gly Ala Ser Gly Pro Gly Gln Gln Gly Pro Tyr

```
            385                 390                 395                 400
Gly Pro Gly Ala Ser Ala Ala Ala Ala Gly Pro Gly Gln Tyr Gly
                    405                 410                 415
Pro Gly Gln Gln Gly Pro Ser Ala Ser Ala Ala Ala Ala Gly Gln
                    420                 425                 430
Tyr Gly Ser Gly Pro Gly Gln Tyr Gly Pro Tyr Gly Pro Gly Ser
                    435                 440                 445
Gly Pro Gly Ser Gly Gln Gln Gly Gln Gly Pro Tyr Gly Pro Gly Ala
            450                 455                 460
Ser Ala Ala Ala Ala Gly Gln Tyr Gly Pro Gly Gln Gln Gly Pro
465                 470                 475                 480
Tyr Gly Pro Gly Gln Ser Ala Ala Ala Ala Gly Pro Gly Ser Gly
                    485                 490                 495
Gln Tyr Gly Pro Gly Ala Ser Gly Gln Asn Gly Pro Gly Ser Gly Gln
                500                 505                 510
Tyr Gly Pro Gly Gln Gln Gly Pro Gly Gln Ser Ala Ala Ala Ala
                    515                 520                 525
Gly Gln Tyr Gln Gln Gly Pro Gly Gln Gly Pro Tyr Gly Pro Gly
            530                 535                 540
Ala Ser Ala Ala Ala Ala Gly Gln Tyr Gly Ser Gly Pro Gly Gln
545                 550                 555                 560
Gln Gly Pro Tyr Gly Pro Gly Gln Ser Gly Ser Gly Gln Gln Gly Pro
                    565                 570                 575
Gly Gln Gln Gly Pro Tyr Ala Ser Ala Ala Ala Ala Gly Pro Gly
                    580                 585                 590
Ser Gly Gln Gln Gly Pro Gly Ala Ser Gly Gln Gln Gly Pro Tyr Gly
            595                 600                 605
Pro Gly Ala Ser Ala Ala Ala Ala Gly Gln Asn Gly Pro Gly Ser
            610                 615                 620
Gly Gln Gln Gly Pro Gly Gln Ser Gly Gln Tyr Gly Pro Gly Gln Gln
625                 630                 635                 640
Gly Pro Gly Gln Gln Gly Pro Gly Ser Ser Ala Ala Ala Ala Gly
                    645                 650                 655
Pro Gly Gln Tyr Gly Pro Gly Gln Gln Gly Pro Ser Ala Ser Ala Ala
                    660                 665                 670
Ala Ala Ala Gly Pro Gly Ser Gly Gln Gln Gly Pro Gly Ala Ser Gly
            675                 680                 685
Gln Tyr Gly Pro Gly Gln Gln Gly Pro Gly Gln Gln Gly Pro Gly Ser
            690                 695                 700
Ser Ala Ala Ala Ala Gly Gln Tyr Gly Ser Gly Pro Gly Gln Gln
705                 710                 715                 720
Gly Pro Tyr Gly Ser Ala Ala Ala Ala Gly Pro Gly Ser Gly Gln
                    725                 730                 735
Tyr Gly Gln Gly Pro Tyr Gly Pro Gly Ala Ser Gly Pro Gly Gln Tyr
                740                 745                 750
Gly Pro Gly Gln Gln Gly Pro Ser Ala Ser Ala Ala Ala Ala Gly
                    755                 760                 765
Ser Gly Gln Gln Gly Pro Gly Gln Tyr Gly Pro Tyr Ala Ser Ala Ala
            770                 775                 780
Ala Ala Ala Gly Gln Tyr Gly Ser Gly Pro Gly Gln Gln Gly Pro Tyr
785                 790                 795                 800
Gly Pro Gly Gln Ser Gly Ser Gly Gln Gln Gly Pro Gly Gln Gln Gly
                    805                 810                 815
```

Pro Tyr Ala Ser Ala Ala Ala Ala Gly Pro Gly Gln Gln Gly Pro
                820                 825                 830

Tyr Gly Pro Gly Ser Ser Ala Ala Ala Ala Gly Gln Tyr Gly Tyr
                835                 840                 845

Gly Pro Gly Gln Gln Gly Pro Tyr Gly Pro Gly Ala Ser Gly Gln Asn
    850                 855                 860

Gly Pro Gly Ser Gly Gln Tyr Gly Pro Gly Gln Gln Gly Pro Gly Gln
865                 870                 875                 880

Ser Ala Ala Ala Ala Ala Gly Pro Gln Gln Gly Pro Tyr Gly Pro
                885                 890                 895

Gly Ala Ser Ala Ala Ala Ala Gly Gln Tyr Gly Pro Gly Gln Gln
                900                 905                 910

Gly Pro Gly Gln Tyr Gly Pro Gly Ser Ser Gly Pro Gly Gln Gln Gly
                915                 920                 925

Pro Tyr Gly Pro Gly Ser Ser Ala Ala Ala Ala Gly Gln Tyr Gly
    930                 935                 940

Pro Gly Gln Gln Gly Pro Tyr Gly Pro Gly Gln Ser Ala Ala Ala Ala
945                 950                 955                 960

Ala Gly Gln Tyr Gln Gln Gly Pro Gly Gln Gly Pro Tyr Gly Pro
        965                 970                 975

Gly Ala Ser Gly Pro Gly Gln Gln Gly Pro Tyr Gly Pro Gly Ala Ser
        980                 985                 990

Ala Ala Ala Ala Ala Gly Pro Gly Gln Tyr Gly Pro Gly Gln Gln Gly
        995                 1000                1005

Pro Ser Ala Ser Ala Ala Ala Ala Ala Gly Gln Tyr Gly Ser Gly
    1010                1015                1020

Pro Gly Gln Tyr Gly Pro Tyr Gly Pro Gly Gln Ser Gly Pro Gly
    1025                1030                1035

Ser Gly Gln Gln Gly Gln Gly Pro Tyr Gly Pro Gly Ala Ser Ala
    1040                1045                1050

Ala Ala Ala Ala Gly Gln Tyr Gly Pro Gly Gln Gln Gly Pro Tyr
    1055                1060                1065

Gly Pro Gly Gln Ser Ala Ala Ala Ala Gly Pro Gly Ser Gly
    1070                1075                1080

Gln Tyr Gly Pro Gly Ala Ser Gly Gln Asn Gly Pro Gly Ser Gly
    1085                1090                1095

Gln Tyr Gly Pro Gly Gln Gln Gly Pro Gly Gln Ser Ala Ala Ala
    1100                1105                1110

Ala Ala Gly Gln Tyr Gln Gln Gly Pro Gly Gln Gln Gly Pro Tyr
    1115                1120                1125

Gly Pro Gly Ala Ser Ala Ala Ala Ala Ala Gly Gln Tyr Gly Ser
    1130                1135                1140

Gly Pro Gly Gln Gln Gly Pro Tyr Gly Pro Gly Gln Ser Gly Ser
    1145                1150                1155

Gly Gln Gln Gly Pro Gly Gln Gln Gly Pro Tyr Ala Ser Ala Ala
    1160                1165                1170

Ala Ala Ala Gly Pro Gly Ser Gly Gln Gln Gly Pro Gly Ala Ser
    1175                1180                1185

Gly Gln Gln Gly Pro Tyr Gly Pro Gly Ala Ser Ala Ala Ala Ala
    1190                1195                1200

Ala Gly Gln Asn Gly Pro Gly Ser Gly Gln Gln Gly Pro Gly Gln
    1205                1210                1215

Ser Gly Gln Tyr Gly Pro Gly Gln Gln Gly Gln Gln Gly
1220             1225             1230

Pro Gly Ser Ser Ala Ala Ala Ala Ala Gly Pro Gly Gln Tyr Gly
        1235             1240             1245

Pro Gly Gln Gln Gly Pro Ser Ala Ser Ala Ala Ala Ala Gly
1250             1255             1260

Pro Gly Ser Gly Gln Gln Gly Pro Gly Ala Ser Gly Gln Tyr Gly
        1265             1270             1275

Pro Gly Gln Gln Gly Pro Gly Gln Gln Gly Pro Gly Ser Ser Ala
1280             1285             1290

Ala Ala Ala Ala Gly Gln Tyr Gly Ser Gly Pro Gly Gln Gln Gly
1295             1300             1305

Pro Tyr Gly Ser Ala Ala Ala Ala Gly Pro Gly Ser Gly Gln
1310             1315             1320

Tyr Gly Gln Gly Pro Tyr Gly Pro Gly Ala Ser Gly Pro Gly Gln
1325             1330             1335

Tyr Gly Pro Gly Gln Gln Gly Pro Ser Ala Ser Ala Ala Ala
1340             1345             1350

Ala Gly Ser Gly Gln Gln Gly Pro Gly Gln Tyr Gly Pro Tyr Ala
1355             1360             1365

Ser Ala Ala Ala Ala Gly Gln Tyr Gly Ser Gly Pro Gly Gln
1370             1375             1380

Gln Gly Pro Tyr Gly Pro Gly Gln Ser Gly Ser Gly Gln Gln Gly
1385             1390             1395

Pro Gly Gln Gln Gly Pro Tyr Ala Ser Ala Ala Ala Ala Gly
1400             1405             1410

Pro Gly Gln Gln Gly Pro Tyr Gly Pro Gly Ser Ser Ala Ala Ala
1415             1420             1425

Ala Ala Gly Gln Tyr Gly Tyr Gly Pro Gly Gln Gln Gly Pro Tyr
1430             1435             1440

Gly Pro Gly Ala Ser Gly Gln Asn Gly Pro Gly Ser Gly Gln Tyr
1445             1450             1455

Gly Pro Gly Gln Gln Gly Pro Gly Gln Ser Ala Ala Ala Ala
1460             1465             1470

Gly Pro Gly Gln Gln Gly Pro Tyr Gly Pro Gly Ala Ser Ala Ala
1475             1480             1485

Ala Ala Ala Gly Gln Tyr Gly Pro Gly Gln Gln Gly Pro Gly Gln
1490             1495             1500

Tyr Gly Pro Gly Ser Ser Gly Pro Gly Gln Gln Gly Pro Tyr Gly
1505             1510             1515

Pro Gly Ser Ser Ala Ala Ala Ala Ala Gly Gln Tyr Gly Pro Gly
1520             1525             1530

Gln Gln Gly Pro Tyr Gly Pro Gly Gln Ser Ala Ala Ala Ala Ala
1535             1540             1545

Gly Gln Tyr Gln Gln Gly Pro Gly Gln Gln Gly Pro Tyr Gly Pro
1550             1555             1560

Gly Ala Ser Gly Pro Gly Gln Gln Gly Pro Tyr Gly Pro Gly Ala
1565             1570             1575

Ser Ala Ala Ala Ala Ala Gly Pro Gly Gln Tyr Gly Pro Gly Gln
1580             1585             1590

Gln Gly Pro Ser Ala Ser Ala Ala Ala Ala Gly Gln Tyr Gly
1595             1600             1605

Ser Gly Pro Gly Gln Tyr Gly Pro Tyr Gly Pro Gly Gln Ser Gly

-continued

```
            1610                1615                1620
Pro Gly Ser Gly Gln Gln Gly Gln Gly Pro Tyr Gly Pro Gly Ala
            1625                1630                1635
Ser Ala Ala Ala Ala Ala Gly Gln Tyr Gly Pro Gly Gln Gln Gly
            1640                1645                1650
Pro Tyr Gly Pro Gly Gln Ser Ala Ala Ala Ala Gly Pro Gly
            1655                1660                1665
Ser Gly Gln Tyr Gly Pro Gly Ala Ser Gly Gln Asn Gly Pro Gly
            1670                1675                1680
Ser Gly Gln Tyr Gly Pro Gly Gln Gln Gly Pro Gly Gln Ser Ala
            1685                1690                1695
Ala Ala Ala Ala Gly Gln Tyr Gln Gln Gly Pro Gly Gln Gln Gly
            1700                1705                1710
Pro Tyr Gly Pro Gly Ala Ser Ala Ala Ala Ala Gly Gln Tyr
            1715                1720                1725
Gly Ser Gly Pro Gly Gln Gln Gly Pro Tyr Gly Pro Gly Gln Ser
            1730                1735                1740
Gly Ser Gly Gln Gln Gly Pro Gly Gln Gln Gly Pro Tyr Ala Ser
            1745                1750                1755
Ala Ala Ala Ala Gly Pro Gly Ser Gly Gln Gln Gly Pro Gly
            1760                1765                1770
Ala Ser Gly Gln Gln Gly Pro Tyr Gly Pro Gly Ala Ser Ala Ala
            1775                1780                1785
Ala Ala Ala Gly Gln Asn Gly Pro Gly Ser Gly Gln Gln Gly Pro
            1790                1795                1800
Gly Gln Ser Gly Gln Tyr Gly Pro Gly Gln Gln Gly Pro Gly Gln
            1805                1810                1815
Gln Gly Pro Gly Ser Ser Ala Ala Ala Ala Gly Pro Gly Gln
            1820                1825                1830
Tyr Gly Pro Gly Gln Gln Gly Pro Ser Ala Ser Ala Ala Ala Ala
            1835                1840                1845
Ala Gly Pro Gly Ser Gly Gln Gln Gly Pro Gly Ala Ser Gly Gln
            1850                1855                1860
Tyr Gly Pro Gly Gln Gln Gly Pro Gly Gln Gln Gly Pro Gly Ser
            1865                1870                1875
Ser Ala Ala Ala Ala Gly Gln Tyr Gly Ser Gly Pro Gly Gln
            1880                1885                1890
Gln Gly Pro Tyr Gly Ser Ala Ala Ala Ala Gly Pro Gly Ser
            1895                1900                1905
Gly Gln Tyr Gly Gln Gly Pro Tyr Gly Pro Gly Ala Ser Gly Pro
            1910                1915                1920
Gly Gln Tyr Gly Pro Gly Gln Gln Gly Pro Ser Ala Ser Ala Ala
            1925                1930                1935
Ala Ala Ala Gly Ser Gly Gln Gln Gly Pro Gly Gln Tyr Gly Pro
            1940                1945                1950
Tyr Ala Ser Ala Ala Ala Ala Gly Gln Tyr Gly Ser Gly Pro
            1955                1960                1965
Gly Gln Gln Gly Pro Tyr Gly Pro Gly Gln Ser Gly Ser Gly Gln
            1970                1975                1980
Gln Gly Pro Gly Gln Gln Gly Pro Tyr Ala Ser Ala Ala Ala
            1985                1990                1995
Ala Gly Pro Gly Gln Gln Gly Pro Tyr Gly Pro Gly Ser Ser Ala
            2000                2005                2010
```

Ala Ala Ala Ala Gly Gln Tyr Gly Tyr Gly Pro Gly Gln Gln Gly
         2015                2020                2025

Pro Tyr Gly Pro Gly Ala Ser Gly Gln Asn Gly Pro Gly Ser Gly
        2030                2035                2040

Gln Tyr Gly Pro Gly Gln Gln Gly Pro Gly Gln Ser Ala Ala Ala
        2045                2050                2055

Ala Ala Gly Pro Gly Gln Gln Gly Pro Tyr Gly Pro Gly Ala Ser
        2060                2065                2070

Ala Ala Ala Ala Ala Gly Gln Tyr Gly Pro Gly Gln Gln Gly Pro
        2075                2080                2085

Gly Gln Tyr Gly Pro Gly Ser Ser Gly Pro Gly Gln Gln Gly Pro
        2090                2095                2100

Tyr Gly Pro Gly Ser Ser Ala Ala Ala Ala Gly Gln Tyr Gly
        2105                2110                2115

Pro Gly Gln Gln Gly Pro Tyr Gly Pro Gly Gln Ser Ala Ala Ala
        2120                2125                2130

Ala Ala Gly Gln Tyr Gln Gln Gly Pro Gly Gln Gln Gly Pro Tyr
        2135                2140                2145

Gly Pro Gly Ala Ser Gly Pro Gly Gln Gln Gly Pro Tyr Gly Pro
        2150                2155                2160

Gly Ala Ser Ala Ala Ala Ala Gly Pro Gly Gln Tyr Gly Pro
        2165                2170                2175

Gly Gln Gln Gly Pro Ser Ala Ser Ala Ala Ala Ala Gly Gln
        2180                2185                2190

Tyr Gly Ser Gly Pro Gly Gln Tyr Gly Pro Tyr Gly Pro Gly Gln
        2195                2200                2205

Ser Gly Pro Gly Ser Gly Gln Gln Gly Gln Gly Pro Tyr Gly Pro
        2210                2215                2220

Gly Ala Ser Ala Ala Ala Ala Gly Gln Tyr Gly Pro Gly Gln
        2225                2230                2235

Gln Gly Pro Tyr Gly Pro Gly Gln Ser Ala Ala Ala Ala Ala Gly
        2240                2245                2250

Pro Gly Ser Gly Gln Tyr Gly Pro Gly Ala Ser Gly Gln Asn Gly
        2255                2260                2265

Pro Gly Ser Gly Gln Tyr Gly Pro Gly Gln Gln Gly Pro Gly Gln
        2270                2275                2280

Ser Ala Ala Ala Ala Gly Gln Tyr Gln Gln Gly Pro Gly Gln
        2285                2290                2295

Gln Gly Pro Tyr Gly Pro Gly Ala Ser Ala Ala Ala Ala Gly
        2300                2305                2310

Gln Tyr Gly Ser Gly Pro Gly Gln Gln Gly Pro Tyr Gly Pro Gly
        2315                2320                2325

Gln Ser Gly Ser Gly Gln Gln Gly Pro Gly Gln Gln Gly Pro Tyr
        2330                2335                2340

Ala Ser Ala Ala Ala Ala Ala Gly Pro Gly Ser Gly Gln Gln Gly
        2345                2350                2355

Ser Ser Val Asp Lys Leu Ala Ala Ala Leu Glu His His His
        2360                2365                2370

His His
2375

<210> SEQ ID NO 12
<211> LENGTH: 1188

<212> TYPE: PRT
<213> ORGANISM: Artificial Sequence
<220> FEATURE:
<223> OTHER INFORMATION: PRT587

<400> SEQUENCE: 12

```
Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
                20                  25                  30

Asn Gly Pro Gly Ser Gly Gln Gln Gly Pro Gly Gln Ser Gly Gln Tyr
                35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
                100                 105                 110

Gln Gly Pro Gly Ser Ser Ala Ala Ala Ala Gly Gln Tyr Gly Ser
                115                 120                 125

Gly Pro Gly Gln Gln Gly Pro Tyr Gly Ser Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Ala Gly Ser Gly Gln Gln Gly Pro Gly Gln Tyr Gly Pro
                180                 185                 190

Tyr Ala Ser Ala Ala Ala Ala Gly Gln Tyr Gly Ser Gly Pro Gly
                195                 200                 205

Gln Gln Gly Pro Tyr Gly Pro Gly Ser Gly Ser Gly Gln Gln Gly
                210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
                245                 250                 255

Gly Gln Tyr Gly Tyr Gly Pro Gly Gln Gln Gly Pro Tyr Gly Pro Gly
                260                 265                 270

Ala Ser Gly Gln Asn Gly Pro Gly Ser Gly Gln Tyr Gly Pro Gly Gln
                275                 280                 285

Gln Gly Pro Gly Gln Ser Ala Ala Ala Ala Gly Pro Gly Gln Gln
                290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala Ala
                340                 345                 350

Ala Gly Gln Tyr Gly Pro Gly Gln Gln Gly Pro Tyr Gly Pro Gly Gln
                355                 360                 365

Ser Ala Ala Ala Ala Ala Gly Gln Tyr Gln Gln Gly Pro Gly Gln Gln
                370                 375                 380
```

-continued

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
            405                 410                 415

Pro Gly Gln Gln Gly Pro Ser Ala Ser Ala Ala Ala Ala Gly Gln
                420                 425                 430

Tyr Gly Ser Gly Pro Gly Gln Tyr Gly Pro Tyr Gly Pro Gly Gln Ser
            435                 440                 445

Gly Pro Gly Ser Gly Gln Gln Gly Gln Gly Pro Tyr Gly Pro Gly Ala
        450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
            485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala
            515                 520                 525

Gly Gln Tyr Gln Gln Gly Pro Gly Gln Gln Gly Pro Tyr Gly Pro Gly
    530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser Gly Gln Gln Gly Pro Tyr Gly
            595                 600                 605

Pro Gly Ala Ser Ala Ala Ala Ala Gly Gln Asn Gly Pro Gly Ser
            610                 615                 620

Gly Gln Gln Gly Pro Gly Gln Ser Gly Gln Tyr Gly Pro Gly Gln Gln
625                 630                 635                 640

Gly Pro Gly Gln Gln Gly Pro Gly Ser Ser Ala Ala Ala Ala Gly
            645                 650                 655

Pro Gly Gln Tyr Gly Pro Gly Gln Gln Gly Pro Ser Ala Ser Ala Ala
            660                 665                 670

Ala Ala Ala Gly Pro Gly Ser Gly Gln Gln Gly Pro Gly Ala Ser Gly
        675                 680                 685

Gln Tyr Gly Pro Gly Gln Gln Gly Pro Gly Gln Gln Gly Pro Gly Ser
    690                 695                 700

Ser Ala Ala Ala Ala Gly Gln Tyr Gly Ser Gly Pro Gly Gln Gln
705                 710                 715                 720

Gly Pro Tyr Gly Ser Ala Ala Ala Ala Gly Pro Gly Ser Gly Gln
            725                 730                 735

Tyr Gly Gln Gly Pro Tyr Gly Pro Gly Ala Ser Gly Pro Gly Gln Tyr
            740                 745                 750

Gly Pro Gly Gln Gln Gly Pro Ser Ala Ser Ala Ala Ala Ala Gly
            755                 760                 765

Ser Gly Gln Gln Gly Pro Gly Gln Tyr Gly Pro Tyr Ala Ser Ala Ala
            770                 775                 780

Ala Ala Ala Gly Gln Tyr Gly Ser Gly Pro Gly Gln Gln Gly Pro Tyr
        785                 790                 795                 800

Gly Pro Gly Gln Ser Gly Ser Gly Gln Gln Gly Pro Gly Gln Gln Gly

```
                805              810             815
Pro Tyr Ala Ser Ala Ala Ala Ala Gly Pro Gly Gln Gln Gly Pro
            820             825             830

Tyr Gly Pro Gly Ser Ser Ala Ala Ala Ala Gly Gln Tyr Gly Tyr
            835             840             845

Gly Pro Gly Gln Gln Gly Pro Tyr Gly Pro Gly Ala Ser Gly Gln Asn
            850             855             860

Gly Pro Gly Ser Gly Gln Tyr Gly Pro Gly Gln Gln Gly Pro Gly Gln
865             870             875             880

Ser Ala Ala Ala Ala Gly Pro Gly Gln Gln Gly Pro Tyr Gly Pro
            885             890             895

Gly Ala Ser Ala Ala Ala Ala Gly Gln Tyr Gly Pro Gly Gln Gln
            900             905             910

Gly Pro Gly Gln Tyr Gly Pro Gly Ser Ser Gly Pro Gly Gln Gln Gly
            915             920             925

Pro Tyr Gly Pro Gly Ser Ser Ala Ala Ala Ala Gly Gln Tyr Gly
            930             935             940

Pro Gly Gln Gln Gly Pro Tyr Gly Pro Gly Gln Ser Ala Ala Ala
945             950             955             960

Ala Gly Gln Tyr Gln Gln Gly Pro Gly Gln Gln Gly Pro Tyr Gly Pro
            965             970             975

Gly Ala Ser Gly Pro Gly Gln Gln Gly Pro Tyr Gly Pro Gly Ala Ser
            980             985             990

Ala Ala Ala Ala Ala Gly Pro Gly Gln Tyr Gly Pro Gly Gln Gln Gly
            995             1000            1005

Pro Ser Ala Ser Ala Ala Ala Ala Gly Gln Tyr Gly Ser Gly
            1010            1015            1020

Pro Gly Gln Tyr Gly Pro Tyr Gly Pro Gly Gln Ser Gly Pro Gly
            1025            1030            1035

Ser Gly Gln Gln Gly Gln Gly Pro Tyr Gly Pro Gly Ala Ser Ala
            1040            1045            1050

Ala Ala Ala Ala Gly Gln Tyr Gly Pro Gly Gln Gln Gly Pro Tyr
            1055            1060            1065

Gly Pro Gly Gln Ser Ala Ala Ala Ala Gly Pro Gly Ser Gly
            1070            1075            1080

Gln Tyr Gly Pro Gly Ala Ser Gly Gln Asn Gly Pro Gly Ser Gly
            1085            1090            1095

Gln Tyr Gly Pro Gly Gln Gln Gly Pro Gly Gln Ser Ala Ala Ala
            1100            1105            1110

Ala Ala Gly Gln Tyr Gln Gln Gly Pro Gly Gln Gln Gly Pro Tyr
            1115            1120            1125

Gly Pro Gly Ala Ser Ala Ala Ala Ala Ala Gly Gln Tyr Gly Ser
            1130            1135            1140

Gly Pro Gly Gln Gln Gly Pro Tyr Gly Pro Gly Gln Ser Gly Ser
            1145            1150            1155

Gly Gln Gln Gly Pro Gly Gln Gly Pro Tyr Ala Ser Ala Ala
            1160            1165            1170

Ala Ala Ala Gly Pro Gly Ser Gly Gln Gln Gly Pro Gly Ala Ser
            1175            1180            1185
```